United States Patent
Bohnert et al.

(10) Patent No.: US 7,091,402 B2
(45) Date of Patent: Aug. 15, 2006

(54) PROTEIN PHOSPHATES STRESS-RELATED POLYPEPTIDES AND METHODS OF USE IN PLANTS

(75) Inventors: Hans J. Bohnert, Champaign, IL (US); Ruoying Chen, Apex, NC (US); Manabu Ishitani, Cary, NC (US); Nocha Van Thielen, Chapel Hill, NC (US); Oswaldo da Costa e Silva, Cary, NC (US)

(73) Assignee: BASF Plant Science GmbH, Ludwigshafen (DE)

( * ) Notice: Subject to any disclaimer, the term of this patent is extended or adjusted under 35 U.S.C. 154(b) by 415 days.

(21) Appl. No.: 10/236,699

(22) Filed: Sep. 5, 2002

(65) Prior Publication Data

US 2003/0150028 A1  Aug. 7, 2003

Related U.S. Application Data

(60) Provisional application No. 60/317,305, filed on Sep. 5, 2001.

(51) Int. Cl.
*C12N 15/82* (2006.01)
*C12N 15/29* (2006.01)

(52) U.S. Cl. .................... 800/289; 536/23.6
(58) Field of Classification Search ............. 536/23.6; 800/278, 289; 435/410, 419, 468
See application file for complete search history.

(56) References Cited

OTHER PUBLICATIONS

Csordas et al., Plant Mol. Biol., Jul. 2000, vol. 43, pp. 527-536.*
Horsch et al., Science, 1985, vol. 227, pp. 1229-1231.*
Ishida et al., Nature Biotech., 1996, vol. 14, pp. 745-750.*
MacKintosh & Cohen, 1989, "Identification of High Levels of Type 1 and Type 2A Protein Phosphatase in Higher Plants", Biochem. J. 262:335-339.
Pardo et al., 1998, "Stress Signaling Through $Ca^{2+}$/Calmodulin-Dependent Protein Phosphatase Calcineurin Mediates Salt Adaptation in Plants", Proc. Natl. Acad. Sci. USA 95:9681-9686.
Sheen, J., 1998, "Mutational Analysis of Protein Phosphatase 2C Involved in Abscisic Acid Signal Transduction in Higher Plants", Proc. Natl. Acad. Sci. USA 95:975-980.
Smith & Walker, 1996, "Plant Protein Phosphatases", Annu. Rev. Plant Physiol. Plant Mol. Biol. 47:101-125.
Casamayor et al., Molecular Characterization of a Fourth Isoform of the Catalytic Subunit of Protein Phosphatase 2A from *Arabidopsis thaliana*, Plant Mol. Biol., 1994, 26:253-528.
Watillion et al., Cloning and Characterization of Ser/Thr Protein Phosphatase Transcripts in Apple, Plant Sci., 1995, 108:155-164.
Yasukazu, N. Database Embl-EBI, Accession No. AP002050, May 16, 2000, pp. 1-12.
Cherel et al., Physical and Functional Interaction of the Arabidopsis K+ Channel AKT2 and Phosphatase AtPP2CA, Plant Cell, 2002, 14:1133-1146.
Cunningham & Fink, 1996, "Calcineurin Inhibits *VCX1*-Dependent $H^+/Ca^{2+}$ Exchange and Induces $Ca^{2+}$ ATPases in *Saccharomyces cerevisiae*", Mol. Cell. Biol. 16:2226-2237.

* cited by examiner

*Primary Examiner*—Ashwin Mehta
(74) *Attorney, Agent, or Firm*—Ruoying Chen; Mark A. Westhafer

(57) ABSTRACT

A transgenic plant transformed by a Protein Phosphatase Stress-Related Polypeptide (PPSRP) coding nucleic acid, wherein expression or repression of the nucleic acid sequence in the plant results in increased tolerance to environmental stress as compared to a wild type variety of the plant. Also provided are agricultural products, including seeds, produced by the transgenic plants. Also provided are isolated PPSRPs, and isolated nucleic acid coding PPSRPs, and vectors and host cells containing the latter.

9 Claims, 9 Drawing Sheets

LB  g7T  aacCI  nosP  Super promoter  "Gene of Interest"  NOSpA  RB pBPSJH001

Figure 2

```
                        1                                              40
PpPP2A-1     (1)   --MSVPPISS-NGQLDTQIAQLIQCKPLS--------EVE
OsPP2A-5     (1)   --------MPSHADLERQIEQLMECKPLS--------ESE
OsPP2A-4     (1)   -------MSSPHGGLDDQIERLMQCKPLP--------EPE
OsPP2A-3     (1)   ---------MDPVLLDDITRRLIEVKNLKPGKNAQLSESE
OsPP2A-2     (1)   -------MPSSHGDLDRQIAQIRECKHLA--------EGE
OsPP2A-1     (1)   MEESVGSRGGGGGGLDAQIEQLMECRPLS--------EPE
Consensus    (1)             M S HG LD QIEQLMECKPLS        E E
                        41                                             80
PpPP2A-1    (30)   VRGLCEKAKEILMRENNVQPVKCPVTICGDIHGQFHDLAE
OsPP2A-5    (25)   VKALCDQARAILVEEWNVQPVKCPVTVCGDIHGQFYDLIE
OsPP2A-4    (26)   VRALCEKAKEILMEESNVQPVKSPVTICGDIHGQFHDLAE
OsPP2A-3    (32)   IKQLCATSKEIFLNQPNLLELEAPIKICGDVHGQYSDLLR
OsPP2A-2    (26)   VRALCEQAKAILMEEWNVQPVRCPVTVCGDIHGQFYDLIE
OsPP2A-1    (33)   VKTLCEKAKEILMEESNVQPVKSPVTICGDIHGQFHDLVE
Consensus   (41)   VKALCEKAKEILMEE NVQPVKCPVTICGDIHGQFHDLIE
                        81                                            120
PpPP2A-1    (70)   LFRIGGMCPDTNYLFMGDYVDRGYYSVETATLLVALKVRY
OsPP2A-5    (65)   LFRIGGNAPDTNYLFMGDYVDRGYYSVETVTLLVALKVRY
OsPP2A-4    (66)   LFRIGGKCPDTNYLFMGDYVDRGYYSVETVTLLVALKVRY
OsPP2A-3    (72)   LFDYGGYPPQSNYLFLGDYVDRGKQSLETICLLLAYKIKY
OsPP2A-2    (66)   LFRIGGEAPDTNYLFMGDYVDRGYYSVETVSLLVALKVRY
OsPP2A-1    (73)   LFRIGGKCPDTNYLFMGDYVDRGYYSVETVTLLVALKVRY
Consensus   (81)   LFRIGG CPDTNYLFMGDYVDRGYYSVETVTLLVALKVRY
                        121                                           160
PpPP2A-1   (110)   PDRITILRGNHESRQITQVYGFYDECLRKYGNANVWKIFT
OsPP2A-5   (105)   RDRITILRGNHESRQITQVYGFYDECLRKYGNANVWKYFT
OsPP2A-4   (106)   PQRITILRGNHESRQITQVYGFYDECLRKYGNANVWKTFT
OsPP2A-3   (112)   PENFFLLRGNHECASVNRIYGFYDECKRRFS-VKLWKTFT
OsPP2A-2   (106)   RDRITILRGNHESRQITQVYGFYDECLRKYGNANVWKYFT
OsPP2A-1   (113)   PQRITILRGNHESRQITQVYGFYDECLRKYGSANVWKIFT
Consensus  (121)   PDRITILRGNHESRQITQVYGFYDECLRKYGNANVWK FT
                        161                                           200
PpPP2A-1   (150)   DLFDYFPLTALVESEIFCLHGGLSPSIDSLDHIRDLDRVQ
OsPP2A-5   (145)   DLFDYLPLTALIESQIFCLHGGLSPSIDTLDNIRALDRIQ
OsPP2A-4   (146)   DLFDYFPLTALVESEIFCLHGGLSPSIETLDNIRNFDRVQ
OsPP2A-3   (151)   DCFNCLPVAALIDEKILCMHGGLSPEINKLDQILNLNRPT
OsPP2A-2   (146)   DLFDYLPLTALIENQVFCLHGGLSPSLDTLDNIRALDRIQ
OsPP2A-1   (153)   DLFDYFPLTALVESEIFCLHGGLSPSIDNLDSVRSLDRVQ
Consensus  (161)   DLFDYLPLTALIESEIFCLHGGLSPSIDTLDNIRALDRVQ
                        201                                           240
PpPP2A-1   (190)   EVPHEGPMCDLLWSDP-DDRCGWGISPRGAGYTFGQDISE
OsPP2A-5   (185)   EVPHEGPMCDLLWSDP-DDRCGWGISPRGAGYTFGQDIAA
OsPP2A-4   (186)   EVPHEGPMCDLLWSDP-DDRCGWGISPRGAGYTFGQDISE
OsPP2A-3   (191)   DVPDTGLLCDLLWSDPSNDAQGWAMNDRGVSYTFGPDKVS
OsPP2A-2   (186)   EVPHEGPMCDLLWSDP-DDRCGWGISPRGAGYTFGQDIAQ
OsPP2A-1   (193)   EVPHEGPMCDLLWSDP-DDRCGWGISPRGAGYTFGQDISE
Consensus  (201)   EVPHEGPMCDLLWSDP DDRCGWGISPRGAGYTFGQDISE
```

Figure 2 Continued

```
              241                                             280
PpPP2A-1  (229) QFNHNNNLKLVARAHQLVMEGYNWGHEHKVVTIFSAPNYC
OsPP2A-5  (224) QFNHTNGLSLISRAHQLVMEGFNWCQDKNVVTVFSAPNYC
OsPP2A-4  (225) QFNHTNNLRLIARAHQLVMEGFNWAHEQKVVTIFSAPNYC
OsPP2A-3  (231) EFLEKHDLDLICRAHQVVEDGYEFFANRQLVTIFSAPNYC
OsPP2A-2  (225) QFNHTNGLSLISRAHQLVMEGFNWCQDKNVVTVFSAPNYC
OsPP2A-1  (232) QFNHTNNLKLVARAHQLVMEGYNWAHEQKVVTIFSAPNYC
Consensus (241) QFNHTNNLKLIARAHQLVMEGFNWAHEKKVVTIFSAPNYC
              281                                             320
PpPP2A-1  (269) YRCGNMASILEVDDNMGHTFIQFEPAPRRGEPDVTRRTPD
OsPP2A-5  (264) YRCGNMAAILEIGENMDQNFLQFDPAPRQIEPDTTRKTPD
OsPP2A-4  (265) YRCGNMASILEVDDCREHTFIQFEPAPRRGEPDVTRRTPD
OsPP2A-3  (271) GEFDNAGAMMSVDDTLMCSFQILKPARKMLGGSTNSKSGF
OsPP2A-2  (265) YRCGNMAAILEIGENMDQNFLQFDPAPRQIEPDTTRKTPD
OsPP2A-1  (272) YRCGNMASILEVDDCRNHTFIQFEPAPRRGEPDVTRRTPD
Consensus (281) YRCGNMAAILEVDDNMDHTFIQFEPAPRRGEPDVTRKTPD
              321
PpPP2A-1  (309) YFL----
OsPP2A-5  (304) YFL----
OsPP2A-4  (305) YFL----
OsPP2A-3  (311) KSLRGW-
OsPP2A-2  (305) YFL----
OsPP2A-1  (312) YFL----
Consensus (321) YFL
```

Figure 3

```
                    1                                           40
PpPP2A-1    (1)  ---MSVPPISSNG--QLDTQIAQLIQCK------PLSEVE
GmPP2A-5    (1)  ----------MPSHADLERQIEQLMDCK------PLSESE
GmPP2A-4    (1)  --------MEQSLLDDIINRLLEVPTLPAK--QVQLSESE
GmPP2A-3    (1)  ---MGANSMLSESSHDLDDQISQLMQCK------PLSEQQ
GmPP2A-2    (1)  MSTQGQVITDEAVLDDIIRRLTEMRLARPG-KQVQLSESE
GmPP2A-1    (1)  ---------------MDLDQWISKVKEGQ------HLLEDE
BnPP2A-3    (1)  MTQQGQGSMDPAVLDDIIRRLLDYRNPKPGTKQVMLNESE
BnPP2A-2    (1)  --------MDENLLDDIIRRLLETNNGK----QVKLLEAE
BnPP2A-1    (1)  ----------MPETGDIDRQIEQLMECK------ALSEAE
Consensus   (1)            M       DIDR I  L  K         LSESE
                    41                                          80
PpPP2A-1   (30)  VRGLCEKAKEILMRENNVQPVKCPVTICGDIHGQFHDIAE
GmPP2A-5   (25)  VKALCDQARTILVEEWNVQPVKCPVTVCGDIHGQFYDLIE
GmPP2A-4   (31)  IRQLCVVSREIFLQQPNLLELEAPIKICGDVHGQYSDLLR
GmPP2A-3   (32)  VRGLCEKAKEILMDESNVQPVKSPVTICGDIHGQFHDIAE
GmPP2A-2   (40)  IKQLCVASRDIFINQPNLLELEAPIKICGDIHGQYSDLLR
GmPP2A-1   (21)  LQLLCEYVKEILIEESNVQPVNSPVTVCGDIHGQFHDLMK
BnPP2A-3   (41)  IRQLCSVSREIFLQQPNLLELEAPIKICGDIHGQYSDLLR
BnPP2A-2   (29)  IRQLCSASKEVFLSQPNLLELEAPIKICGDVHGQFPDLLR
BnPP2A-1   (25)  VKTLCEQARAILVEEWNVQPVKCPVTVCGDIHGQFYDLIE
Consensus  (41)  IR LCE AREILL E NVQPV APVTICGDIHGQFHDLLR
                    81                                         120
PpPP2A-1   (70)  LFRIGGMCPDTNYLFMGDYVDRGYYSVETAILLVALKVRY
GmPP2A-5   (65)  LFRIGGNAPDTNYLFMGDYVDRGYYSVETVTLLVALKVRY
GmPP2A-4   (71)  LFEYGGLPPEANYLFLGDYVDRGKQSLETICLILAYKIKY
GmPP2A-3   (72)  LFRIGGKCPDTNYLFMGDYVDRGYYSVETVSLLVALKVRY
GmPP2A-2   (80)  LFEYGGLPPTANYLFLGEYVDRGKQSLETICLILAYKIKY
GmPP2A-1   (61)  LFQTGGHVPETNYIFMGDFVDRGYNSLEVFTILLLLKARY
BnPP2A-3   (81)  LFEYGGLPPAANYLFLGDYVDRGKQSLETICLILAYKIKY
BnPP2A-2   (69)  LFEYGGYPPAANYLFLGDYVDRGKRSIETICLILAYKLKY
BnPP2A-1   (65)  LFKIGGSSPDTNYLFMGDYVDRGYYSVETVSLLVALKVRY
Consensus  (81)  LF  GG   PDTNYLFMGDYVDRGY SLETITLLLALKVRY
                    121                                        160
PpPP2A-1  (110)  PDRITILRGNHESRQITQVYGFYDECLRKYGNANVWKIFT
GmPP2A-5  (105)  RDRITLLRGNHESRQITQVYGFYDECLRKYGNANVWKYFT
GmPP2A-4  (111)  PENFFLLRGNHECASINRIYGFYDECKRRFN-VRLWKTFT
GmPP2A-3  (112)  PQRITLLRGNHESRQITQVYGFYDECLRKYGNANVWKTFT
GmPP2A-2  (120)  PENFFLLRGNHECASINRIYGFYDECKRRFN-VRLWKAFT
GmPP2A-1  (101)  PANITLLRGNHESRQLTQVYGFYDECQRKYGNANAWRYCT
BnPP2A-3  (121)  PENFFLLRGNHECASINRIYGFYDERKRRFS-VRLWKVFT
BnPP2A-2  (109)  KLNFFLLRGNHECASINRVYGFYDECKRRYN-VRLWKSFT
BnPP2A-1  (105)  RDRITLLRGNHESRQITQVYGFYDECLRKYGNANVWKHFT
Consensus (121)  PDNITLLRGNHESRQITQVYGFYDEC RKYGNANLWK FT
```

Figure 3 Continued

```
              161                                          200
PpPP2A-1  (150) DLFDYFPLTALVESEIFCLHGGLSPSIDSLDHIRDLDRVQ
GmPP2A-5  (145) DLFDYLPLTALIESQIFCLHGGLSPSLDTLDNIRALDRIQ
GmPP2A-4  (150) DCFNCLPVAALVDEKILCMHGGLSPDLNNLDQIRNLQRPT
GmPP2A-3  (152) DLFDFFPLTALVESEIFCLHGGLSPSIETLDNIRNFDRVQ
GmPP2A-2  (159) DCFNFLPVAALIDDKILCMHGGLSPELTNLDEIRNLPRPT
GmPP2A-1  (141) DVFDYLTLSAIIDGTVLCVHGGLSPDIRTIDQIRVIDRNC
BnPP2A-3  (160) DSFNCLPVAAVIDDKILCMHGGLSPDLTSVEQIKNIKRPT
BnPP2A-2  (148) DCFNCLPVAALIDDKILCMHGGLSPDLKTLDDIRRIPRPV
BnPP2A-1  (145) DLFDYLPLTALIESQVFCLHGGLSPSLDTLDNIRSLDRIQ
Consensus (161) DLFDYLPLTALID   ILCLHGGLSPDL TLDNIR LDR
                201                                          240
PpPP2A-1  (190) EVPHEGPMCDLLWSDP-DDRCGWGISPRGAGYTFGQDISE
GmPP2A-5  (185) EVPHEGPMCDLLWSDP-DDRCGWGISPRGAGYTFGQDIAA
GmPP2A-4  (190) DVPDTGLLCDLLWSDPSKDVQGWGMNDRGVSYTFGADKVS
GmPP2A-3  (192) EVPHEGPMCDLLWSDP-DDRCGWGISPRGAGYTFGQDISE
GmPP2A-2  (199) AIPDTGLLCDLLWSDPGRDVKGWGMNDRGVSYTFGPDKVA
GmPP2A-1  (181) EIPHEGPFCDLMWSDP-EDIETWAVSPRGAGWLFGSRVTS
BnPP2A-3  (200) DVPDSGLLCDLLWSDPSKDVKGWGMNDRGVSYTFGPDKVA
BnPP2A-2  (188) DVPDQGVLCDLLWADPDKEIQGWGENDRGVSYTFGPDKVA
BnPP2A-1  (185) EVPHEGPMCDLLWSDP-DDRCGWGISPRGAGYTFGQDIAT
Consensus (201) EVPHEGPLCDLLWSDP DDV GWGISPRGAGYTFG DI A
                241                                          280
PpPP2A-1  (229) QFNHNNNLKLVARAHQLVMEGYNWGHEHK-VVTIFSAPNY
GmPP2A-5  (224) QFNHTNGLSLISRAHQLVMEGFNWCQDKN-VVTVFSAPNY
GmPP2A-4  (230) QFLQKHDLDLVCRAHQVVEDGYEFFANRQ-LVTIFSAPNY
GmPP2A-3  (231) QFNHTNSLKLIARAHQLVMDGFNWAHEQK-VVTIFSAPNY
GmPP2A-2  (239) EFLTKHDLDLICRAHQVVEDGYEFFADRQ-LVTIFSAPNY
GmPP2A-1  (220) EFNHINNLDLVCRAHQLVQEGLKYMFQDKGLVTVWSAPNY
BnPP2A-3  (240) EFLIKNDMDLICRAHQVVEDGYEFFADRQ-LVTIFSAPNY
BnPP2A-2  (228) EFLQTHDLDLVCRAHQVVEDGYEFFAKRQ-LVTIFSAPNY
BnPP2A-1  (224) QFNHTNGLSLISRAHQLVMEGYNWCQEKN-VVTVFSAPNY
Consensus (241) QFNH N LDLICRAHQLV DGY F  DRQ LVTIFSAPNY
                281                                          320
PpPP2A-1  (268) CYRCGNMASILEVDDNMGHTFIQFEPAPRRGEPDVIRRTP
GmPP2A-5  (263) CYRCGNMAAILEIGENMDQNFLQFDPAPRQIEPDTIRKTP
GmPP2A-4  (269) CGEFDNAGAMMSVDETLMCSFQILKPADKKAKLNFGSTTT
GmPP2A-3  (270) CYRCGNMASILEVDDCKGHTFIQFEPAPRRGEPDVIRRTP
GmPP2A-2  (278) CGEFDNAGAMMSVDENLMCSFQILKPAEKKSKFVMSNKM-
GmPP2A-1  (260) CYRCGNVASILSFNENMEREVKFFTETEENNQMRGPRTGV
BnPP2A-3  (279) CGEFDNAGAMMSVDES------------------------
BnPP2A-2  (267) CGEFDNAGAMMSVDDSLTCSFQILKSTEKKGRFGYNNNVH
BnPP2A-1  (263) CYRCGNMAAILEIDENMDQNFLQFDPAPRQVEPETIRKTP
Consensus (281) CYRCGNMAAILSVDENM   SF F PA RK       TRKT
```

Figure 3 Continued

```
                       321              336
PpPP2A-1    (308)   DYFL------------
GmPP2A-5    (303)   DYFL------------
GmPP2A-4    (309)   AKPGNSPAGVKVGRY-
GmPP2A-3    (310)   DYFL------------
GmPP2A-2    (317)   ----------------
GmPP2A-1    (300)   PYFL------------
BnPP2A-3    (295)   ----------------
BnPP2A-2    (307)   RPGTPPHKGGKGG---
BnPP2A-1    (303)   DYFL------------
Consensus   (321)    YFL
```

Figure 4

```
                1                                       40
PpPP2A-1    (1)  ---MSVPPISSNGQLDTQIAQLIQCKPLS---------EV
OsPP2A-5    (1)  --------MPSHADLERQIEQLMECKPLS---------ES
OsPP2A-4    (1)  ------MSSPHGGLDDQIERLMQCKPLP---------EP
OsPP2A-3    (1)  ---------MDPVLLDDIIRRLIEVKNLKPG-KNAQLSES
OsPP2A-2    (1)  -------MPSSHGDLDRQIAQLRECKHLA---------EG
OsPP2A-1    (1)  MEESVGSRGGGGGGLDAQIEQLMECRPLS---------EP
GmPP2A-5    (1)  --------MPSHADLERQIEQLMDCKPLS---------ES
GmPP2A-4    (1)  ---------MEQSLLDDIINRLIEVPTL-PA-KQVQLSES
GmPP2A-3    (1)  -MGANSMLSESSHDLDDQISQLMQCKPLS---------EQ
GmPP2A-2    (1)  -MSTQGQVIIDEAVLDDIIRRLTEVRLARPG-KQVQLSES
GmPP2A-1    (1)  ------------MDLDQWISKVKEGQHLL---------ED
BnPP2A-3    (1)  -MTQQGQGSMDPAVLDDIIRRLLDYRNPKPGTKQVMLNES
BnPP2A-2    (1)  ----------MDENLLDDIIRRLIETNNG----KQVKLLEA
BnPP2A-1    (1)  --------MPETGDIDRQIEQLMECKALS---------EA
Consensus   (1)           G LDDQI QLMECK LS           ES
                 41                                      80
PpPP2A-1   (29)  EVRGLCEKAKEILMRENNVQPVKCPVTICGDIHGQFHDIA
OsPP2A-5   (24)  EVKALCDQARAILVEEWNVQPVKCPVTVCGDIHGQFYDLI
OsPP2A-4   (25)  EVRALCEKAKEILMEESNVQPVKSPVTICGDIHGQFHDLA
OsPP2A-3   (31)  EIKQLCATSKEIFLNQPNLLELEAPIKICGDVHGQYSDLL
OsPP2A-2   (25)  EVRALCEQAKAILMEEWNVQPVRCPVTVCGDIHGQFYDLI
OsPP2A-1   (32)  EVKTLCEKAKEILMEESNVQPVKSPVTICGDIHGQFHDLV
GmPP2A-5   (24)  EVKALCDQARTILVEEWNVQPVKCPVTVCGDIHGQFYDLI
GmPP2A-4   (30)  EIRQLCVVSREIFLQQPNLLELEAPIKICGDVHGQYSDLL
GmPP2A-3   (31)  QVRGLCEKAKEILMDESNVQPVKSPVTICGDIHGQFHDLA
GmPP2A-2   (39)  EIKQLCVASRDIFINQPNLLELEAPIKICGDIHGQYSDLL
GmPP2A-1   (20)  ELQLLCEYVKEILIEESNVQPVNSPVTVCGDIHGQFHDLM
BnPP2A-3   (40)  EIRQLCSVSREIFLQQPNLLELEAPIKICGDIHGQYSDLI
BnPP2A-2   (28)  EIRQLCSASKEVFLSQPNLLELEAPIKICGDVHGQFPDLI
BnPP2A-1   (24)  EVKTLCEQARAILVEEWNVQPVKCPVTVCGDIHGQFYDLI
Consensus  (41)  EVR LCE AKEILMEE NVQPVKAPVTICGDIHGQFHDLL
                 81                                     120
PpPP2A-1   (69)  ELERIGGMCPDTNYLFMGDYVDRGYYSVETAILLVALKVR
OsPP2A-5   (64)  ELFRIGGNAPDTNYLFMGDYVDRGYYSVETVTLLVALKVR
OsPP2A-4   (65)  ELFRIGGKCPDTNYLFMGDYVDRGYYSVETVILLVALKVR
OsPP2A-3   (71)  RLFDYGGYPPQSNYLFLGDYVDRGKQSLETICLLLAYKIK
OsPP2A-2   (65)  ELFRIGGEAPDTNYLFMGDYVDRGYYSVETVSLLVALKVR
OsPP2A-1   (72)  ELFRIGGKCPDTNYLFMGDYVDRGYYSVETVILLVALKVR
GmPP2A-5   (64)  ELFRIGGNAPDTNYLFMGDYVDRGYYSVETVTLLVALKVR
GmPP2A-4   (70)  RLFEYGGLPPEANYLFLGDYVDRGKQSLETICLLLAYKIK
GmPP2A-3   (71)  ELFRIGGKCPDTNYLFMGDYVDRGYYSVETVSLLVALKVR
GmPP2A-2   (79)  RLFEYGGLPPTANYLFLGEYVDRGKQSLETICLLLAYKIK
GmPP2A-1   (60)  KLFQTGGHVPETNYIFMGDEVDRGYNSLEVFTILLLLKAR
BnPP2A-3   (80)  RLFEYGGLPPAANYLFLGDYVDRGKQSLETICLLLAYKIK
BnPP2A-2   (68)  RLFEYGGYPPAANYLFLGDYVDRGKRSIETICLLLAYKLK
BnPP2A-1   (64)  ELFKIGGSSPDTNYLFMGDYVDRGYYSVETVSLLVALKVR
Consensus  (81)  ELFRIGG   PDTNYLFMGDYVDRGYYSVETVTLLVALKVR
```

Figure 4 Continued

```
                  121                                        160
PpPP2A-1   (109)  YPDRITILRGNHESRQITQVYGFYDECLRKYGNANVWKIF
OsPP2A-5   (104)  YRDRITILRGNHESRQITQVYGFYDECLRKYGNANVWKYF
OsPP2A-4   (105)  YPQRITILRGNHESRQITQVYGFYDECLRKYGNANVWKTF
OsPP2A-3   (111)  YPENFFLLRGNHECASVNRIYGFYDECKRRFS-VKLWKTF
OsPP2A-2   (105)  YRDRITILRGNHESRQITQVYGFYDECLRKYGNANVWKYF
OsPP2A-1   (112)  YPQRITILRGNHESRQITQVYGFYDECLRKYGSANVWKIF
GmPP2A-5   (104)  YRDRITILRGNHESRQITQVYGFYDECLRKYGNANVWKYF
GmPP2A-4   (110)  YPENFFLLRGNHECASINRIYGFYDECKRRFN-VRLWKTF
GmPP2A-3   (111)  YPQRITILRGNHESRQITQVYGFYDECLRKYGNANVWKTF
GmPP2A-2   (119)  YPENFFLLRGNHECASINRIYGFYDECKRRFN-VRLWKAF
GmPP2A-1   (100)  YPANITLLRGNHESRQLTQVYGFYDECQRKYGNANAWRYC
BnPP2A-3   (120)  YPENFFLLRGNHECASINRIYGFYDERKRRFS-VRLWKVF
BnPP2A-2   (108)  YKLNFFLLRGNHECASINRVYGFYDECKRRYN-VRLWKSF
BnPP2A-1   (104)  YRDRITILRGNHESRQITQVYGFYDECLRKYGNANVWKHF
Consensus  (121)  YPDRITILRGNHESRQITQVYGFYDECLRKYGNANVWK F 161                                        200
PpPP2A-1   (149)  TDLFDYFPLTALVESEIFCLHGGLSPSIDSLDHIRDLDRV
OsPP2A-5   (144)  TDLFDYLPLTALIESQIFCLHGGLSPSLDTLDNIRALDRI
OsPP2A-4   (145)  TDLFDYFPLTALVESEIFCLHGGLSPSLETLDNIRNFDRV
OsPP2A-3   (150)  TDCFNCLPVAALIDEKILCMHGGLSPELNKLDQILNLNRP
OsPP2A-2   (145)  TDLFDYLPLTALIENQVFCLHGGLSPSLDTLDNIRALDRI
OsPP2A-1   (152)  TDLFDYFPLTALVESEIFCLHGGLSPSIDNLDSVRSLDRV
GmPP2A-5   (144)  TDLFDYLPLTALIESQIFCLHGGLSPSLDTLDNIRALDRI
GmPP2A-4   (149)  TDCFNCLPVAALVDEKILCMHGGLSPDLNNLDQIRNLQRP
GmPP2A-3   (151)  TDLFDFFPLTALVESEIFCLHGGLSPSIETLDNIRNFDRV
GmPP2A-2   (158)  TDCFNELPVAALIDDKILCMHGGLSPELTNLDEIRNLPRP
GmPP2A-1   (140)  TDVFDYLTLSAIIDGTVLCVHGGLSPDIRTIDQIRVIDRN
BnPP2A-3   (159)  TDSFNCLPVAAVIDDKILCMHGGLSPDLTSVEQIKNIKRP
BnPP2A-2   (147)  TDCFNCLPVAALIDDKILCMHGGLSPDLKTLDDIRRIPRP
BnPP2A-1   (144)  TDLFDYLPLTALIESQVFCLHGGLSPSLDTLDNIRSLDRI
Consensus  (161)  TDLFDYLPLTALIES IFCLHGGLSPSLDTLDNIR LDRI 201                                        240
PpPP2A-1   (189)  QEVPHEGPMCDLLWSDP-DDRCGWGISPRGAGYTFGQDIS
OsPP2A-5   (184)  QEVPHEGPMCDLLWSDP-DDRCGWGISPRGAGYTFGQDIA
OsPP2A-4   (185)  QEVPHEGPMCDLLWSDP-DDRCGWGISPRGAGYTFGQDIS
OsPP2A-3   (190)  TDVPDTGLLCDLLWSDPSNDAQGWAMNDRGVSYTFGPDKV
OsPP2A-2   (185)  QEVPHEGPMCDLLWSDP-DDRCGWGISPRGAGYTFGQDIA
OsPP2A-1   (192)  QEVPHEGPMCDLLWSDP-DDRCGWGISPRGAGYTFGQDIS
GmPP2A-5   (184)  QEVPHEGPMCDLLWSDP-DDRCGWGISPRGAGYTFGQDIA
GmPP2A-4   (189)  TDVPDTGLLCDLLWSDPSKDVQGWGMNDRGVSYTFGADKV
GmPP2A-3   (191)  QEVPHEGPMCDLLWSDP-DDRCGWGISPRGAGYTFGQDIS
GmPP2A-2   (198)  TAIPDTGLLCDLLWSDPGRDVKGWGMNDRGVSYTFGPDKV
GmPP2A-1   (180)  CEIPHEGPFCDLMWSDP-EDIETWAVSPRGAGWLFGSRVT
BnPP2A-3   (199)  TDVPDSGLLCDLLWSDPSKDVKGWGMNDRGVSYTFGPDKV
BnPP2A-2   (187)  VDVPDQGVLCDLLWADPDKEIQGWGENDRGVSYTFGPDKV
BnPP2A-1   (184)  QEVPHEGPMCDLLWSDP-DDRCGWGISPRGAGYTFGQDIA
Consensus  (201)  QEVPHEGPMCDLLWSDP DDRCGWGISPRGAGYTFGQDIA
```

Figure 4 Continued

```
              241                                            280
PpPP2A-1  (228) EQFNHNNNLKLVARAHQLVMEGYNWGHEHK-VVTIFSAPN
OsPP2A-5  (223) AQFNHTNGLSLISRAHQLVMEGFNWCQDKN-VVTVFSAPN
OsPP2A-4  (224) EQFNHTNNLRLIARAHQLVMEGFNWAHEQK-VVTIFSAPN
OsPP2A-3  (230) SEFLEKHDLDLICRAHQVVEDGYEFFANRQ-LVTIFSAPN
OsPP2A-2  (224) QQFNHTNGLSLISRAHQLVMEGFNWCQDKN-VVTVFSAPN
OsPP2A-1  (231) EQFNHTNNLKLVARAHQLVMEGYNWAHEQK-VVTIFSAPN
GmPP2A-5  (223) AQFNHTNGLSLISRAHQLVMEGFNWCQDKN-VVTVFSAPN
GmPP2A-4  (229) SQFLQKHDLDLVCRAHQVVEDGYEFFANRQ-LVTIFSAPN
GmPP2A-3  (230) EQFNHTNSLKLIARAHQLVMDGFNWAHEQK-VVTIFSAPN
GmPP2A-2  (238) AEFLTKHDLDLICRAHQVVEDGYEFFADRQ-LVTIFSAPN
GmPP2A-1  (219) SEFNHINNLDLVCRAHQLVQEGLKYMFQDKGLVTVWSAPN
BnPP2A-3  (239) AEFLIKNDMDLICRAHQVVEDGYEFFADRQ-LVTIFSAPN
BnPP2A-2  (227) AEFLQTHDLDLVCRAHQVVEDGYEFFAKRQ-LVTIFSAPN
BnPP2A-1  (223) TQFNHTNGLSLISRAHQLVMEGYNWCQEKN-VVTVFSAPN
Consensus (241) AQFNHTN L LIARAHQLVMEGYNW  DRQ VVTIFSAPN
              281                               320
PpPP2A-1  (267) YCYRCGNMASILEVDDNMGHTFLQFEPAPRRGEPDVTRRT
OsPP2A-5  (262) YCYRCGNMAAILETGENMDQNFLQFDPAPRQIEPDTTRKT
OsPP2A-4  (263) YCYRCGNMASILEVDDCREHTFTQFEPAPRRGEPDVTRRT
OsPP2A-3  (269) YCGEFDNAGAMMSVDDTLMCSFQILKPARKMLGGSTNSKS
OsPP2A-2  (263) YCYRCGNMAAILETGENMDQNFLQFDPAPRQIEPDTTRKT
OsPP2A-1  (270) YCYRCGNMASILEVDDCRNHTFIQFEPAPRRGEPDVTRRT
GmPP2A-5  (262) YCYRCGNMAAILETGENMDQNFLQFDPAPRQIEPDTTRKT
GmPP2A-4  (268) YCGEFDNAGAMMSVDETLMCSFQILKPADKKAKLNFGSTT
GmPP2A-3  (269) YCYRCGNMASILEVDDCKGHTFIQFEPAPRRGEPDVTRRT
GmPP2A-2  (277) YCGEFDNAGAMMSVDENLMCSFQILKPAEKKSKFVMSNKM
GmPP2A-1  (259) YCYRCGNVASILSFNENMEREVKFFTETEENNQMRGPRTG
BnPP2A-3  (278) YCGEFDNAGAMMSVDES-----------------------
BnPP2A-2  (266) YCGEFDNAGAMMSVDDSLTCSFQILKSTEKKGRFGYNNNV
BnPP2A-1  (262) YCYRCGNMAAILETDENMDQNFLQFDPAPRQVEPETTRKT
Consensus (281) YCYRCGNMAAILEVDENM  SFIQFDPAPRR EPD TRKT
              321          337
PpPP2A-1  (307) PDYFL------------
OsPP2A-5  (302) PDYFL------------
OsPP2A-4  (303) PDYFL------------
OsPP2A-3  (309) GFKSLRGW---------
OsPP2A-2  (303) PDYFL------------
OsPP2A-1  (310) PDYFL------------
GmPP2A-5  (302) PDYFL------------
GmPP2A-4  (308) TAKPGNSPAGVKVGRY-
GmPP2A-3  (309) PDYFL------------
GmPP2A-2  (317) -----------------
GmPP2A-1  (299) VPYFL------------
BnPP2A-3  (295) -----------------
BnPP2A-2  (306) HRPGTPPHKGGKGG---
BnPP2A-1  (302) PDYFL------------
Consensus (321) PDYFL
```

PROTEIN PHOSPHATES STRESS-RELATED POLYPEPTIDES AND METHODS OF USE IN PLANTS

CROSS-REFERENCE TO RELATED APPLICATIONS

The present invention claims the priority benefit of U.S. Provisional Patent Application Ser. No. 60/317,305 filed Sep. 5, 2001, the entire contents of which are hereby incorporated by reference.

BACKGROUND OF THE INVENTION

1. Field of the Invention

This invention relates generally to nucleic acid sequences encoding polypeptides that are associated with abiotic stress responses and abiotic stress tolerance in plants. In particular, this invention relates to nucleic acid sequences encoding polypeptides that confer drought, cold, and/or salt tolerance to plants.

2. Background Art

Abiotic environmental stresses, such as drought stress, salinity stress, heat stress, and cold stress, are major limiting factors of plant growth and productivity. Crop losses and crop yield losses of major crops such as soybean, rice, maize (corn), cotton, and wheat caused by these stresses represent a significant economic and political factor and contribute to food shortages in many underdeveloped countries.

Plants are typically exposed during their life cycle to conditions of reduced environmental water content. Most plants have evolved strategies to protect themselves against these conditions of desiccation. However, if the severity and duration of the drought conditions are too great, the effects on development, growth, and yield of most crop plants are profound. Continuous exposure to drought conditions causes major alterations in the plant metabolism, which ultimately lead to cell death and consequently yield losses.

Developing stress-tolerant plants is a strategy that has the potential to solve or mediate at least some of these problems. However, traditional plant breeding strategies to develop new lines of plants that exhibit resistance (tolerance) to these types of stresses are relatively slow and require specific resistant lines for crossing with the desired line. Limited germplasm resources for stress tolerance and incompatibility in crosses between distantly related plant species represent significant problems encountered in conventional breeding. Additionally, the cellular processes leading to drought, cold and salt tolerance in model, drought- and/or salt-tolerant plants are complex in nature and involve multiple mechanisms of cellular adaptation and numerous metabolic pathways. This multi-component nature of stress tolerance has not only made breeding for tolerance largely unsuccessfull, but has also limited the ability to genetically engineer stress tolerance plants using biotechnological methods.

Drought and cold stresses, as well as salt stresses, have a common theme important for plant growth, and that is water availability. Plants are exposed during their entire life cycle to conditions of reduced environmental water content, and most plants have evolved strategies to protect themselves against these conditions of desiccation. However, if the severity and duration of the drought conditions are too great, the effects on plant development, growth and yield of most crop plants are profound. Further-more, most of the crop plants are very susceptible to higher salt concentrations in the soil. Because high salt content in some soils results in less water being available for cell intake, high salt concentration has an effect on plants similar to the effect of drought on plants. Additionally, under freezing temperatures, plant cells lose water as a result of ice formation that starts in the apoplast and withdraws water from the symplast. A plant's molecular response mechanisms to each of these stress conditions are common, and protein phosphatases play an essential role in these molecular mechanisms.

It is well recognized that reversible phosphorylation of proteins controls many cellular processes in plants and animals. The phosphorylation status of proteins is regulated by the opposing activities of protein kinases and protein phosphatases. Phosphorylation of eukaryotic proteins occurs predominantly on serine and threonine residues, and to a lesser extent, on tyrosine residues. In animals, protein phosphorylation plays well-known roles in diverse cellular processes such as glycogen metabolism, cell cycle control, and signal transduction (Smith, R. D. and Walker, J. C., 1996, Annu. Rev. Plant Physiol. Plant Mol. Biol. 47:101–125).

Protein phosphatase activities have been reported in most plant subcellular compartments, including mitochondria, chloroplast, nuclei and the cytosol, and are associated with various membrane and particulate fractions. Some protein phosphatases are poorly characterized and may represent novel enzymes that are unique to plants. Others have biochemical properties that are very similar to well-known mammalian protein phosphatases, such as cytosolic protein serine/threonine phosphatases (MacKintosh C. and Cohen P. 1989 Biochem. J. 262:335–339). Two such plant serine/threonine phosphatases have been identified that function similar to mammalian type-1 (PP1) and type-2 (PP2) protein serine/threonine phosphatases. Biochemical and genetic studies in plants implicate PP1 and/or PP2 activity in signal transduction, hormonal regulation, mitosis, and control of carbon and nitrogen metabolism (Smith, R. D. and Walker, J. C., 1996, Annu. Rev. Plant Physiol. Plant Mol. Biol. 47:101–125).

Experimental evidence has implicated the involvement of protein phosphatases in the plant stress-signaling cascade, and more particularly, in stress perception and signal transduction linked to physiological mechanisms of adaptation in plants. For example, protein phosphatase 2C (PP2C) has been shown to be involved in stress responses in plants (Sheen, J. 1998 Proc. Natl. Acad. Sci. USA 95:975–980). It has also been demonstrated that, in yeast, the PP2B phosphatase calcineurin (CaN) is a focal component of a $Ca^{2+}$-dependent signal transduction pathway that mediates $Na^+$, $Li^-$, and $Mn^{2+}$ tolerance of *Saccharomyces cerevisiae* (Cunningham, K. W. and Fink, G. R. 1996 Mol. Cell. Biol. 16:2226–2237). CaN functions to limit intracellular $Na^+$ accumulation by regulating processes that restrict influx and enhance efflux of this cation across the plasma membrane. CaN also participates in cytosolic $Ca^{2+}$ homeostasis through the positive regulation of Golgi apparatus and vacuolar membrane-localized P-type ion pumps and negative control of a vacuolar $H^+/Ca^{2+}$ exchanger. Interestingly, overexpression of yeast CaN confers salt tolerance in plants, strongly indicating that modulation of stress signaling pathways by expression of an activated protein phosphatase substantially enhances plant stress tolerance (Pardo, J. M. et al. 1998 Proc. Natl. Acad. Sci. USA 95:9681–9686).

Although some genes that are involved in stress responses in plants have been characterized, the characterization and cloning of plant genes that confer stress tolerance remains largely incomplete and fragmented. For example, certain studies have indicated that drought and salt stress in some plants may be due to additive gene effects, in contrast to other research that indicates specific genes are transcriptionally activated in vegetative tissue of plants under osmotic stress conditions. Although it is generally assumed that stress-induced proteins have a role in tolerance, direct evidence is still lacking, and the functions of many stress-responsive genes are unknown.

There is a need, therefore, to identify genes expressed in stress tolerant plants that have the capacity to confer stress resistance to its host plant and to other plant species. Newly generated stress tolerant plants will have many advantages, such as increasing the range in which crop plants can be cultivated by, for example, decreasing the water requirements of a plant species.

SUMMARY OF THE INVENTION

This invention fulfills in part the need to identify new, unique protein phosphatases capable of conferring stress tolerance to plants upon over-expression. The present invention describes a novel genus of Protein Phosphatase Stress-Related Polypeptides (PPSRPs) and PPSRP coding nucleic acids that are important for modulating a plant's response to an environmental stress. More particularly, over-expression of these PPSRP coding nucleic acids in a plant results in the plant's increased tolerance to an environmental stress.

Therefore, the present invention includes an isolated plant cell comprising a PPSRP coding nucleic acid, wherein expression of the nucleic acid sequence in the plant cell results in increased tolerance to environmental stress as compared to a wild type variety of the plant cell. Namely, described herein are Protein Phosphatase 2A-1 (PP2A-1) and Protein Phosphatase-1 (PP-1) from *Physcomitrella patens; Brassica napus* Protein Phosphatase PP2A-1 (BnPP2A-1), BnPP2A-2, and BnPP2A-3 from *Brassica napus; Glycine max* Protein Phosphatase PP2A-1 (GmPP2A-1), GmPP2A-2, GmPP2A-3, GmPP2A-4, and GmPP2A-5 from *Glycine max*; and *Oryza sativa* Protein Phosphatase PP2A-1 (OsPP2A-1), OsPP2A-2, OsPP2A-3, OsPP2A-4, and OsPP2A-5 from *Oryza sativa*.

The invention provides in some embodiments that the PPSRP and coding nucleic acid are those that are found in members of the genuses *Physcomitrella, Brassica, Glycine*, or *Oryza*. In another preferred embodiment, the nucleic acid and polypeptide are from a *Physcomitrella patens*, a *Brassica napus*, a *Glycine max*, or an *Oryza sativa*. The invention provides that the environmental stress can be salinity, drought, temperature, metal, chemical, pathogenic and oxidative stresses, or combinations thereof. In preferred embodiments, the environmental stress can be drought, high salt or cold temperature.

The invention further provides a seed produced by a transgenic plant transformed by a PPSRP coding nucleic acid, wherein the plant is true breeding for increased tolerance to environmental stress as compared to a wild type variety of the plant. The invention further provides a seed produced by a transgenic plant expressing a PPSRP, wherein the plant is true breeding for increased tolerance to environmental stress as compared to a wild type variety of the plant.

The invention further provides an agricultural product produced by any of the below-described transgenic plants, plant parts or seeds. The invention further provides an isolated PPSRP as described below. The invention further provides an isolated PPSRP coding nucleic acid, wherein the PPSRP coding nucleic acid codes for a PPSRP as described below.

The invention further provides an isolated recombinant expression vector comprising a PPSRP coding nucleic acid as described below, wherein expression of the vector in a host cell results in increased tolerance to environmental stress as compared to a wild type variety of the host cell. The invention further provides a host cell containing the vector and a plant containing the host cell.

The invention further provides a method of producing a transgenic plant with a PPSRP coding nucleic acid, wherein expression of the nucleic acid in the plant results in increased tolerance to environmental stress as compared to a wild type variety of the plant comprising: (a) transforming a plant cell with an expression vector comprising a PPSRP coding nucleic acid, and (b) generating from the plant cell a transgenic plant with an increased tolerance to environmental stress as compared to a wild type variety of the plant. In preferred embodiments, the PPSRP and PPSRP coding nucleic acid are as described below.

The present invention further provides a method of identifying a novel PPSRP, comprising (a) raising a specific antibody response to a PPSRP, or fragment thereof, as described below; (b) screening putative PPSRP material with the antibody, wherein specific binding of the antibody to the material indicates the presence of a potentially novel PPSRP; and (c) identifying from the bound material a novel PPSRP in comparison to known PPSRP. Alternatively, hybridization with nucleic acid probes as described below can be used to identify novel PPSRP nucleic acids.

The present invention also provides methods of modifying stress tolerance of a plant comprising, modifying the expression of a PPSRP nucleic acid in the plant, wherein the PPSRP is as described below. The invention provides that this method can be performed such that the stress tolerance is either increased or decreased. Preferably, stress tolerance is increased in a plant via increasing expression of a PPSRP nucleic acid.

BRIEF DESCRIPTION OF THE DRAWINGS

FIG. 2 shows an alignment of the deduced amino acid sequence of PP2A-1 (SEQ ID NO:3) from *Physcomitrella patens* with deduced amino acid sequences of OsPP2A-1 (SEQ ID NO:24), OsPP2A-2 (SEQ ID NO:26), OsPP2A-3 (SEQ ID NO:28), OsPP2A-4 (SEQ ID NO:30), and OsPP2A-5 (SEQ ID NO:32) from *Oryza sativa*. The identical and similar amino acids among SEQ ID NOs: 3, 24, 26, 28, 30 and 32 are shown in Consensus (SEQ ID No:44), FIG. 3 shows an alignment of the deduced amino acid sequence of PP2A-1 (SEQ ID NO:3) from *Physcomitrella patens* with deduced amino acid sequences of GmPP2A-1 (SEQ ID NO:14), GmPP2A-2 (SEQ ID NO:16), GmPP2A-3 (SEQ ID NO:18), GmPP2A-4 (SEQ ID NO:20), and GmPP2A-5 (SEQ ID NO:22) from *Glycine max*; and BnPP2A-1 (SEQ ID NO:8), BnPP2A-2 (SEQ ID NO:10), and BnPP2A-3 (SEQ ID NO:12) from *Brassica napus*. The identical and similar amino acids among SEQ ID NOs: 3, 14, 16, 18, 20, 22, 8, 10 and 12 are shown in Consensus (SEQ ID NO:45).

FIG. 4 shows an alignment of the deduced amino acid sequence of PP2A-1 (SEQ ID NO:3) from *Physcomitrella patens* with deduced amino acid sequences of OsPP2A-1 (SEQ ID NO:24), OsPP2A-2 (SEQ ID NO:26), OsPP2A-3 (SEQ ID NO:28), OsPP2A-4 (SEQ ID NO:30), and OsPP2A-5 (SEQ ID NO:32) from *Oryza sativa*. The alignment also includes GmPP2A-1 (SEQ ID NO:14), GmPP2A-2 (SEQ ID NO:16), GmPP2A-3 (SEQ ID NO:18), GmPP2A-4 (SEQ ID NO:20), and GmPP2A-5 (SEQ ID NO:22) from *Glycine max*; and BnPP2A-1 (SEQ ID NO:8), BnPP2A-2 (SEQ ID NO:10), and BnPP2A-3 (SEQ ID NO:12) from *Brassica napus*. The identical and similar amino acids among SEQ ID NOs: 3, 24, 26, 28, 30, 32, 14, 16, 18, 20, 22, 8, 10 and 12 are shown in Consensus (SEQ ID NO:46).

DETAILED DESCRIPTION OF THE INVENTION

Figure 1:
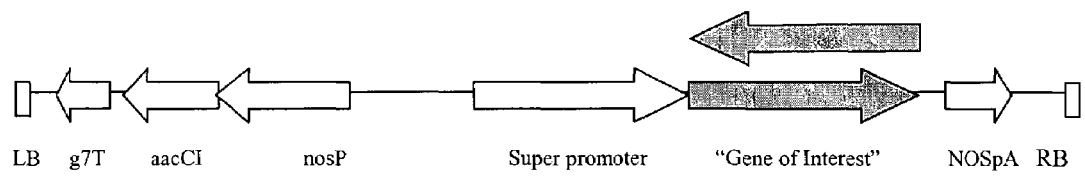
FIG. 1 shows a diagram of the plant expression vector pBPSJH001 containing the super promoter driving the expression of a PPSRP coding nucleic acid ("Gene of Interest"). The components are: aacCI gentamycin resistance gene (Hajdukiewicz et al., Plant Molec. Biol. 25: 989–94, 1994), NOS promoter (Becker et al., Plant Molec. Biol. 20: 1195–97 1992), g7T terminator (Becker et al., 1992), NOSpA terminator (Jefferson et al., EMBO J. 6:3901–7 1987).

The present invention may be understood more readily by reference to the following detailed description of the preferred embodiments of the invention and the Examples included herein. However, before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting. In particular, the designation of the amino acid sequences as polypeptide "Protein Phosphatase Stress-Related Polypeptides" (PPSRPs), in no way limits the functionality of those sequences.

The present invention describes a novel genus of Protein Phosphatase Stress-Related Polypeptides (PPSRPs) and PPSRP coding nucleic acids that are important for modulating a plant's response to an environmental stress. More particularly, over-expression of these PPSRP coding nucleic acids in a plant results in the plant's increased tolerance to an environmental stress. Representative members of the PPSRP genus include, but are not limited to, PP2A-1, PP2A-2, PP2A-3, PP2A-4, PP-1, BnPP2A-1, BnPP2A-2, BnPP2A-3, GmPP2A-1, GmPP2A-2, GmPP2A-3, GmPP2A-4, GmPP2A-5, OsPP2A-1, OsPP2A-2, OsPP2A-3, OsPP2A-4, and OsPP2A-5. In a preferred embodiment, all members of the genus are biologically active protein phosphatases. The PP2A-2, PP2A-3, and PP2A-4 polypeptides are described in U.S. patent application Ser. No. 09/828,302, the entire contents of which are hereby incorporated by reference, while PP2A-1, PP-1, BnPP2A-1, BnPP2A-2, BnPP2A-3, GmPP2A-1, GmPP2A-2, GmPP2A-3, GmPP2A-4, GmPP2A-5, OsPP2A-1, OsPP2A-2, OsPP2A-3, OsPP2A-4, and OsPP2A-5 are described herein.

The present invention provides a transgenic plant cell transformed by a PPSRP coding nucleic acid, wherein expression of the nucleic acid sequence in the plant cell results in increased tolerance to environmental stress as compared to a wild type variety of the plant cell. The invention further provides transgenic plant parts and transgenic plants containing the plant cells described herein. Plant parts include, but are not limited to, stems, roots, ovules, stamens, leaves, embryos, meristematic regions, callus tissue, gametophytes, sporophytes, pollen, microspores and the like. In one embodiment, the transgenic plant is male sterile. Also provided is a plant seed produced by a transgenic plant transformed by a PPSRP coding nucleic acid, wherein the seed contains the PPSRP coding nucleic acid, and wherein the plant is true breeding for increased tolerance to environmental stress as compared to a wild type variety of the plant. The invention further provides a seed produced by a transgenic plant expressing a PPSRP, wherein the seed contains the PPSRP, and wherein the plant is true breeding for increased tolerance to environmental stress as compared to a wild type variety of the plant. The invention also provides an agricultural product produced by any of the below-described transgenic plants, plant parts and plant seeds. Agricultural products include, but are not limited to, plant extracts, proteins, amino acids, carbohydrates, fats, oils, polymers, vitamins, and the like.

As used herein, the term "variety" refers to a group of plants within a species that share constant characters that separate them from the typical form and from other possible varieties within that species. While possessing at least one distinctive trait, a variety is also characterized by some variation between individuals within the variety, based primarily on the Mendelian segregation of traits among the progeny of succeeding generations. A variety is considered "true breeding" for a particular trait if it is genetically homozygous for that trait to the extent that, when the true-breeding variety is self-pollinated, a significant amount of independent segregation of the trait among the progeny is not observed. In the present invention, the trait arises from the transgenic expression of one or more DNA sequences introduced into a plant variety.

The present invention describes for the first time that the *Physcomitrella patens* PPSRPs, PP2A-1 and PP-1; *Brassica napus* PPSRPs, BnPP2A-1, BnPP2A-2, and BnPP2A-3; *Glycine max* PPSRPs, GmPP2A-1, GmPP2A-2, GmPP2A-3, GmPP2A-4, and GmPP2A-5; and *Oryza sativa* PPSRPs, OsPP2A-1, OsPP2A-2, OsPP2A-3, OsPP2A-4, and OsPP2A-5; are useful for increasing a plant's tolerance to environmental stress. As used herein, the term polypeptide refers to a chain of at least four amino acids joined by peptide bonds. The chain may be linear, branched, circular or combinations thereof. Accordingly, the present invention provides isolated PPSRPs selected from the group consisting of PP2A-1, PP-1, BnPP2A-1, BnPP2A-2, BnPP2A-3, GmPP2A-1, GmPP2A-2, GmPP2A-3, GmPP2A-4, GmPP2A-5, OsPP2A-1, OsPP2A-2, OsPP2A-3, OsPP2A-4, and OsPP2A-5, and homologs thereof. In preferred embodiments, the PPSRP is selected from: 1) Protein phosphatase 2A-1 (PP2A-1) polypeptide as defined in SEQ ID NO:3; 2) Protein phosphatase-1 (PP-1) polypeptide as defined in SEQ ID NO:6; 3) *Brassica napus* Protein Phosphatase PP2A-1 (BnPP2A-1) polypeptide as defined in SEQ ID NO:8; 4) BnPP2A-2 polypeptide as defined in SEQ ID NO:10; 5) BnPP2A-3 polypeptide as defined in SEQ ID NO:12; 6) *Glycine max* Protein Phosphatase PP2A-1 (GmPP2A-1) polypeptide as defined in SEQ ID NO:14; 7) GmPP2A-2 polypeptide as defined in SEQ ID NO:16; 8) GmPP2A-3 polypeptide as defined in SEQ ID NO:18; 9) GmPP2A-4 polypeptide as defined in SEQ ID NO:20; 10) GmPP2A-5 polypeptide as defined in SEQ ID NO:22; 11) *Oryza sativa* Protein phosphatase 2A-1 (OsPP2A-1) polypeptide as defined in SEQ ID NO:24; 12) OsPP2A-2 polypeptide as defined in SEQ ID NO:26; 13) OsPP2A-3 polypeptide as defined in SEQ ID NO:28; 14) OsPP2A-4 polypeptide as defined in SEQ ID NO:30; 15) OsPP2A-5 polypeptide as defined in SEQ ID NO:32; and homologs and orthologs thereof. Homologs and orthologs of the amino acid sequences are defined below.

The PPSRPs of the present invention are preferably produced by recombinant DNA techniques. For example, a nucleic acid molecule encoding the polypeptide is cloned into an expression vector (as described below), the expression vector is introduced into a host cell (as described below) and the PPSRP is expressed in the host cell. The PPSRP can then be isolated from the cells by an appropriate purification scheme using standard polypeptide purification techniques. For the purposes of the invention, the term "recombinant polynucleotide" refers to a polynucleotide that has been altered, rearranged or modified by genetic engineering. Examples include any cloned polynucleotide, and polynucleotides that are linked or joined to heterologous sequences. The term "recombinant" does not refer to alterations to polynucleotides that result from naturally occurring events, such as spontaneous mutations. Alternative to recombinant expression, a PPSRP, or peptide can be synthesized chemically using standard peptide synthesis techniques. Moreover, native PPSRP can be isolated from cells (e.g., *Physcomitrella patens, Brassica napus, Glycine max,* or *Oryza sativa*), for example using an anti-PPSRP antibody, which can be produced by standard techniques utilizing a PPSRP or fragment thereof.

The invention further provides an isolated PPSRP coding nucleic acid. The present invention includes PPSRP coding nucleic acids that encode PPSRPs as described herein. In preferred embodiments, the PPSRP coding nucleic acid is selected from: 1) Protein phosphatase 2A-1 (PP2A-1) nucleic acid as defined in SEQ ID NO:2; 2) Protein phosphatase-1 (PP-1) nucleic acid as defined in SEQ ID NO:5; 3) *Brassica napus* Protein Phosphatase PP2A-1 (BnPP2A-1) nucleic acid as defined in SEQ ID NO:7; 4) BnPP2A-2 nucleic acid as defined in SEQ ID NO:9; 5) BnPP2A-3 nucleic acid as defined in SEQ ID NO:11; 6) *Glycine max* Protein Phosphatase PP2A-1 (GmPP2A-1) nucleic acid as defined in SEQ ID NO:13; 7) GmPP2A-2 nucleic acid as defined in SEQ ID NO:15; 8) GmPP2A-3 nucleic acid as defined in SEQ ID NO:17; 9) GmPP2A-4 nucleic acid as defined in SEQ ID NO:19; 10) GmPP2A-5 nucleic acid as defined in SEQ ID NO:21; 11) *Oryza sativa* Protein phosphatase 2A-1 (OsPP2A-1) nucleic acid as defined in SEQ ID NO:23; 12) OsPP2A-2 nucleic acid as defined in SEQ ID NO:25; 13) OsPP2A-3 nucleic acid as defined in SEQ ID NO:27; 14) OsPP2A-4 nucleic acid as defined in SEQ ID NO:29; 15) OsPP2A-5 nucleic acid as defined in SEQ ID NO:31; and homologs and orthologs thereof. Homologs and orthologs of the nucleotide sequences are defined below. In one preferred embodiment, the nucleic acid and polypeptide are isolated from the plant genus *Physcomitrella, Brassica, Glycine,* or *Oryza*. In another preferred embodiment, the nucleic acid and polypeptide are from a *Physcomitrella patens (P. patens)* plant, a *Brassica napus* plant, a *Glycine max* plant, or an *Oryza sativa* plant.

As used herein, the term "environmental stress" refers to any sub-optimal growing condition and includes, but is not limited to, sub-optimal conditions associated with salinity, drought, temperature, metal, chemical, pathogenic and oxidative stresses, or combinations thereof. In preferred embodiments, the environmental stress can be salinity, drought, or temperature, or combinations thereof, and in particular, can be high salinity, low water content or low temperature. It is also to be understood that as used in the specification and in the claims, "a" or "an" can mean one or more, depending upon the context in which it is used. Thus, for example, reference to "a cell" can mean that at least one cell can be utilized.

As also used herein, the term "nucleic acid" and "polynucleotide" refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine and others can also be used for antisense, dsRNA and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR and in vitro or in vivo transcription.

An "isolated" nucleic acid molecule is one that is substantially separated from other nucleic acid molecules that are present in the natural source of the nucleic acid (i.e., sequences encoding other polypeptides). Preferably, an "isolated" nucleic acid is free of some of the sequences that naturally flank the nucleic acid (i.e., sequences located at the 5' and 3' ends of the nucleic acid) in its naturally occurring replicon. For example, a cloned nucleic acid is considered isolated. In various embodiments, the isolated PPSRP nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a *Physcomitrella patens*, a *Brassica napus*, a *Glycine max*, or an *Oryza sativa* cell). A nucleic acid is also considered isolated if it has been altered by human intervention, or placed in a locus or location that is not its natural site, or if it is introduced into a cell by agroinfection. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

Specifically excluded from the definition of "isolated nucleic acids" are: naturally-occurring chromosomes (such as chromosome spreads), artificial chromosome libraries, genomic libraries, and cDNA libraries that exist either as an in vitro nucleic acid preparations or as a transfected/transformed host cell preparation, wherein the host cells are either an in vitro heterogeneous preparation or plated as a heterogeneous population of single colonies. Also specifically excluded are the above libraries wherein a specified nucleic acid makes up less than 5% of the number of nucleic acid inserts in the vector molecules. Further specifically excluded are whole cell genomic DNA or whole cell RNA preparations (including whole cell preparations that are mechanically sheared or enzymatically digested). Even further specifically excluded are the whole cell preparations found as either an in vitro preparation or as a heterogeneous mixture separated by electrophoresis wherein the nucleic acid of the invention has not further been separated from the heterologous nucleic acids in the electrophoresis medium (e.g., further separating by excising a single band from a heterogeneous band population in an agarose gel or nylon blot).

A nucleic acid molecule of the present invention, e.g., a nucleic acid molecule having a nucleotide sequence of SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31, or a portion thereof, can be isolated using standard molecular biology techniques and the sequence information provided herein. For example, a *P. patens* PPSRP cDNA can be isolated from a *P. patens* library using all or portion of one of the sequences of SEQ ID NO:1 and SEQ ID NO:4. Moreover, a nucleic acid molecule encompassing all or a portion of one of the sequences of SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31 can be isolated by the polymerase chain reaction using oligonucleotide primers designed based upon this sequence. For example, mRNA can be isolated from plant cells (e.g., by the guanidinium-thiocyanate extraction procedure of Chirgwin et al., 1979 Biochemistry 18:5294–5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to a PPSRP nucleotide sequence can be prepared by standard synthetic techniques, e.g., using an automated DNA synthesizer.

In a preferred embodiment, an isolated nucleic acid molecule of the invention comprises one of the nucleotide sequences shown in SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31. These cDNAs comprise sequences encoding the PPSRPs, (i.e., the "coding region"), as well as 5' untranslated sequences and 3' untranslated sequences. It is to be understood that SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31 may comprise both coding regions and 5' and 3' untranslated regions. Alternatively, the nucleic acid molecules of the present invention can comprise only the coding region of any of the sequences in SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31, or can contain whole genomic fragments isolated from genomic DNA. The present invention also includes PPSRP coding nucleic acids that encode PPSRPs as described herein. Preferred is a PPSRP coding nucleic acid that encodes a PPSRP selected from the group consisting of PP2A-1 (SEQ ID NO:3), PP-1 (SEQ ID NO:6), BnPP2A-1 (SEQ ID NO:8), BnPP2A-2 (SEQ ID NO:10), BnPP2A-3 (SEQ ID NO:12), GmPP2A-1 (SEQ ID NO:14), GmPP2A-2 (SEQ ID NO:16), GmPP2A-3 (SEQ ID NO:18), GmPP2A-4 (SEQ ID NO:20), GmPP2A-4 (SEQ ID NO:22), OsPP2A-1 (SEQ ID NO:24), OsPP2A-2 (SEQ ID NO:26), OsPP2A-3 (SEQ ID NO:28), OsPP2A-4 (SEQ ID NO:30), and OsPP2A-5 (SEQ ID NO:32).

Moreover, the nucleic acid molecule of the invention can comprise only a portion of the coding region of one of the sequences in SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31, for example, a fragment that can be used as a probe or primer or a fragment encoding a biologically active portion of a PPSRP. The nucleotide sequences determined from the cloning of the PPSRP genes from *P. patens, B. napus, G. max,* and *O. sativa* allow for the generation of probes and primers designed for use in identifying and/or cloning PPSRP homologs in other cell types and organisms, as well as PPSRP homologs from other mosses and related species. The portion of the coding region can also encode a biologically active fragment of a PPSRP.

As used herein, the term "biologically active portion of" a PPSRP is intended to include a portion, e.g., a domain/motif, of a PPSRP that participates in modulation of stress tolerance in a plant, and more preferably, drought tolerance or salt tolerance. For the purposes of the present invention, modulation of stress tolerance refers to at least a 10% increase or decrease in the stress tolerance of a transgenic plant comprising a PPSRP expression cassette (or expression vector) as compared to the stress tolerance of a non-transgenic control plant. Methods for quantitating stress tolerance are provided at least in Example 7 below. In a preferred embodiment, the biologically active portion of a PPSRP increases a plant's tolerance to an environmental stress.

Biologically active portions of a PPSRP include peptides comprising amino acid sequences derived from the amino acid sequence of a PPSRP (e.g., an amino acid sequence of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, and SEQ ID NO:32) or the amino acid sequence of a polypeptide identical to a PPSRP, which include fewer amino acids than a full length PPSRP or the full length polypeptide which is identical to a PPSRP, and exhibit at least one activity of a PPSRP. Typically, biologically active portions (e.g., peptides which are, for example, 5, 10, 15, 20, 30, 35, 36, 37, 38, 39, 40, 50, 100 or more amino acids in length) comprise a domain or motif with at least one activity of a PPSRP. Moreover, other biologically active portions in which other regions of the polypeptide are deleted, can be prepared by recombinant techniques and evaluated for one or more of the activities described herein. Preferably, the biologically active portions of a PPSRP include one or more selected domains/motifs or portions thereof having biological activity.

The invention also provides PPSRP chimeric or fusion polypeptides. As used herein, a PPSRP "chimeric polypeptide" or "fusion polypeptide" comprises a PPSRP operatively linked to a non-PPSRP. A PPSRP refers to a polypeptide having an amino acid sequence corresponding to a PPSRP, whereas a non-PPSRP refers to a polypeptide having an amino acid sequence corresponding to a polypeptide which is not substantially identical to the PPSRP, e.g., a polypeptide that is different from the PPSRP and is derived from the same or a different organism. Within the fusion polypeptide, the term "operatively linked" is intended to indicate that the PPSRP and the non-PPSRP are fused to each other so that both sequences fulfill the proposed function attributed to the sequence used. The non-PPSRP can be fused to the N-terminus or C-terminus of the PPSRP. For example, in one embodiment, the fusion polypeptide is a GST-PPSRP fusion polypeptide in which the PPSRP sequences are fused to the C-terminus of the GST sequences. Such fusion polypeptides can facilitate the purification of recombinant PPSRPs. In another embodiment, the fusion polypeptide is a PPSRP containing a heterologous signal sequence at its N-terminus. In certain host cells (e.g., mammalian host cells), expression and/or secretion of a PPSRP can be increased through use of a heterologous signal sequence.

Preferably, a PPSRP chimeric or fusion polypeptide of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and re-amplified to generate a chimeric gene sequence (see, for example, Current Protocols in Molecular Biology, Eds. Ausubel et al. John Wiley & Sons: 1992). Moreover, many expression vectors are commercially available that already encode a fusion moiety (e.g., a GST polypeptide). A PPSRP encoding nucleic acid can be cloned into such an expression vector such that the fusion moiety is linked in-frame to the PPSRP.

In addition to fragments and fusion polypeptides of the PPSRPs described herein, the present invention includes homologs and analogs of naturally occurring PPSRPs and PPSRP encoding nucleic acids in a plant. "Homologs" are defined herein as two nucleic acids or polypeptides that have similar, or "identical," nucleotide or amino acid sequences, respectively. Homologs include allelic variants, orthologs, paralogs, agonists and antagonists of PPSRPs as defined hereafter. The term "homolog" further encompasses nucleic acid molecules that differ from one of the nucleotide sequences shown in SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31 (and portions thereof) due to degeneracy of the genetic code and thus encode the same PPSRP as that encoded by the nucleotide sequences shown in SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31. As used herein a "naturally occurring" PPSRP refers to a PPSRP amino acid sequence that occurs in nature. Preferably, a naturally occurring PPSRP comprises an amino acid sequence selected from the group consisting of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, and SEQ ID NO:32.

An agonist of the PPSRP can retain substantially the same, or a subset, of the biological activities of the PPSRP. An antagonist of the PPSRP can inhibit one or more of the activities of the naturally occurring form of the PPSRP. For example, the PPSRP antagonist can competitively bind to a downstream or upstream member of the cell membrane component metabolic cascade that includes the PPSRP, or bind to a PPSRP that mediates transport of compounds across such membranes, thereby preventing translocation from taking place.

Nucleic acid molecules corresponding to natural allelic variants and analogs, orthologs, and paralogs of a PPSRP cDNA can be isolated based on their identity to the *Physcomitrella patens*, *Brassica napus*, *Glycine max*, or *Oryza sativa* PPSRP nucleic acids described herein using PPSRP cDNAs, or a portion thereof, as a hybridization probe according to standard hybridization techniques under stringent hybridization conditions. In an alternative embodiment, homologs of the PPSRP can be identified by screening combinatorial libraries of mutants, e.g., truncation mutants, of the PPSRP for PPSRP agonist or antagonist activity. In one embodiment, a variegated library of PPSRP variants is generated by combinatorial mutagenesis at the nucleic acid level and is encoded by a variegated gene library. A variegated library of PPSRP variants can be produced by, for example, enzymatically ligating a mixture of synthetic oligonucleotides into gene sequences such that a degenerate set of potential PPSRP sequences is expressible as individual polypeptides, or alternatively, as a set of larger fusion polypeptides (e.g., for phage display) containing the set of PPSRP sequences therein. There are a variety of methods that can be used to produce libraries of potential PPSRP homologs from a degenerate oligonucleotide sequence. Chemical synthesis of a degenerate gene sequence can be performed in an automatic DNA synthesizer, and the synthetic gene is then ligated into an appropriate expression vector. Use of a degenerate set of genes allows for the provision, in one mixture, of all of the sequences encoding the desired set of potential PPSRP sequences. Methods for synthesizing degenerate oligonucleotides are known in the art (see, e.g., Narang, S. A., 1983 Tetrahedron 39:3; Itakura et al., 1984 Annu. Rev. Biochem. 53:323; Itakura et al., 1984 Science 198:1056; Ike et al., 1983 Nucleic Acid Res. 11:477).

In addition, libraries of fragments of the PPSRP coding regions can be used to generate a variegated population of PPSRP fragments for screening and subsequent selection of homologs of a PPSRP. In one embodiment, a library of coding sequence fragments can be generated by treating a double stranded PCR fragment of a PPSRP coding sequence with a nuclease under conditions wherein nicking occurs only about once per molecule, denaturing the double stranded DNA, renaturing the DNA to form double stranded DNA, which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the PPSRP.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of PPSRP homologs. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify PPSRP homologs (Arkin and Yourvan, 1992 PNAS 89:7811–7815; Delgrave et al., 1993 Polypeptide Engineering 6(3):327–331). In another embodiment, cell based assays can be exploited to analyze a variegated PPSRP library, using methods well known in the art. The present invention further provides a method of identifying a novel PPSRP, comprising (a) raising a specific antibody response to a PPSRP, or a fragment thereof, as described herein; (b) screening putative PPSRP material with the antibody, wherein specific binding of the antibody to the material indicates the presence of a potentially novel PPSRP; and (c) analyzing the bound material in comparison to a known PPSRP, to determine its novelty.

As stated above, the present invention includes PPSRPs and homologs thereof. To determine the percent sequence identity of two amino acid sequences (e.g., one of the sequences of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, and SEQ ID NO:32, and a mutant form thereof), the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence (e.g., one of the sequences of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, and SEQ ID NO:32) is occupied by the same amino acid residue as the corresponding position in the other sequence (e.g., a mutant form of the sequence selected from the polypeptide of SEQ ID NO:3, SEQ ID NO:6, SEQ ID NO:8, SEQ NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, and SEQ ID NO:32), then the molecules are identical at that position. The same type of comparison can be made between two nucleic acid sequences.

The percent sequence identity between the two sequences is a function of the number of identical positions shared by the sequences (i.e., percent sequence identity=numbers of identical positions/total numbers of positions×100). Preferably, the isolated amino acid homologs included in the present invention are at least about 50–60%, preferably at least about 60–70%, and more preferably at least about 70–75%, 75–80%, 80–85%, 85–90% or 90–95%, and most preferably at least about 96%, 97%, 98%, 99% or more identical to an entire amino acid sequence shown in SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, and SEQ ID NO:32. In yet another embodiment, the isolated amino acid homologs included in the present invention are at least about 50–60%, preferably at least about 60–70%, and more preferably at least about 70–75%, 75–80%, 80–85%, 85–90% or 90–95%, and most preferably at least about 96%, 97%, 98%, 99% or more identical to an entire amino acid sequence encoded by a nucleic acid sequence shown in SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31. In other embodiments, the PPSRP amino acid homologs have sequence identity over at least 15 contiguous amino acid residues, more preferably at least 25 contiguous amino acid residues, and most preferably at least 35 contiguous amino acid residues of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32.

In another preferred embodiment, an isolated nucleic acid homolog of the invention comprises a nucleotide sequence which is at least about 50–60%, preferably at least about 60–70%, more preferably at least about 70–75%, 75–80%, 80–85%, 85–90% or 90–95%, and even more preferably at least about 95%, 96%, 97%, 98%, 99% or more identical to a nucleotide sequence shown in SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31, or to a portion comprising at least 60 consecutive nucleotides thereof. The preferable length of sequence comparison for nucleic acids is at least 75 nucleotides, more preferably at least 100 nucleotides and most preferably the entire length of the coding region.

It is further preferred that the isolated nucleic acid homolog of the invention encodes a PPSRP, or portion thereof, that is at least 70% identical to an amino acid sequence of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32, and that functions as a modulator of an environmental stress response in a plant. In a more preferred embodiment, overexpression of the nucleic acid homolog in a plant increases the tolerance of the plant to an environmental stress. In a further preferred embodiment, the nucleic acid homolog encodes a PPSRP that functions as a protein phosphatase.

For the purposes of the invention, the percent sequence identity between two nucleic acid or polypeptide sequences is determined using the Vector NTI 6.0 (PC) software package (InforMax, 7600 Wisconsin Ave., Bethesda, Md. 20814). A gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. All other parameters are set at the default settings. For purposes of a multiple alignment (Clustal W algorithm), the gap opening penalty is 10, and the gap extension penalty is 0.05 with blosum62 matrix. It is to be understood that for the purposes of determining sequence identity when comparing a DNA sequence to an RNA sequence, a thymidine nucleotide is equivalent to a uracil nucleotide.

In another aspect, the invention provides an isolated nucleic acid comprising a polynucleotide that hybridizes to the polynucleotide of SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31 under stringent conditions. More particularly, an isolated nucleic acid molecule of the invention is at least 15 nucleotides in length and hybridizes under stringent conditions to the nucleic acid molecule comprising a nucleotide sequence of SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31. In other embodiments, the nucleic acid is at least 30, 50, 100, 250 or more nucleotides in length. Preferably, an isolated nucleic acid homolog of the invention comprises a nucleotide sequence which hybridizes under highly stringent conditions to the nucleotide sequence shown in SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31 and functions as a modulator of stress tolerance in a plant. In a further preferred embodiment, over expression of the isolated nucleic acid homolog in a plant increases a plant's tolerance to an environmental stress. In an even further preferred embodiment, the isolated nucleic acid homolog encodes a PPSRP that functions as a protein phosphatase.

As used herein with regard to hybridization for DNA to DNA blot, the term "stringent conditions" refers to hybridization overnight at 60° C. in 10× Denhart's solution, 6×SSC, 0.5% SDS and 100 μg/ml denatured salmon sperm DNA. Blots are washed sequentially at 62° C. for 30 minutes each time in 3×SSC/0.1% SDS, followed by 1×SSC/0.1% SDS and finally 0.1×SSC/0.1% SDS. As also used herein, "highly stringent conditions" refers to hybridization overnight at 65° C. in 10× Denhart's solution, 6×SSC, 0.5% SDS and 100 μg/ml denatured salmon sperm DNA. Blots are washed sequentially at 65° C. for 30 minutes each time in 3×SSC/0.1% SDS, followed by 1×SSC/0.1% SDS and finally 0.1×SSC/0.1% SDS. Methods for nucleic acid hybridizations are described in Meinkoth and Wahl (1984) Anal. Biochem. 138:267–284; Current Protocols in Molecular Biology, Chapter 2, Ausubel et al. Eds., Greene Publishing and Wiley-Interscience, New York, 1995; and Tijssen, Laboratory Techniques in Biochemistry and Molecular Biology: Hybridization with Nucleic Acid Probes, Part I, Chapter 2, Elsevier, N.Y., 1993. Preferably, an isolated nucleic acid molecule of the invention that hybridizes under stringent or highly stringent conditions to a sequence of SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31 corresponds to a naturally occurring nucleic acid molecule. As used herein, a "naturally occurring" nucleic acid molecule refers to an RNA or DNA molecule having a nucleotide sequence that occurs in nature (e.g., encodes a natural polypeptide). In one embodiment, the nucleic acid encodes a naturally occurring *Physcomitrella patens* PPSRP, *Brassica napus* PPSRP, *Glycine max* PPSRP, or *Oryza sativa* PPSRP.

Using the above-described methods, and others known to those of skill in the art, one of ordinary skill in the art can isolate homologs of the PPSRPs comprising amino acid sequences shown in SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32. One subset of these homologs is allelic variants. As used herein, the term "allelic variant" refers to a nucleotide sequence containing polymorphisms that lead to changes in the amino acid sequences of a PPSRP and that exist within a natural population (e.g., a plant species or variety). Such natural allelic variations can typically result in 1–5% variance in a PPSRP nucleic acid. Allelic variants can be identified by sequencing the nucleic acid sequence of interest in a number of different plants, which can be readily carried out by using hybridization probes to identify the same PPSRP genetic locus in those plants. Any and all such nucleic acid variations and resulting amino acid polymorphisms or variations in a PPSRP that are the result of natural allelic variation and that do not alter the functional activity of a PPSRP, are intended to be within the scope of the invention.

Moreover, nucleic acid molecules encoding PPSRPs from the same or other species such as PPSRP analogs, orthologs and paralogs, are intended to be within the scope of the present invention. As used herein, the term "analogs" refers to two nucleic acids that have the same or similar function, but that have evolved separately in unrelated organisms. As used herein, the term "orthologs" refers to two nucleic acids from different species, but that have evolved from a common ancestral gene by speciation. Normally, orthologs encode polypeptides having the same or similar functions. As also used herein, the term "paralogs" refers to two nucleic acids that are related by duplication within a genome. Paralogs usually have different functions, but these functions may be related (Tatusov, R. L. et al. 1997 Science 278(5338): 631–637). Analogs, orthologs and paralogs of a naturally occurring PPSRP can differ from the naturally occurring PPSRP by post-translational modifications, by amino acid sequence differences, or by both. Post-translational modifications include in vivo and in vitro chemical derivatization of polypeptides, e.g., acetylation, carboxylation, phosphorylation, or glycosylation, and such modifications may occur during polypeptide synthesis or processing or following treatment with isolated modifying enzymes. In particular, orthologs of the invention will generally exhibit at least 80–85%, more preferably, 85–90% or 90–95%, and most preferably 95%, 96%, 97%, 98% or even 99% identity or sequence identity with all or part of a naturally occurring PPSRP amino acid sequence and will exhibit a function similar to a PPSRP. Preferably, a PPSRP ortholog of the present invention functions as a modulator of an environmental stress response in a plant and/or functions as a protein phosphatase. More preferably, a PPSRP ortholog increases the stress tolerance of a plant. In one embodiment, the PPSRP orthologs maintain the ability to participate in the metabolism of compounds necessary for the construction of cellular membranes in a plant, or in the transport of molecules across these membranes.

In addition to naturally-occurring variants of a PPSRP sequence that may exist in the population, the skilled artisan will further appreciate that changes can be introduced by mutation into a nucleotide sequence of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32, thereby leading to changes in the amino acid sequence of the encoded PPSRP, without altering the functional activity of the PPSRP. For example, nucleotide substitutions leading to amino acid substitutions at "non-essential" amino acid residues can be made in a sequence of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32. A "non-essential" amino acid residue is a residue that can be altered from the wild-type sequence of one of the PPSRPs without altering the activity of said PPSRP, whereas an "essential" amino acid residue is required for PPSRP activity. Other amino acid residues, however, (e.g., those that are not conserved or only semi-conserved in the domain having PPSRP activity) may not be essential for activity and thus are likely to be amenable to alteration without altering PPSRP activity.

Accordingly, another aspect of the invention pertains to nucleic acid molecules encoding PPSRPs that contain changes in amino acid residues that are not essential for PPSRP activity. Such PPSRPs differ in amino acid sequence from a sequence contained in SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32, yet retain at least one of the PPSRP activities described herein. In one embodiment, the isolated nucleic acid molecule comprises a nucleotide sequence encoding a polypeptide, wherein the polypeptide comprises an amino acid sequence at least about 50% identical to an amino acid sequence of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32. Preferably, the polypeptide encoded by the nucleic acid molecule is at least about 50–60% identical to one of the sequences of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, and SEQ ID NO:32; more preferably at least about 60–70% identical to one of the sequences of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, and SEQ ID NO:32; even more preferably at least about 70–75%, 75–80%, 80–85%, 85–90%, 90–95% identical to one of the sequences of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, and SEQ ID NO:32; and most preferably at least about 96%, 97%, 98%, or 99% identical to one of the sequences of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, and SEQ ID NO:32. The preferred PPSRP homologs of the present invention preferably participate in the a stress tolerance response in a plant, or more particularly, participate in the transcription of a polypeptide involved in a stress tolerance response in a plant, and/or function as a protein phosphatase.

An isolated nucleic acid molecule encoding a PPSRP having sequence identity with a polypeptide sequence of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32 can be created by introducing one or more nucleotide substitutions, additions or deletions into a nucleotide sequence of SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31, respectively, such that one or more amino acid substitutions, additions or deletions are introduced into the encoded polypeptide. Mutations can be introduced into one of the sequences of SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31 by standard techniques, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with an amino acid residue having a similar side chain.

Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a PPSRP is preferably replaced with another amino acid residue from the same side chain family. Alternatively, in another embodiment, mutations can be introduced randomly along all or part of a PPSRP coding sequence, such as by saturation mutagenesis, and the resultant mutants can be screened for a PPSRP activity described herein to identify mutants that retain PPSRP activity. Following mutagenesis of one of the sequences of SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31, the encoded polypeptide can be expressed recombinantly and the activity of the polypeptide can be determined by analyzing the stress tolerance of a plant expressing the polypeptide as described in Example 7.

Additionally, optimized PPSRP nucleic acids can be created. Preferably, an optimized PPSRP nucleic acid encodes a PPSRP that binds to a phosphate group and/or modulates a plant's tolerance to an environmental stress, and more preferably increases a plant's tolerance to an environmental stress upon its over-expression in the plant. As used herein, "optimized" refers to a nucleic acid that is genetically engineered to increase its expression in a given plant or animal. To provide plant optimized PPSRP nucleic acids, the DNA sequence of the gene can be modified to 1) comprise codons preferred by highly expressed plant genes; 2) comprise an A+T content in nucleotide base composition to that substantially found in plants; 3) form a plant initiation sequence, 4) to eliminate sequences that cause destabilization, inappropriate polyadenylation, degradation and termination of RNA, or that form secondary structure hairpins or RNA splice sites. Increased expression of PPSRP nucleic acids in plants can be achieved by utilizing the distribution frequency of codon usage in plants in general or a particular plant. Methods for optimizing nucleic acid expression in plants can be found in EPA 0359472; EPA 0385962; WO 91/16432; U.S. Pat. No. 5,380,831; U.S. Pat. No. 5,436,391; Perlack et al. (1991) Proc. Natl. Acad. Sci. USA 88:3324–3328; and Murray et al. (1989) Nucleic Acids Res. 17:477–498.

As used herein, "frequency of preferred codon usage" refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell. It is preferable that this analysis be limited to genes that are highly expressed by the host cell. The percent deviation of the frequency of preferred codon usage for a synthetic gene from that employed by a host cell is calculated first by determining the percent deviation of the frequency of usage of a single codon from that of the host cell followed by obtaining the average deviation over all codons. As defined herein, this calculation includes unique codons (i.e., ATG and TGG). In general terms, the overall average deviation of the codon usage of an optimized gene from that of a host cell is calculated using the equation $1A = n = 1 \ Z \ X_n - Y_n \ X_n$ times 100 Z where $X_n$=frequency of usage for codon n in the host cell; $Y_n$=frequency of usage for codon n in the synthetic gene, n represents an individual codon that specifies an amino acid and the total number of codons is Z. The overall deviation of the frequency of codon usage, A, for all amino acids should preferably be less than about 25%, and more preferably less than about 10%.

Hence, a PPSRP nucleic acid can be optimized such that its distribution frequency of codon usage deviates, preferably, no more than 25% from that of highly expressed plant genes and, more preferably, no more than about 10%. In addition, consideration is given to the percentage G+C content of the degenerate third base (monocotyledons appear to favor G+C in this position, whereas dicotyledons do not). It is also recognized that the XCG (where X is A, T, C, or G) nucleotide is the least preferred codon in dicots whereas the XTA codon is avoided in both monocots and dicots. Optimized PPSRP nucleic acids of this invention also preferably have CG and TA doublet avoidance indices closely approximating those of the chosen host plant (i.e., *Physcomitrella patens, Brassica napus, Glycine max*, or *Oryza sativa*). More preferably these indices deviate from that of the host by no more than about 10–15%.

In addition to the nucleic acid molecules encoding the PPSRPs described above, another aspect of the invention pertains to isolated nucleic acid molecules that are antisense thereto. Antisense polynucleotides are thought to inhibit gene expression of a target polynucleotide by specifically binding the target polynucleotide and interfering with transcription, splicing, transport, translation and/or stability of the target polynucleotide. Methods are described in the prior art for targeting the antisense polynucleotide to the chromosomal DNA, to a primary RNA transcript or to a processed mRNA. Preferably, the target regions include splice sites, translation initiation codons, translation termination codons, and other sequences within the open reading frame.

The term "antisense", for the purposes of the invention, refers to a nucleic acid comprising a polynucleotide that is sufficiently complementary to all or a portion of a gene, primary transcript or processed mRNA, so as to interfere with expression of the endogenous gene. "Complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other. The term "antisense nucleic acid" includes single stranded RNA as well as double-stranded DNA expression cassettes that can be transcribed to produce an antisense RNA. "Active" antisense nucleic acids are antisense RNA molecules that are capable of selectively hybridizing with a primary transcript or mRNA encoding a polypeptide having at least 80% sequence identity with the polypeptide of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, and SEQ ID NO:32.

The antisense nucleic acid can be complementary to an entire PPSRP coding strand, or to only a portion thereof. In one embodiment, an antisense nucleic acid molecule is antisense to a "coding region" of the coding strand of a nucleotide sequence encoding a PPSRP. The term "coding region" refers to the region of the nucleotide sequence comprising codons that are translated into amino acid residues. In another embodiment, the antisense nucleic acid molecule is antisense to a "noncoding region" of the coding strand of a nucleotide sequence encoding a PPSRP. The term "noncoding region" refers to 5' and 3' sequences that flank the coding region that are not translated into amino acids (i.e., also referred to as 5' and 3' untranslated regions). The antisense nucleic acid molecule can be complementary to the entire coding region of PPSRP mRNA, but more preferably is an oligonucleotide that is antisense to only a portion of the coding or noncoding region of PPSRP mRNA. For example, the antisense oligonucleotide can be complementary to the region surrounding the translation start site of PPSRP mRNA. An antisense oligonucleotide can be, for example, about 5, 10, 15, 20, 25, 30, 35, 40, 45 or 50 nucleotides in length. Typically, the antisense molecules of the present invention comprise an RNA having 60–100% sequence identity with at least 14 consecutive nucleotides of SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31; or a polynucleotide encoding a polypeptide of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32. Preferably, the sequence identity will be at least 70%, more preferably at least 75%, 80%, 85%, 90%, 95%, 98% and most preferably 99%.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., 1987 Nucleic Acids. Res. 15:6625–6641). The antisense nucleic acid molecule can also comprise a 2'-o-methylribonucleotide (Inoue et al., 1987 Nucleic Acids Res. 15:6131–6148) or a chimeric RNA-DNA analogue (Inoue et al., 1987 FEBS Lett. 215: 327–330).

The antisense nucleic acid molecules of the invention are typically administered to a cell or generated in situ such that they hybridize with or bind to cellular mRNA and/or genomic DNA encoding a PPSRP to thereby inhibit expression of the polypeptide, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic (including plant) promoter are preferred.

As an alternative to antisense polynucleotides, ribozymes, sense polynucleotides or double stranded RNA (dsRNA) can be used to reduce expression of a PPSRP polypeptide. By "ribozyme" is meant a catalytic RNA-based enzyme with ribonuclease activity, which is capable of cleaving a single-stranded nucleic acid, such as an mRNA, to which it has a complementary region. Ribozymes (e.g., hammerhead ribozymes described in Haselhoff and Gerlach, 1988 Nature 334:585–591) can be used to catalytically cleave PPSRP mRNA transcripts to thereby inhibit translation of PPSRP mRNA. A ribozyme having specificity for a PPSRP-encoding nucleic acid can be designed based upon the nucleotide sequence of a PPSRP cDNA, as disclosed herein (i.e., SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31), or on the basis of a heterologous sequence to be isolated according to methods taught in this invention. For example, a derivative of a Tetrahymena L-19 IVS RNA can be constructed in which the nucleotide sequence of the active site is complementary to the nucleotide sequence to be cleaved in a PPSRP-encoding mRNA. See, e.g., Cech et al. U.S. Pat. No. 4,987,071 and Cech et al. U.S. Pat. No. 5,116,742. Alternatively, PPSRP mRNA can be used to select a catalytic RNA having a specific ribonuclease activity from a pool of RNA molecules. See, e.g., Bartel, D. and Szostak, J. W., 1993 Science 261:1411–1418. In preferred embodiments, the ribozyme will contain a portion having at least 7, 8, 9, 10, 12, 14, 16, 18 or 20 nucleotides, and more preferably 7 or 8 nucleotides, that have 100% complementarity to a portion of the target RNA. Methods for making ribozymes are known to those skilled in the art. See, for example, U.S. Pat. Nos. 6,025,167; 5,773,260 and 5,496,698.

The term "dsRNA", as used herein, refers to RNA hybrids comprising two strands of RNA. The dsRNAs can be linear or circular in structure. In a preferred embodiment, dsRNA is specific for a polynucleotide encoding either the polypeptide of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32; or a polypeptide having at least 80% sequence identity with SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32. The hybridizing RNAs may be substantially or completely complementary. By "substantially complementary", is meant that when the two hybridizing RNAs are optimally aligned using the BLAST program as described above, the hybridizing portions are at least 95% complementary. Preferably, the dsRNA will be at least 100 base pairs in length. Typically, the hybridizing RNAs will be of identical length with no over hanging 5' or 3' ends and no gaps. However, dsRNAs having 5' or 3' overhangs of up to 100 nucleotides may be used in the methods of the invention.

The dsRNA may comprise ribonucleotides or ribonucleotide analogs, such as 2'-O-methyl ribosyl residues or combinations thereof. See U.S. Pat. Nos. 4,130,641 and 4,024,222. A dsRNA polyriboinosinic acid:polyribocytidylic acid is described in U.S. Pat. No. 4,283,393. Methods for making and using dsRNA are known in the art. One method comprises the simultaneous transcription of two complementary DNA strands, either in vivo, or in a single in vitro reaction mixture. See, for example, U.S. Pat. No. 5,795,715. dsRNA can be introduced into a plant or plant cell directly by standard transformation procedures. Alternatively, dsRNA can be expressed in a plant cell by transcribing two complementary RNAs.

Other methods for the inhibition of endogenous gene expression, such as triple helix formation (Moser et. al (1987) *Science* 238:645–650 and Cooney et al. (1988) *Science* 241:456–459) and cosuppression (Napoli et al. (1990) *The Plant Cell* 2:279–289) are known in the art. Partial and full-length cDNAs have been used for the cosuppression of endogenous plant genes. See, for example, U.S. Pat. Nos. 4,801,340, 5,034,323, 5,231,020 and 5,283,184, Van der Kroll et al. (1990) *The Plant Cell* 2:291–299, Smith et al. (1990) *Mol Gen Genetics* 224:477–481 and Napoli et al. (1990) *The Plant Cell* 2:279–289.

For sense suppression, it is believed that introduction of a sense polynucleotide blocks transcription of the corresponding target gene. The sense polynucleotide will have at least 65% sequence identity with the target plant gene or RNA. Preferably, the percent identity is at least 80%, 90%, 95% or more. The introduced sense polynucleotide need not be full length relative to the target gene or transcript. Preferably, the sense polynucleotide will have at least 65% sequence identity with at least 100 consecutive nucleotides of SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31. The regions of identity can comprise introns and and/or exons and untranslated regions. The introduced sense polynucleotide may be present in the plant cell transiently, or may be stably integrated into a plant chromosome or extrachromosomal replicon.

Alternatively, PPSRP gene expression can be inhibited by targeting nucleotide sequences complementary to the regulatory region of a PPSRP nucleotide sequence (e.g., a PPSRP promoter and/or enhancer) to form triple helical structures that prevent transcription of a PPSRP gene in target cells. See generally, Helene, C., 1991 Anticancer Drug Des. 6(6): 569–84; Helene, C. et al., 1992 Ann. N.Y. Acad. Sci. 660:27–36; and Maher, L. J., 1992 Bioassays 14(12):807–15.

In addition to the PPSRP nucleic acids and polypeptides described above, the present invention encompasses these nucleic acids and polypeptides attached to a moiety. These moieties include, but are not limited to, detection moieties, hybridization moieties, purification moieties, delivery moieties, reaction moieties, binding moieties, and the like. A typical group of nucleic acids having moieties attached are probes and primers. Probes and primers typically comprise a substantially isolated oligonucleotide. The oligonucleotide typically comprises a region of nucleotide sequence that hybridizes under stringent conditions to at least about 12, preferably about 25, more preferably about 40, 50 or 75 consecutive nucleotides of a sense strand of one of the sequences set forth in SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31; an anti-sense sequence of one of the sequences set forth in SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31; or naturally occurring mutants thereof. Primers based on a nucleotide sequence of SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31 can be used in PCR reactions to clone PPSRP homologs. Probes based on the PPSRP nucleotide sequences can be used to detect transcripts or genomic sequences encoding the same or substantially identical polypeptides. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express a PPSRP, such as by measuring a level of a PPSRP-encoding nucleic acid, in a sample of cells, e.g., detecting PPSRP mRNA levels or determining whether a genomic PPSRP gene has been mutated or deleted.

In particular, a useful method to ascertain the level of transcription of the gene (an indicator of the amount of mRNA available for translation to the gene product) is to perform a Northern blot (for reference see, for example, Ausubel et al., 1988 Current Protocols in Molecular Biology, Wiley: New York). This information at least partially demonstrates the degree of transcription of the transformed gene. Total cellular RNA can be prepared from cells, tissues or organs by several methods, all well-known in the art, such as that described in Bormann, E. R. et al., 1992 Mol. Microbiol. 6:317–326. To assess the presence or relative quantity of polypeptide translated from this mRNA, standard techniques, such as a Western blot, may be employed. These techniques are well known to one of ordinary skill in the art. (See, for example, Ausubel et al., 1988 Current Protocols in Molecular Biology, Wiley: New York).

The invention further provides an isolated recombinant expression vector comprising a PPSRP nucleic acid as described above, wherein expression of the vector in a host cell results in increased tolerance to environmental stress as compared to a wild type variety of the host cell. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990) or see: Gruber and Crosby, in: Methods in Plant Molecular Biology and Biotechnology, eds. Glick and Thompson, Chapter 7, 89–108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., PPSRPs, mutant forms of PPSRPs, fusion polypeptides, etc.).

The recombinant expression vectors of the invention can be designed for expression of PPSRPs in prokaryotic or eukaryotic cells. For example, PPSRP genes can be expressed in bacterial cells such as *C. glutamicum*, insect cells (using baculovirus expression vectors), yeast and other fungal cells (see Romanos, M. A. et al., 1992 Foreign gene expression in yeast: a review, Yeast 8:423–488; van den Hondel, C. A. M. J. J. et al., 1991 Heterologous gene expression in filamentous fungi, in: More Gene Manipulations in Fungi, J. W. Bennet & L. L. Lasure, eds., p. 396–428: Academic Press: San Diego; and van den Hondel, C. A. M. J. J. & Punt, P. J., 1991 Gene transfer systems and vector development for filamentous fungi, in: Applied Molecular Genetics of Fungi, Peberdy, J. F. et al., eds., p. 1–28, Cambridge University Press: Cambridge), algae (Falciatore et al., 1999 Marine Biotechnology 1(3):239–251), ciliates of the types: Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella, and Stylonychia, especially of the genus Stylonychia lemnae with vectors following a transformation method as described in PCT Application No. WO 98/01572 and multicellular plant cells (see Schmidt, R. and Willmitzer, L., 1988 High efficiency *Agrobacterium tumefaciens*-mediated transformation of *Arabidopsis thaliana* leaf and cotyledon explants, Plant Cell Rep. 583–586; Plant Molecular Biology and Biotechnology, C Press, Boca Raton, Fla., chapter 6/7, S. 71–119 (1993); F. F. White, B. Jenes et al., Techniques for Gene Transfer, in: Transgenic Plants, Vol. 1, Engineering and Utilization, eds. Kung und R. Wu, 128–43, Academic Press: 1993; Potrykus, 1991 Annu. Rev. Plant Physiol. Plant Molec. Biol. 42:205–225 and references cited therein) or mammalian cells. Suitable host cells are discussed further in Goeddel, *Gene Expression Technology: Methods in Enzymology* 185, Academic Press: San Diego, Calif. (1990). Alternatively, the recombinant expression vector can be transcribed and translated in vitro, for example using T7 promoter regulatory sequences and T7 polymerase.

Expression of polypeptides in prokaryotes is most often carried out with vectors containing constitutive or inducible promoters directing the expression of either fusion or non-fusion polypeptides. Fusion vectors add a number of amino acids to a polypeptide encoded therein, usually to the amino terminus of the recombinant polypeptide but also to the C-terminus or fused within suitable regions in the polypeptides. Such fusion vectors typically serve three purposes: 1) to increase expression of a recombinant polypeptide; 2) to increase the solubility of a recombinant polypeptide; and 3) to aid in the purification of a recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin and enterokinase.

Typical fusion expression vectors include pGEX (Pharmacia Biotech Inc; Smith, D. B. and Johnson, K. S., 1988 Gene 67:31–40), pMAL (New England Biolabs, Beverly, Mass.) and pRIT5 (Pharmacia, Piscataway, N.J.) which fuse glutathione S-transferase (GST), maltose E binding polypeptide, or polypeptide A, respectively, to the target recombinant polypeptide. In one embodiment, the coding sequence of the PPSRP is cloned into a pGEX expression vector to create a vector encoding a fusion polypeptide comprising, from the N-terminus to the C-terminus, GST-thrombin cleavage site-X polypeptide. The fusion polypeptide can be purified by affinity chromatography using glutathione-agarose resin. Recombinant PPSRP unfused to GST can be recovered by cleavage of the fusion polypeptide with thrombin.

Examples of suitable inducible non-fusion *E. coli* expression vectors include pTrc (Amann et al., 1988 Gene 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant polypeptide expression is to express the polypeptide in a host bacteria with an impaired capacity to proteolytically cleave the recombinant polypeptide (Gottesman, S., *Gene Expression Technology: Methods in Enzymology* 185, Academic Press, San Diego, Calif. (1990) 119–128). Another strategy is to alter the sequence of the nucleic acid to be inserted into an expression vector so that the individual codons for each amino acid are those preferentially utilized in the bacterium chosen for expression, such as *C. glutamicum* (Wada et al., 1992 Nucleic Acids Res. 20:2111–2118). Such alteration of nucleic acid sequences of the invention can be carried out by standard DNA synthesis techniques.

In another embodiment, the PPSRP expression vector is a yeast expression vector. Examples of vectors for expression in yeast *S. cerevisiae* include pYepSec1 (Baldari, et al., 1987 EMBO J. 6:229–234), pMFa (Kurjan and Herskowitz, 1982

Cell 30:933–943), pJRY88 (Schultz et al., 1987 Gene 54:113–123), and pYES2 (Invitrogen Corporation, San Diego, Calif.). Vectors and methods for the construction of vectors appropriate for use in other fungi, such as the filamentous fungi, include those detailed in: van den Hondel, C. A. M. J. J. & Punt, P. J. (1991) "Gene transfer systems and vector development for filamentous fungi," in: Applied Molecular Genetics of Fungi, J. F. Peberdy, et al., eds., p. 1–28, Cambridge University Press: Cambridge.

Alternatively, the PPSRPs of the invention can be expressed in insect cells using baculovirus expression vectors. Baculovirus vectors available for expression of polypeptides in cultured insect cells (e.g., Sf 9 cells) include the pAc series (Smith et al., 1983 Mol. Cell Biol. 3:2156–2165) and the pVL series (Lucklow and Summers, 1989 Virology 170:31–39).

In yet another embodiment, a PPSRP nucleic acid of the invention is expressed in mammalian cells using a mammalian expression vector. Examples of mammalian expression vectors include pCDM8 (Seed, B., 1987 Nature 329:840) and pMT2PC (Kaufman et al., 1987 EMBO J. 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. latest ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987 Genes Dev. 1:268–277), lymphoid-specific promoters (Calame and Eaton, 1988 Adv. Immunol. 43:235–275), in particular promoters of T cell receptors (Winoto and Baltimore, 1989 EMBO J. 8:729–733) and immunoglobulins (Banerji et al., 1983 Cell 33:729–740; Queen and Baltimore, 1983 Cell 33:741–748), neuron-specific promoters (e.g., the neurofilament promoter; Byrne and Ruddle, 1989 *PNAS* 86:5473–5477), pancreas-specific promoters (Edlund et al., 1985 Science 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990 Science 249:374–379) and the fetopolypeptide promoter (Campes and Tilghman, 1989 Genes Dev. 3:537–546).

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those that confer resistance to drugs, such as G418, hygromycin and methotrexate or in plants that confer resistance towards a herbicide such as glyphosate or glufosinate. Nucleic acid molecules encoding a selectable marker can be introduced into a host cell on the same vector as that encoding a PPSRP or can be introduced on a separate vector. Cells stably transfected with the introduced nucleic acid molecule can be identified by, for example, drug selection (e.g., cells that have incorporated the selectable marker gene will survive, while the other cells die).

In a preferred embodiment of the present invention, the PPSRPs are expressed in plants and plants cells such as unicellular plant cells (such as algae) (see Falciatore et al., 1999 Marine Biotechnology 1(3):239–251 and references therein) and plant cells from higher plants (e.g., the spermatophytes, such as crop plants). A PPSRP may be "introduced" into a plant cell by any means, including transfection, transformation or transduction, electroporation, particle bombardment, agroinfection and the like.

Suitable methods for transforming or transfecting host cells including plant cells can be found in Sambrook, et al. (Molecular Cloning: A Laboratory Manual. latest ed., Cold Spring Harbor Laboratory, Cold Spring Harbor Laboratory Press, Cold Spring Harbor, N.Y., 1989) and other laboratory manuals such as Methods in Molecular Biology, 1995, Vol. 44, *Agrobacterium* protocols, ed: Gartland and Davey, Humana Press, Totowa, N.J. As biotic and abiotic stress tolerance is a general trait wished to be inherited into a wide variety of plants like maize, wheat, rye, oat, triticale, rice, barley, soybean, peanut, cotton, rapeseed and canola, manihot, pepper, sunflower and tagetes, solanaceous plants like potato, tobacco, eggplant, and tomato, Vicia species, pea, alfalfa, bushy plants (coffee, cacao, tea), Salix species, trees (oil palm, coconut), perennial grasses and forage crops, these crop plants are also preferred target plants for a genetic engineering as one further embodiment of the present invention. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover and Sweet Clover.

In one embodiment of the present invention, transfection of a PPSRP into a plant is achieved by *Agrobacterium* mediated gene transfer. *Agrobacterium* mediated plant transformation can be performed using for example the GV3101 (pMP90) (Koncz and Schell, 1986 Mol. Gen. Genet. 204: 383–396) or LBA4404 (Clontech) *Agrobacterium tumefaciens* strain. Transformation can be performed by standard transformation and regeneration techniques (Deblaere et al., 1994 Nucl. Acids. Res. 13:4777–4788; Gelvin, Stanton B. and Schilperoort, Robert A, Plant Molecular Biology Manual, $2^{nd}$ Ed.—Dordrecht: Kluwer Academic Publ., 1995.—in Sect., Ringbuc Zentrale Signatur: BT11-P ISBN 0-7923-2731-4; Glick, Bernard R.; Thompson, John E., Methods in Plant Molecular Biology and Biotechnology, Boca Raton: CRC Press, 1993 360 S., ISBN 0-8493-5164-2). For example, rapeseed can be transformed via cotyledon or hypocotyl transformation (Moloney et al., 1989 Plant cell Report 8:238–242; De Block et al., 1989 Plant Physiol. 91:694–701). Use of antibiotica for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., 1994 Plant Cell Report 13:282–285. Additionally, transformation of soybean can be performed using for example a technique described in European Patent No. 0424 047, U.S. Pat. No. 5,322,783, European Patent No. 0397 687, U.S. Pat. No. 5,376,543 or U.S. Pat. No. 5,169, 770. Transformation of maize can be achieved by particle bombardment, polyethylene glycol mediated DNA uptake or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387 and a specific example of wheat transformation can be found in PCT Application No. WO 93/07256.

According to the present invention, the introduced PPSRP may be maintained in the plant cell stably if it is incorporated into a non-chromosomal autonomous replicon or integrated into the plant chromosomes. Alternatively, the introduced PPSRP may be present on an extra-chromosomal non-replicating vector and be transiently expressed or transiently active.

In one embodiment, a homologous recombinant microorganism can be created wherein the PPSRP is integrated into a chromosome, a vector is prepared which contains at least a portion of a PPSRP gene into which a deletion, addition or substitution has been introduced to thereby alter, e.g., functionally disrupt, the PPSRP gene. Preferably, the PPSRP gene is a *Physcomitrella patens, Brassica napus, Glycine max*, or *Oryza sativa* PPSRP gene, but it can be a homolog from a related plant or even from a mammalian, yeast, or insect source. In a preferred embodiment, the vector is designed such that, upon homologous recombination, the endogenous PPSRP gene is functionally disrupted (i.e., no longer encodes a functional polypeptide; also referred to as a knock-out vector). Alternatively, the vector can be designed such that, upon homologous recombination, the endogenous PPSRP gene is mutated or otherwise altered but still encodes a functional polypeptide (e.g., the upstream regulatory region can be altered to thereby alter the expression of the endogenous PPSRP). To create a point mutation via homologous recombination, DNA-RNA hybrids can be used in a technique known as chimeraplasty (Cole-Strauss et al., 1999 Nucleic Acids Research 27(5):1323–1330 and Kmiec, 1999 Gene therapy American Scientist. 87(3):240–247). Homologous recombination procedures in *Physcomitrella patens* are also well known in the art and are contemplated for use herein.

Whereas in the homologous recombination vector, the altered portion of the PPSRP gene is flanked at its 5' and 3' ends by an additional nucleic acid molecule of the PPSRP gene to allow for homologous recombination to occur between the exogenous PPSRP gene carried by the vector and an endogenous PPSRP gene, in a microorganism or plant. The additional flanking PPSRP nucleic acid molecule is of sufficient length for successful homologous recombination with the endogenous gene. Typically, several hundreds of base pairs up to kilobases of flanking DNA (both at the 5' and 3' ends) are included in the vector (see e.g., Thomas, K. R., and Capecchi, M. R., 1987 Cell 51:503 for a description of homologous recombination vectors or Strepp et al., 1998 PNAS, 95 (8):4368–4373 for cDNA based recombination in *Physcomitrella patens*). The vector is introduced into a microorganism or plant cell (e.g., via polyethylene glycol mediated DNA), and cells in which the introduced PPSRP gene has homologously recombined with the endogenous PPSRP gene are selected using art-known techniques.

In another embodiment, recombinant microorganisms can be produced that contain selected systems that allow for regulated expression of the introduced gene. For example, inclusion of a PPSRP gene on a vector placing it under control of the lac operon permits expression of the PPSRP gene only in the presence of IPTG. Such regulatory systems are well known in the art.

Whether present in an extra-chromosomal non-replicating vector or a vector that is integrated into a chromosome, the PPSRP polynucleotide preferably resides in a plant expression cassette. A plant expression cassette preferably contains regulatory sequences capable of driving gene expression in plant cells that are operatively linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984 EMBO J. 3:835) or functional equivalents thereof but also all other terminators functionally active in plants are suitable. As plant gene expression is very often not limited on transcriptional levels, a plant expression cassette preferably contains other operatively linked sequences like translational enhancers such as the overdrive-sequence containing the 5'-untranslated leader sequence from tobacco mosaic virus enhancing the polypeptide per RNA ratio (Gallie et al., 1987 Nucl. Acids Research 15:8693–8711). Examples of plant expression vectors include those detailed in: Becker, D., Kemper, E., Schell, J. and Masterson, R., 1992 New plant binary vectors with selectable markers located proximal to the left border, Plant Mol. Biol. 20: 1195–1197; and Bevan, M. W., 1984 Binary *Agrobacterium* vectors for plant transformation, Nucl. Acid. Res. 12:8711–8721; Vectors for Gene Transfer in Higher Plants; in: Transgenic Plants, Vol. 1, Engineering and Utilization, eds.: Kung and R. Wu, Academic Press, 1993, S. 15–38.

Plant gene expression should be operatively linked to an appropriate promoter conferring gene expression in a timely, cell or tissue specific manner. Promoters useful in the expression cassettes of the invention include any promoter that is capable of initiating transcription in a plant cell. Such promoters include, but are not limited to those that can be obtained from plants, plant viruses, and bacteria that contain genes that are expressed in plants, such as *Agrobacterium* and *Rhizobium*.

The promoter may be constitutive, inducible, developmental stage-preferred, cell type-preferred, tissue-preferred or organ-preferred. Constitutive promoters are active under most conditions. Examples of constitutive promoters include the CaMV 19S and 35 S promoters (Odell et al. (1985) Nature 313:810–812), the sX CaMV 35S promoter (Kay et al. (1987) Science 236:1299–1302) the Sep1 promoter, the rice actin promoter (McElroy et al. (1990) Plant Cell 2:163–171), the *Arabidopsis* actin promoter, the ubiquitan promoter (Christensen et al. (1989) Plant Molec Biol 18:675–689); pEmu (Last et al. (1991) Theor Appl Genet 81:581–588), the figwort mosaic virus 35S promoter, the Smas promoter (Velten et al. (1984) EMBO J 3:2723–2730), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssuRUBISCO) prompter, and the like.

Inducible promoters are active under certain environmental conditions, such as the presence or absence of a nutrient or metabolite, heat or cold, light, pathogen attack, anaerobic conditions, and the like. For example, the hsp80 promoter from *Brassica* is induced by heat shock, the PPDK promoter is induced by light, the PR-1 promoter from tobacco, *Arabidopsis* and maize are inducible by infection with a pathogen, and the Adh1 promoter is induced by hypoxia and cold stress. Plant gene expression can also be facilitated via an inducible promoter (for review see Gatz, 1997 Annu. Rev. Plant Physiol. Plant Mol. Biol. 48:89–108). Chemically inducible promoters are especially suitable if gene expression is wanted to occur in a time specific manner. Examples of such promoters are a salicylic acid inducible promoter (PCT Application No. WO 95/19443), a tetracycline inducible promoter (Gatz et al., 1992 Plant J. 2:397–404) and an ethanol inducible promoter (PCT Application No. WO 93/21334). Also, suitable promoters responding to biotic or abiotic stress conditions are those such as the pathogen inducible PRP1-gene promoter (Ward et al., 1993 Plant. Mol. Biol. 22:361–366), the heat inducible hsp80-promoter from tomato (U.S. Pat. No. 5,187,267), cold inducible alpha-amylase promoter from potato (PCT Application No. WO 96/12814) or the wound-inducible pinII-promoter (European Patent No. 375091). For other examples of drought, cold, and salt-inducible promoters, such as the RD29A promoter, see Yamaguchi-Shinozalei et al. (1993 Mol. Gen. Genet. 236:331–340).

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, and leaf-preferred, stigma-preferred, pollen-preferred, anther-preferred, a petal-preferred, sepal-preferred, pedicel-preferred, silique-preferred, stem-preferred, root-preferred promoters and the like. Seed preferred promoters are preferentially expressed during seed development and/or germination. For example, seed preferred promoters can be embryo-preferred, endosperm preferred and seed coat-preferred. See Thompson et al. (1989) BioEssays 10:108. Examples of seed preferred promoters include, but are not limited to cellulose synthase (ce1A), Cim1, gamma-zein, globulin-1, maize 19 kD zein (cZ19B1) and the like.

Other suitable tissue-preferred or organ-preferred promoters include the napin-gene promoter from rapeseed (U.S. Pat. No. 5,608,152), the USP-promoter from Vicia faba (Baeumlein et al., 1991 Mol Gen Genet. 225(3):459–67), the oleosin-promoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980) or the legumin B4 promoter (LeB4; Baeumlein et al., 1992 Plant Journal, 2(2):233–9) as well as promoters conferring seed specific expression in monocot plants like maize, barley, wheat, rye, rice, etc. Suitable promoters to note are the lpt2 or lpt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, Sorghum kasirin-gene and rye secalin gene).

Other promoters useful in the expression cassettes of the invention include, but are not limited to, the major chlorophyll a/b binding protein promoter, histone promoters, the Ap3 promoter, the β-conglycin promoter, the napin promoter, the soy bean lectin promoter, the maize 15 kD zein promoter, the 22 kD zein promoter, the 27 kD zein promoter, the g-zein promoter, the waxy, shrunken 1, shrunken 2 and bronze promoters, the Zm13 promoter (U.S. Pat. No. 5,086,169), the maize polygalacturonase promoters (PG) (U.S. Pat. Nos. 5,412,085 and 5,545,546) and the SGB6 promoter (U.S. Pat. No. 5,470,359), as well as synthetic or other natural promoters.

Additional flexibility in controlling heterologous gene expression in plants may be obtained by using DNA binding domains and response elements from heterologous sources (i.e., DNA binding domains from non-plant sources). Some examples of such heterologous DNA binding domains include the LexA and GAL4 DNA binding domains, Schwechheimer et al. (1998) Plant Mol Biol 36:195–204. The LexA DNA-binding domain is part of the repressor protein LexA from *Escherichia coli* (*E. coli*) (Brent and Ptashne, Cell 43:729–736 (1985)).

The invention further provides a recombinant expression vector comprising a PPSRP DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to a PPSRP mRNA. Regulatory sequences operatively linked to a nucleic acid molecule cloned in the antisense orientation can be chosen which direct the continuous expression of the antisense RNA molecule in a variety of cell types. For instance, viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus wherein antisense nucleic acids are produced under the control of a high efficiency regulatory region. The activity of the regulatory region can be determined by the cell type into which the vector is introduced. For a discussion of the regulation of gene expression using antisense genes, see Weintraub, H. et al., Antisense RNA as a molecular tool for genetic analysis, Reviews—Trends in Genetics, Vol. 1(1) 1986 and Mol et al., 1990 FEBS Letters 268:427–430.

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, a PPSRP can be expressed in bacterial cells such as *C. glutamicum*, insect cells, fungal cells or mammalian cells (such as Chinese hamster ovary cells (CHO) or COS cells), algae, ciliates, plant cells, fungi or other microorganisms like *C. glutamicum*. Other suitable host cells are known to those skilled in the art.

A host cell of the invention, such as a prokaryotic or eukaryotic host cell in culture, can be used to produce (i.e., express) a PPSRP. Accordingly, the invention further provides methods for producing PPSRPs using the host cells of the invention. In one embodiment, the method comprises culturing the host cell of invention (into which a recombinant expression vector encoding a PPSRP has been introduced, or into which genome has been introduced a gene encoding a wild-type or altered PPSRP) in a suitable medium until PPSRP is produced. In another embodiment, the method further comprises isolating PPSRPs from the medium or the host cell.

Another aspect of the invention pertains to isolated PPSRPs, and biologically active portions thereof. An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of PPSRP in which the polypeptide is separated from some of the cellular components of the cells in which it is naturally or recombinantly produced. In one embodiment, the language "substantially free of cellular material" includes preparations of a PPSRP having less than about 30% (by dry weight) of non-PPSRP material (also referred to herein as a "contaminating polypeptide"), more preferably less than about 20% of non-PPSRP material, still more preferably less than about 10% of non-PPSRP material, and most preferably less than about 5% non-PPSRP material.

When the PPSRP or biologically active portion thereof is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of PPSRP in which the polypeptide is separated from chemical precursors or other chemicals that are involved in the synthesis of the polypeptide. In one embodiment, the language "substantially free of chemical precursors or other chemicals" includes preparations of a PPSRP having less than about 30% (by dry weight) of chemical precursors or non-PPSRP chemicals, more preferably less than about 20% chemical precursors or non-PPSRP chemicals, still more preferably less than about 10% chemical precursors or non-PPSRP chemicals, and most preferably less than about 5% chemical precursors or non-PPSRP chemicals. In preferred embodiments, isolated polypeptides, or biologically active portions thereof, lack contaminating polypeptides from the same organism from which the PPSRP is derived. Typically, such polypeptides are produced by recombinant expression of, for example, a *Physcomitrella patens* PPSRP in plants other than *Physcomitrella patens* or microorganisms such as *C. glutamicum*, ciliates, algae or fungi.

The nucleic acid molecules, polypeptides, polypeptide homologs, fusion polypeptides, primers, vectors, and host cells described herein can be used in one or more of the following methods: identification of *Physcomitrella patens, Brassican napus, Glycine max, Oryza sativa*, and related organisms; mapping of genomes of organisms related to *Physcomitrella patens, Brassican napus, Glycine max,* or *Oryza sativa*; identification and localization of *Physcomitrella patens, Brassican napus, Glycine max,* or *Oryza sativa* sequences of interest; evolutionary studies; determination of PPSRP regions required for function; modulation of a PPSRP activity; modulation of the metabolism of one or more cell functions; modulation of the transmembrane transport of one or more compounds; and modulation of stress resistance.

The moss *Physcomitrella patens* represents one member of the mosses. It is related to other mosses such as *Ceratodon purpureus*, which is capable of growth in the absence of light. Mosses like *Ceratodon* and *Physcomitrella* share a high degree of sequence identity on the DNA sequence and polypeptide level allowing the use of heterologous screening of DNA molecules with probes evolving from other mosses or organisms, thus enabling the derivation of a consensus sequence suitable for heterologous screening or functional annotation and prediction of gene functions in third species. The ability to identify such functions can therefore have significant relevance, e.g., prediction of substrate specificity of enzymes. Further, these nucleic acid molecules may serve as reference points for the mapping of moss genomes, or of genomes of related organisms.

The PPSRP nucleic acid molecules of the invention have a variety of uses. Most importantly, the nucleic acid and amino acid sequences of the present invention can be used to transform plants, thereby inducing tolerance to stresses such as drought, high salinity and cold. The present invention therefore provides a transgenic plant transformed by a PPSRP nucleic acid, wherein expression of the nucleic acid sequence in the plant results in increased tolerance to environmental stress as compared to a wild type variety of the plant. The transgenic plant can be a monocot or a dicot. The invention further provides that the transgenic plant can be selected from maize, wheat, rye, oat, triticale, rice, barley, soybean, peanut, cotton, rapeseed, canola, manihot, pepper, sunflower, tagetes, solanaceous plants, potato, tobacco, eggplant, tomato, Vicia species, pea, alfalfa, coffee, cacao, tea, Salix species, oil palm, coconut, perennial grass and forage crops, for example.

In particular, the present invention describes using the expression of PP2A-1 and PP-1 of *Physcomitrella patens*; BnPP2A-1, BnPP2A-2, and BnPP2A-3 of *Brassica napus*; GmPP2A-1, GmPP2A-2, GmPP2A-3, GmPP2A-4, and GmPP2A-5 of *Glycine max*; and OsPP2A-1, OsPP2A-2, OsPP2A-3, OsPP2A-4, and OsPP2A-5 of *Oryza sativa* to engineer drought-tolerant, salt-tolerant and/or cold-tolerant plants. This strategy has herein been demonstrated for *Arabidopsis thaliana*, Rapeseed/Canola, soybeans, corn, and wheat, but its application is not restricted to these plants. Accordingly, the invention provides a transgenic plant containing a PPSRP such as PP2A-1 (SEQ ID NO:3), PP-1 (SEQ ID NO:6), BnPP2A-1 (SEQ ID NO:8), BnPP2A-2 (SEQ ID NO:10), BnPP2A-3 (SEQ ID NO:12), GmPP2A-1 (SEQ ID NO:14), GmPP2A-2 (SEQ ID NO:16), GmPP2A-3 (SEQ ID NO:18), GmPP2A-4 (SEQ ID NO:20), GmPP2A-5 (SEQ ID NO:22), OsPP2A-1 (SEQ ID NO:24), OsPP2A-2 (SEQ ID NO:26), OsPP2A-3 (SEQ ID NO:28), OsPP2A-4 (SEQ ID NO:30), and OsPP2A-5 (SEQ ID NO:32), wherein the plant has an increased tolerance to an environmental stress selected from drought, increased or decreased salinity, and decreased or increased temperature. In preferred embodiments, the environmental stress is drought or increased salinity.

Accordingly, the invention provides a method of producing a transgenic plant with a PPSRP coding nucleic acid, wherein expression of the nucleic acid(s) in the plant results in increased tolerance to environmental stress as compared to a wild type variety of the plant comprising: (a) introducing into a plant cell an expression vector comprising a PPSRP nucleic acid, and (b) generating from the plant cell a transgenic plant with a increased tolerance to environmental stress as compared to a wild type variety of the plant. The plant cell includes, but is not limited to, a protoplast, gamete producing cell, and a cell that regenerates into a whole plant. As used herein, the term "transgenic" refers to any plant, plant cell, callus, plant tissue or plant part, that contains all or part of at least one recombinant polynucleotide. In many cases, all or part of the recombinant polynucleotide is stably integrated into a chromosome or stable extra-chromosomal element, so that it is passed on to successive generations.

The present invention also provides a method of modulating a plant's tolerance to an environmental stress comprising, modifying the expression of a PPSRP coding nucleic acid in the plant. The plant's tolerance to the environmental stress can be increased or decreased as achieved by increasing or decreasing the expression of a PPSRP, respectively. Preferably, the plant's tolerance to the environmental stress is increased by increasing expression of a PPSRP. Expression of a PPSRP can be modified by any method known to those of skill in the art. The methods of increasing expression of PPSRPs can be used wherein the plant is either transgenic or not transgenic. In cases when the plant is transgenic, the plant can be transformed with a vector containing any of the above described PPSRP coding nucleic acids, or the plant can be transformed with a promoter that directs expression of native PPSRP in the plant, for example. The invention provides that such a promoter can be tissue specific. Furthermore, such a promoter can be developmentally regulated. Alternatively, non-transgenic plants can have native PPSRP expression modified by inducing a native promoter. The expression of PP2A-1 (SEQ ID NO:2), PP-1 (SEQ ID NO:5), BnPP2A-1 (SEQ ID NO;7), BnPP2A-2 (SEQ ID NO:9), BnPP2A-5 (SEQ ID NO:11), GmPP2A-1 (SEQ ID NO:13), GmPP2A-2 (SEQ ID NO:15), GmPP2A-3 (SEQ ID NO:17), GmPP2A-4 (SEQ ID NO:19), GmPP2A-5 (SEQ ID NO:21), OsPP2A-1 (SEQ ID NO:23), OsPP2A-2 (SEQ ID NO:25), OsPP2A-3 (SEQ ID NO:27), OsPP2A-4 (SEQ ID NO:29), or OsPP2A-5 (SEQ ID NO:31) in target plants can be accomplished by, but is not limited to, one of the following examples: (a) constitutive promoter, (b) stress-inducible promoter, (c) chemical-induced promoter, and (d) engineered promoter over-expression with for example zinc-finger derived transcription factors (Greisman and Pabo, 1997 Science 275:657).

In a preferred embodiment, transcription of the PPSRP is modulated using zinc-finger derived transcription factors (ZFPs) as described in Greisman and Pabo, 1997 Science 275:657 and manufactured by Sangamo Biosciences, Inc. These ZFPs comprise both a DNA recognition domain and a functional domain that causes activation or repression of a target nucleic acid such as a PPSRP nucleic acid. Therefore, activating and repressing ZFPs can be created that specifically recognize the PPSRP promoters described above and used to increase or decrease PPSRP expression in a plant, thereby modulating the stress tolerance of the plant. The present invention also includes identification of the PP2A-1 (SEQ ID NO:2), PP-1 (SEQ ID NO:5), BnPP2A-1 (SEQ ID NO:7), BnPP2A-2 (SEQ ID NO:9), BnPP2A-5 (SEQ ID NO:11), GmPP2A-1 (SEQ ID NO:13), GmPP2A-2 (SEQ ID NO:15), GmPP2A-3 (SEQ ID NO:17), GmPP2A-4 (SEQ ID NO:19), GmPP2A-5 (SEQ ID NO:21), OsPP2A-1 (SEQ ID NO:23), OsPP2A-2 (SEQ ID NO:25), OsPP2A-3 (SEQ ID NO:27), OsPP2A-4 (SEQ ID NO:29), and OsPP2A-5 (SEQ ID NO:31) homologs in a target plant as well as the homolog's promoter. The invention also provides a method of increasing expression of a gene of interest within a host cell as compared to a wild type variety of the host cell, wherein the gene of interest is transcribed in response to a PPSRP, comprising: (a) transforming the host cell with an expression vector comprising a PPSRP coding nucleic acid, and (b) expressing the PPSRP within the host cell, thereby increasing the expression of the gene transcribed in response to the PPSRP, as compared to a wild type variety of the host cell.

In addition to introducing the PPSRP nucleic acid sequences into transgenic plants, these sequences can also be used to identify an organism as being *Physcomitrella patens, Brassican napus, Glycine max, Oryza sativa* or a close relative thereof. Also, they may be used to identify the presence of *Physcomitrella patens, Brassican napus, Glycine max, Oryza sativa* or a relative thereof in a mixed population of microorganisms. The invention provides the nucleic acid sequences of a number of *Physcomitrella patens, Brassican napus, Glycine max*, and *Oryza sativa* genes; by probing the extracted genomic DNA of a culture of a unique or mixed population of microorganisms under stringent conditions with a probe spanning a region of a gene, which is unique to this organism, one can ascertain whether this organism is present.

Further, the nucleic acid and polypeptide molecules of the invention may serve as markers for specific regions of the genome. This has utility not only in the mapping of the genome, but also in functional studies of *Physcomitrella patens, Brassican napus, Glycine max*, or *Oryza sativa* polypeptides. For example, to identify the region of the genome to which a particular *Physcomitrella patens* DNA-binding polypeptide binds, the *Physcomitrella patens* genome could be digested, and the fragments incubated with the DNA-binding polypeptide. Those fragments that bind the polypeptide may be additionally probed with the nucleic acid molecules of the invention, preferably with readily detectable labels. Binding of such a nucleic acid molecule to the genome fragment enables the localization of the fragment to the genome map of *Physcomitrella patens*, and, when performed multiple times with different enzymes, facilitates a rapid determination of the nucleic acid sequence to which the polypeptide binds. Further, the nucleic acid molecules of the invention may be sufficiently identical to the sequences of related species such that these nucleic acid molecules may serve as markers for the construction of a genomic map in related mosses.

The PPSRP nucleic acid molecules of the invention are also useful for evolutionary and polypeptide structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the polypeptide that are essential for the functioning of the enzyme. This type of determination is of value for polypeptide engineering studies and may give an indication of what the polypeptide can tolerate in terms of mutagenesis without losing function.

Manipulation of the PPSRP nucleic acid molecules of the invention may result in the production of PPSRPs having functional differences from the wild-type PPSRPs. These polypeptides may be improved in efficiency or activity, may be present in greater numbers in the cell than is usual, or may be decreased in efficiency or activity.

There are a number of mechanisms by which the alteration of a PPSRP of the invention may directly affect stress response and/or stress tolerance. In the case of plants expressing PPSRPs, increased transport can lead to improved salt and/or solute partitioning within the plant tissue and organs. By either increasing the number or the activity of transporter molecules that export ionic molecules from the cell, it may be possible to affect the salt tolerance of the cell.

The effect of the genetic modification in plants, *C. glutamicum*, fungi, algae, or ciliates on stress tolerance can be assessed by growing the modified microorganism or plant under less than suitable conditions and then analyzing the growth characteristics and/or metabolism of the plant. Such analysis techniques are well known to one skilled in the art, and include dry weight, wet weight, polypeptide synthesis, carbohydrate synthesis, lipid synthesis, evapotranspiration rates, general plant and/or crop yield, flowering, reproduction, seed setting, root growth, respiration rates, photosynthesis rates, etc. (Applications of HPLC in Biochemistry in: Laboratory Techniques in Biochemistry and Molecular Biology, vol. 17; Rehm et al., 1993 Biotechnology, vol. 3, Chapter III: Product recovery and purification, page 469–714, VCH: Weinheim; Belter, P. A. et al., 1988 Bioseparations: downstream processing for biotechnology, John Wiley and Sons; Kennedy, J. F. and Cabral, J. M. S., 1992 Recovery processes for biological materials, John Wiley and Sons; Shaeiwitz, J. A. and Henry, J. D., 1988 Biochemical separations, in: Ulmann's Encyclopedia of Industrial Chemistry, vol. B3, Chapter 11, page 1–27, VCH: Weinheim; and Dechow, F. J. (1989) Separation and purification techniques in biotechnology, Noyes Publications).

For example, yeast expression vectors comprising the nucleic acids disclosed herein, or fragments thereof, can be constructed and transformed into *Saccharomyces cerevisiae* using standard protocols. The resulting transgenic cells can then be assayed for fail or alteration of their tolerance to drought, salt, and temperature stress. Similarly, plant expression vectors comprising the nucleic acids disclosed herein, or fragments thereof, can be constructed and transformed into an appropriate plant cell such as *Arabidopsis*, soy, rape, maize, wheat, *Medicago truncatula*, etc., using standard protocols. The resulting transgenic cells and/or plants derived there from can then be assayed for fail or alteration of their tolerance to drought, salt, and temperature stress.

The engineering of one or more PPSRP genes of the invention may also result in PPSRPs having altered activities which indirectly impact the stress response and/or stress tolerance of algae, plants, ciliates or fungi or other microorganisms like *C. glutamicum*. For example, the normal biochemical processes of metabolism result in the production of a variety of products (e.g., hydrogen peroxide and other reactive oxygen species) which may actively interfere with these same metabolic processes (for example, peroxynitrite is known to nitrate tyrosine side chains, thereby inactivating some enzymes having tyrosine in the active site (Groves, J. T., 1999 Curr. Opin. Chem. Biol. 3(2):226–235). While these products are typically excreted, cells can be genetically altered to transport more products than is typical for a wild-type cell. By optimizing the activity of one or more PPSRPs of the invention that are involved in the export of specific molecules, such as salt molecules, it may be possible to improve the stress tolerance of the cell.

Additionally, the sequences disclosed herein, or fragments thereof, can be used to generate knockout mutations in the genomes of various organisms, such as bacteria, mammalian cells, yeast cells, and plant cells (Girke, T., 1998 The Plant Journal 15:39–48). The resultant knockout cells can then be evaluated for their ability or capacity to tolerate various stress conditions, their response to various stress conditions, and the effect on the phenotype and/or genotype of the mutation. For other methods of gene inactivation see U.S. Pat. No. 6,004,804 "Non-Chimeric Mutational Vectors" and Puttaraju et al., 1999 Spliceosome-mediated RNA trans-splicing as a tool for gene therapy Nature Biotechnology 17:246–252.

The aforementioned mutagenesis strategies for PPSRPs resulting in increased stress resistance are not meant to be limiting; variations on these strategies will be readily apparent to one skilled in the art. Using such strategies, and incorporating the mechanisms disclosed herein, the nucleic acid and polypeptide molecules of the invention may be utilized to generate algae, ciliates, plants, fungi or other microorganisms like *C. glutamicum* expressing mutated PPSRP nucleic acid and polypeptide molecules such that the stress tolerance is improved.

The present invention also provides antibodies that specifically bind to a PPSRP, or a portion thereof, as encoded by a nucleic acid described herein. Antibodies can be made by many well-known methods (See, e.g. *Harlow* and *Lane*, "Antibodies; A Laboratory Manual" Cold Spring Harbor Laboratory, Cold Spring Harbor, N.Y., (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. (See, for example, Kelly et al., 1992 Bio/Technology 10:163–167; Bebbington et al., 1992 Bio/Technology 10:169–175).

The phrases "selectively binds" and "specifically binds" with the polypeptide refer to a binding reaction that is determinative of the presence of the polypeptide in a heterogeneous population of polypeptides and other biologics. Thus, under designated immunoassay conditions, the specified antibodies bound to a particular polypeptide do not bind in a significant amount to other polypeptides present in the sample. Selective binding of an antibody under such conditions may require an antibody that is selected for its specificity for a particular polypeptide. A variety of immunoassay formats may be used to select antibodies that selectively bind with a particular polypeptide. For example, solid-phase ELISA immunoassays are routinely used to select antibodies selectively immunoreactive with a polypeptide. See *Harlow* and *Lane* "Antibodies, A Laboratory Manual" Cold Spring Harbor Publications, New York, (1988), for a description of immunoassay formats and conditions that could be used to determine selective binding.

In some instances, it is desirable to prepare monoclonal antibodies from various hosts. A description of techniques for preparing such monoclonal antibodies may be found in Stites et al., editors, "Basic and Clinical Immunology," (Lange Medical Publications, Los Altos, Calif., Fourth Edition) and references cited therein, and in *Harlow* and *Lane* ("Antibodies, A Laboratory Manual" Cold Spring Harbor Publications, New York, 1988).

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Growth of *Physcomitrella patens* Cultures

For this study, plants of the species *Physcomitrella patens* (Hedw.) B. S. G. from the collection of the genetic studies section of the University of Hamburg were used. They originate from the strain 16/14 collected by H. L. K. Whitehouse in Gransden Wood, Huntingdonshire (England), which was subcultured from a spore by Engel (1968, Am. J. Bot. 55, 438–446). Proliferation of the plants was carried out by means of spores and by means of regeneration of the gametophytes. The protonema developed from the haploid spore as a chloroplast-rich chloronema and chloroplast-low caulonema, on which buds formed after approximately 12 days. These grew to give gametophores bearing antheridia and archegonia. After fertilization, the diploid sporophyte with a short seta and the spore capsule resulted, in which the meiospores matured.

Culturing was carried out in a climatic chamber at an air temperature of 25° C. and light intensity of 55 micromols$^{-1m2}$ (white light; Philips TL 65W/25 fluorescent tube) and a light/dark change of 16/8 hours. The moss was either modified in liquid culture using Knop medium according to Reski and Abel (1985, Planta 165:354–358) or cultured on Knop solid medium using 1% oxoid agar (Unipath, Basingstoke, England). The protonemas used for RNA and DNA isolation were cultured in aerated liquid cultures. The protonemas were comminuted every 9 days and transferred to fresh culture medium.

Example 2

Total DNA Isolation from Plants

The details for the isolation of total DNA relate to the working up of one gram fresh weight of plant material. The materials used include the following buffers: CTAB buffer: 2% (w/v) N-cethyl-N,N,N-trimethylammonium bromide (CTAB); 100 mM Tris HCl pH 8.0; 1.4 M NaCl; 20 mM EDTA; N-Laurylsarcosine buffer: 10% (w/v) N-laurylsarcosine; 100 mM Tris HCl pH 8.0; 20 mM EDTA.

The plant material was triturated under liquid nitrogen in a mortar to give a fine powder and transferred to 2 ml Eppendorf vessels. The frozen plant material was then covered with a layer of 1 ml of decomposition buffer (1 ml CTAB buffer, 100 µl of N-laurylsarcosine buffer, 20 µl of β-mercaptoethanol and 10 µl of proteinase K solution, 10 mg/ml) and incubated at 60° C. for one hour with continuous shaking. The homogenate obtained was distributed into two Eppendorf vessels (2 ml) and extracted twice by shaking with the same volume of chloroform/isoamyl alcohol (24:1). For phase separation, centrifugation was carried out at 8000×g and room temperature for 15 minutes in each case. The DNA was then precipitated at −70° C. for 30 minutes using ice-cold isopropanol. The precipitated DNA was sedimented at 4° C. and 10,000 g for 30 minutes and resuspended in 180 µl of TE buffer (Sambrook et al., 1989, Cold Spring Harbor Laboratory Press: ISBN 0-87969-309-6). For further purification, the DNA was treated with NaCl (1.2 M final concentration) and precipitated again at −70° C. for 30 minutes using twice the volume of absolute ethanol. After a washing step with 70% ethanol, the DNA was dried and subsequently taken up in 50 µl of H$_2$O+RNAse (50 mg/ml final concentration). The DNA was dissolved overnight at 4° C. and the RNAse digestion was subsequently carried out at 37° C. for 1 hour. Storage of the DNA took place at 4° C.

Example 3

Isolation of Total RNA and Poly-(A)+ RNA and cDNA Library Construction from *Physcomitrella patens*

For the investigation of transcripts, both total RNA and poly-(A)$^+$ RNA were isolated. The total RNA was obtained from wild-type 9 day old protonemata following the GTC-method (Reski et al. 1994, Mol. Gen. Genet., 244:352–359). The Poly(A)+ RNA was isolated using Dyna Beads® (Dynal, Oslo, Norway) following the instructions of the manufacturer's protocol. After determination of the concentration of the RNA or of the poly(A)+ RNA, the RNA was precipitated by addition of 1/10 volumes of 3 M sodium acetate pH 4.6 and 2 volumes of ethanol and stored at −70° C.

For cDNA library construction, first strand synthesis was achieved using Murine Leukemia Virus reverse transcriptase (Roche, Mannheim, Germany) and oligo-d(T)-primers, second strand synthesis by incubation with DNA polymerase I, Klenow enzyme and RNAseH digestion at 12° C. (2 hours), 16° C. (1 hour), and 22° C. (1 hour). The reaction was stopped by incubation at 65° C. (10 minutes) and subsequently transferred to ice. Double stranded DNA molecules were blunted by T4-DNA-polymerase (Roche, Mannheim) at 37° C. (30 minutes). Nucleotides were removed by phenol/chloroform extraction and Sephadex G50 spin columns. EcoRI adapters (Pharmacia, Freiburg, Germany) were ligated to the cDNA ends by T4-DNA-ligase (Roche, 12° C., overnight) and phosphorylated by incubation with polynucleotide kinase (Roche, 37° C., 30 minutes). This mixture was subjected to separation on a low melting agarose gel. DNA molecules larger than 300 base pairs were eluted from the gel, phenol extracted, concentrated on Elutip-D-columns (Schleicher and Schuell, Dassel, Germany) and were ligated to vector arms and packed into lambda ZAPII phages or lambda ZAP-Express phages using the Gigapack Gold Kit (Stratagene, Amsterdam, Netherlands) using material and following the instructions of the manufacturer.

Example 4

Sequencing and Function Annotation of *Physcomitrella patens* ESTs cDNA libraries as described in Example 3 were used for DNA sequencing according to standard methods, and in particular, by the chain termination method using the ABI PRISM Big Dye Terminator Cycle Sequencing Ready Reaction Kit (Perkin-Elmer, Weiterstadt, Germany). Random Sequencing was carried out subsequent to preparative plasmid recovery from cDNA libraries via in vivo mass excision, retransformation, and subsequent plating of DH10B on agar plates (material and protocol details from Stratagene, Amsterdam, Netherlands). Plasmid DNA was prepared from overnight grown *E. coli* cultures grown in Luria-Broth medium containing ampicillin (see Sambrook et al. 1989. Cold Spring Harbor Laboratory Press: ISBN 0-87969-309-6) on a Qiagene DNA preparation robot (Qiagen, Hilden) according to the manufacturer's protocols. Sequencing primers with the following nucleotide sequences were used:

5'-CAGGAAACAGCTATGACC-3'    SEQ ID NO:33

```
-continued
5'-CTAAAGGGAACAAAAGCTG-3'        SEQ ID NO:34

5'-TGTAAAACGACGGCCAGT-3'        SEQ ID NO:35
```

Sequences were processed and annotated using the software package EST-MAX commercially provided by Bio-Max (Munich, Germany). The program incorporates practically all bioinformatics methods important for functional and structural characterization of protein sequences. The most important algorithms incorporated in EST-MAX are: FASTA (Very sensitive sequence database searches with estimates of statistical significance; Pearson W. R. (1990) Rapid and sensitive sequence comparison with FASTP and FASTA. Methods Enzymol. 183:63–98); BLAST (Very sensitive sequence database searches with estimates of statistical significance. Altschul S. F., Gish W., Miller W., Myers E. W., and Lipman D. J. Basic local alignment search tool. Journal of Molecular Biology 215:403–10); PREDATOR (High-accuracy secondary structure prediction from single and multiple sequences. Frishman, D. and Argos, P. (1997) 75% accuracy in protein secondary structure prediction. Proteins, 27:329–335); CLUSTALW: Multiple sequence alignment. Thompson, J. D., Higgins, D. G. and Gibson, T. J. (1994) CLUSTAL W (improving the sensitivity of progressive multiple sequence alignment through sequence weighting, positions-specific gap penalties and weight matrix choice. Nucleic Acids Research, 22:4673–4680); TMAP (Transmembrane region prediction from multiply aligned sequences. Persson, B. and Argos, P. (1994) Prediction of transmembrane segments in proteins utilizing multiple sequence alignments. J. Mol. Biol. 237:182–192); ALOM2 (Transmembrane region prediction from single sequences. Klein, P., Kanehisa, M., and DeLisi, C. Prediction of protein function from sequence properties: A discriminate analysis of a database. Biochim. Biophys. Acta 787:221–226 (1984). Version 2 by Dr. K. Nakai); PROSEARCH (Detection of PROSITE protein sequence patterns. Kolakowski L. F. Jr., Leunissen J. A. M., Smith J. E. (1992) ProSearch: fast searching of protein sequences with regular expression patterns related to protein structure and function. Biotechniques 13, 919–921); BLIMPS (Similarity searches against a database of ungapped blocks. J. C. Wallace and Henikoff S., (1992)); PATMAT (A searching and extraction program for sequence, pattern and block queries and databases, CABIOS 8:249–254. Written by Bill Alford.).

Example 5

Identification of *Physcomitrella patens* ORFs Corresponding to PpPP2A-1 and PpPP-1

The *Physcomitrella patens* partial cDNAs (ESTs) for PpPP2A-1 (SEQ ID NO:1) and PpPP-1 (SEQ ID NO:4) were identified in the *Physcomitrella patens* EST sequencing program using the program EST-MAX through BLAST analysis. These particular clones, which were found to encode for protein phosphatases, were chosen for further analyses (see Tables 1–3 below).

TABLE 1

Identification of Open Reading Frames

| Name | Vector | Total Nucleotides in Clone | ORF position | Total Amino Acids in ORF |
|---|---|---|---|---|
| PP2A-1 | PCR2.1 | 1279 | 123–1057 | 311 |
| PP-1 | PCR2.1 | 1014 | 39–950 | 303 |

TABLE 2

Degree of amino acid identity and similarity of PpPP2A-1 and other homologous proteins (GCG Gap program was used: gap penalty: 10; gap extension penalty: 0.1; score matrix: blosum62)

| Swiss-Prot # | Q9XGH7 | Q07100 | Q9SBW3 | P48578 | Q9XF94 |
|---|---|---|---|---|---|
| Protein name | Serine/Threonine Protein Phosphatase PP2A Catalytic Subunit | Serine/Threonine Protein Phosphatase PP2A-3 Catalytic Subunit | Serine/Threonine Protein Phosphatase PP2A-4 Catalytic Subunit | Serine/Threonine Protein Phosphatase PP2A-4 Catalytic Subunit | Serine/Threonine Protein Phosphatase PP2A-2 Catalytic Subunit |
| species | *Nicotiana tabacum* (Common tobacco) | *Arabidopsis thaliana* (Mouse-ear cress) | *Oryza sativa* (Rice) | *Arabidopsis thaliana* (Mouse-ear cress) | *Oryza sativa* (Rice) |
| Identity % | 89% | 88% | 88% | 88% | 88% |
| Similarity % | 92% | 91% | 89% | 91% | 90% |

TABLE 3

Degree of amino acid identity and similarity of PpPP-1 and other homologous proteins (GCG Gap program was used: gap penalty: 10; gap extension penalty: 0.1; score matrix: blosum62)

| Swiss-Prot # | Q42912 | Q9LHE7 | Q9SX52 | Q9U9A3 | O00743 |
|---|---|---|---|---|---|
| Protein name | Serine/threonine protein phosphatase | Phospho-protein Phosphatase | F14I3.5 protein | Protein Phosphatase 6 Catalytic Subunit | Serine/Threonine Protein Phosphatase 6 |
| species | *Malus domestica* (Apple) (*Malus sylvestris*) | *Arabidopsis thaliana* (Mouse-ear cress) | *Arabidopsis thaliana* (Mouse-ear cress) | *Dictyostelium discoideum* (Slime mold). | *Homo sapiens* (Human) |
| Identity % | 91% | 90% | 90% | 72% | 68% |
| Similarity % | 95% | 95% | 95% | 81% | 80% |

Example 6

Cloning of the Full-length *Physcomitrella patens* cDNA Encoding for PpPP2A-1 and PpPP-1

To isolate full-length PpPP2A-1 (SEQ ID NO:2) and PpPP-1 (SEQ ID NO:5) from *Physcomitrella patens*, PCR was performed (as described below in Full-Length Amplification) using the original ESTs described in Example 5 as template since they were full-length. The primers used for amplification are listed below in Table 4.

Full-length Amplification

Full-length clones corresponding PpPP2A-1 (SEQ ID NO:2) and PpPP-1 (SEQ ID NO:5) were obtained by performing polymerase chain reaction (PCR) with gene-specific primers (see Table 4) and the original EST as the template. The conditions for the reaction were standard conditions with PWO DNA polymerase (Roche). PCR was performed according to standard conditions and to manufacturer's protocols (Sambrook et al., 1989 Molecular Cloning, A Laboratory Manual. 2nd Edition. Cold Spring Harbor Laboratory Press. Cold Spring Harbor, N.Y., Biometra T3 Thermocycler). The parameters for the reaction were: five minutes at 94° C. followed by five cycles of one minute at 94° C., one minute at 50° C., and 1.5 minutes at 72° C. This was followed by twenty-five cycles of one minute at 94° C., one minute at 65° C., and 1.5 minutes at 72° C.

The amplified fragments were extracted from agarose gel with a QIAquick Gel Extraction Kit (Qiagen) and ligated into the TOPO pCR 2.1 vector (Invitrogen) following manufacturer's instructions. Recombinant vectors were transformed into Top10 cells (Invitrogen) using standard conditions (Sambrook et al. 1989. Molecular Cloning, A Laboratory Manual. 2nd Edition. Cold Spring Harbor Laboratory Press. Cold Spring Harbor, N.Y.). Transformed cells were selected for on LB agar containing 100 µg/ml carbenicillin, 0.8 mg X-gal (5-bromo-4-chloro-3-indolyl-β-D-galactoside), and 0.8 mg IPTG (isopropylthio-β-D-galactoside) grown overnight at 37° C. White colonies were selected and used to inoculate 3 ml of liquid LB containing 100 µg/ml ampicillin and grown overnight at 37° C. Plasmid DNA was extracted using the QIAprep Spin Miniprep Kit (Qiagen) following manufacturer's instructions. Analyses of subsequent clones and restriction mapping was performed according to standard molecular biology techniques (Sambrook et al., 1989 Molecular Cloning, A Laboratory Manual. 2nd Edition. Cold Spring Harbor Laboratory Press. Cold Spring Harbor, N.Y.).

TABLE 4

Scheme and primers used for cloning of full-length clones

| Gene Name | Cloning site | Cloning method | 5' RACE primer | Full Length primers |
|---|---|---|---|---|
| PpPP2A-1 | XmaI/SacI | PCR of original EST clone | | RC001: 5'ATCCCGGGACGA CATGAGTGTGCCT CCGATATC3' (SEQ ID NO:36) RC002: 5'CTGAGCTCAAGT CCCACTATAAGAA GTAGTCT3' (SEQ ID NO:37) |
| PpPP-1 | XmaI/HpaI | PCR of original EST clone | | RC381: 5'ATCCCGGGAGGA AGGGGACTGGACA CAACGTGATG3' (SEQ ID NO:38) RC382: 5'GCGTTAACGCAC CATATGATGCTTTC CGGTCGTC3' (SEQ ID NO:39 |

Example 7

Engineering Stress-tolerant *Arabidopsis* Plants by Over-expressing the PpPP2A-1 Gene and Repressing the PpPP-1Gene Binary Vector Construction: pBPSJH001

The pLMNC53 (Mankin, 2000, PhD thesis, University of North Carolina) vector was digested with HindIII (Roche) and blunt-end filled with Klenow enzyme and 0.1 mM dNTPs (Roche) according to manufacturer's instructions. This fragment was extracted from an agarose gel with a QIAquick Gel Extraction Kit (Qiagen) according to manufacturer's instructions. The purified fragment was then digested with EcoRI (Roche) and extracted from agarose gel with a QIAquick Gel Extraction Kit (Qiagen) according to manufacturer's instructions. The resulting 1.4 kilobase fragment, the gentamycin cassette, included the nos promoter, aacCI gene, and g7 terminator.

The vector pBlueScript was digested with EcoRI and SmaI (Roche) according to manufacturer's instructions. The resulting fragment was extracted from agarose gel with a QIAquick Gel Extraction Kit (Qiagen) according to manufacturer's instructions. The digested pBlueScript vector and the gentamycin cassette fragments were ligated with T4 DNA Ligase (Roche) according to manufacturer's instructions, joining the two respective EcoRI sites and joining the blunt-ended HindIII site with the SmaI site.

The recombinant vector (pGMBS) was transformed into Top10 cells (Invitrogen) using standard conditions. Transformed cells were selected for on LB agar containing 100 µg/ml carbenicillin, 0.8 mg X-gal (5-bromo-4-chloro-3-indolyl-β-D-galactoside), and 0.8 mg IPTG (isopropylthio-β-D-galactoside), grown overnight at 37° C. White colonies were selected and used to inoculate 3 ml of liquid LB containing 100 µg/ml ampicillin and grown overnight at 37° C. Plasmid DNA was extracted using the QIAprep Spin Miniprep Kit (Qiagen) following manufacturer's instructions. Analyses of subsequent clones and restriction mapping were performed according to standard molecular biology techniques (Sambrook et al. 1989. Molecular Cloning, A Laboratory Manual. 2nd Edition. Cold Spring Harbor Laboratory Press. Cold Spring Harbor, N.Y.).

Both the pGMBS vector and p1bxSuperGUS vector were digested with XbaI and KpnI (Roche) according to manufacturer's instructions, excising the gentamycin cassette from pGMBS and producing the backbone from the p1bxSuperGUS vector. The resulting fragments were extracted from agarose gel with a QIAquick Gel Extraction Kit (Qiagen) according to manufacturer's instructions. These two fragments were ligated with T4 DNA ligase (Roche) according to manufacturer's instructions.

The resulting recombinant vector (pBPSJH001) was transformed into Top10 cells (Invitrogen) using standard conditions. Transformed cells were selected for on LB agar containing 100 µg/ml carbenicillin, 0.8 mg X-gal (5-bromo-4-chloro-3-indolyl-β-D-galactoside) and 0.8 mg IPTG (isopropylthio-β-D-galactoside), grown overnight at 37° C. White colonies were selected and used to inoculate 3 ml of liquid LB containing 100 µg/ml ampicillin and grown overnight at 37° C. Plasmid DNA was extracted using the QIAprep Spin Miniprep Kit (Qiagen) following manufacturer's instructions. Analyses of subsequent clones and restriction mapping were performed according to standard molecular biology techniques (Sambrook et al. 1989. Molecular Cloning, A Laboratory Manual. 2nd Edition. Cold Spring Harbor Laboratory Press. Cold Spring Harbor, N.Y.).

Subcloning of PpPP2A-1 and PpPP-1 into the Binary Vector

The fragments containing the different *Physcomitrella patens* protein phosphatases were excised from the recombinant PCR2.1 TOPO vectors by double digestion with restriction enzymes (see Table 5) according to manufacturer's instructions. The subsequent fragment was excised from agarose gel with a QIAquick Gel Extraction Kit (Qiagen) according to manufacturer's instructions and ligated into the binary vector pBPSJH100, cleaved with appropriate enzymes (see Table 5) and dephosphorylated prior to ligation. The resulting recombinant vector contained the corresponding phosphatase in the sense orientation under the control of the constitutive super promoter.

TABLE 5

Listed are the names of the two constructs of the *Physcomitrella patens* phosphatases used for plant transformation

| Gene | Enzymes used to generate gene fragment | Enzymes used to restrict pBPSJH001 | Binary Vector Construct |
|---|---|---|---|
| PpPP2A-1 | XmaI/SacI | XmaI/SacI | pBPSSH004 |
| PpPP-1 | XmaI/HpaI | XmaI/Ecl136 | pBPSLVM018 |

*Agrobacterium* Transformation

The recombinant vectors were transformed into *Agrobacterium tumefaciens* C58C1 and PMP90 according to standard conditions (Hoefgen and Willmitzer, 1990).

Plant Transformation

*Arabidopsis thaliana* ecotype C24 were grown and transformed according to standard conditions (Bechtold 1993, Acad. Sci. Paris. 316:1194–1199; Bent et al. 1994, Science 265:1856–1860).

Screening of Transformed Plants

T1 seeds were sterilized according to standard protocols (Xiong et al. 1999, Plant Molecular Biology Reporter 17: 159–170). Seeds were plated on ½ Murashige and Skoog media (MS) (Sigma-Aldrich), 0.6% agar and supplemented with 1% sucrose, 150 µg/ml gentamycin (Sigma-Aldrich), and 2 µg/ml benomyl (Sigma-Aldrich). Seeds on plates were vernalized for four days at 4° C. The seeds were germinated in a climatic chamber at an air temperature of 22° C. and light intensity of 40 micromols$^{-1m2}$ (white light; Philips TL 65W/25 fluorescent tube) and 16 hours light and 8 hours dark day length cycle. Transformed seedlings were selected after 14 days and transferred to ½ MS media supplemented with 0.6% agar, 1% sucrose, and allowed to recover for five-seven days.

Drought Tolerance Screening

T1 seedlings were transferred to dry, sterile filter paper in a petri dish and allowed to desiccate for two hours at 80% RH (relative humidity) in a Sanyo Growth Cabinet MLR-350H, micromols$^{-1m2}$ (white light; Philips TL 65W/25 fluorescent tube). The RH was then decreased to 60%, and the seedlings were desiccated further for eight hours. Seedlings were then removed and placed on ½ MS 0.6% agar plates supplemented with 2 µg/ml benomyl (Sigma-Aldrich) and scored after five days. The transgenic plants were screened for their improved drought tolerance.

Under drought stress conditions, PpPP2A-1 over-expressing *Arabidopsis thaliana* plants showed a 62% (8 survivors from 13 stressed plants) survival rate to the stress screening; whereas the untransformed control showed less than a 6% survival rate. The transgenic lines survived the treatment while the wild-type plants were nearly dead or did not survive. It is noteworthy that the analyses of these transgenic lines were performed with T1 plants, and therefore, the results will be better when a homozygous, strong expresser is found.

Freezing Tolerance Screening

Seedlings were moved to petri dishes containing ½ MS 0.6% agar supplemented with 2% sucrose and 2 µg/ml benomyl. After four days, the seedlings were incubated at 4° C. for 1 hour and then covered with shaved ice. The seedlings were then placed in an Environmental Specialist ES2000 Environmental Chamber and incubated for 3.5 hours beginning at −1.0° C., and decreasing −1° C. each hour. The seedlings were then incubated at −5.0° C. for 24 hours and then allowed to thaw at 5° C. for 12 hours. The water was poured off and the seedlings were scored after 5 days.

The transgenic plants are screened for their improved cold tolerance, demonstrating that transgene expression (or repression in the case of PP-1) confers cold tolerance. It is noteworthy that the analyses of these transgenic lines were performed with T1 plants, and therefore, the results will be better when a homozygous, strong expresser is found.

Salt Tolerance Screening

Seedlings were transferred to filter paper soaked in ½ MS and placed on ½ MS 0.6% agar supplemented with 2 µg/ml benomyl the night before the salt tolerance screening. For the salt tolerance screening, the filter paper with the seedlings was moved to stacks of sterile filter paper, soaked in 50 mM NaCl, in a petri dish. After two hours, the filter paper with the seedlings was moved to stacks of sterile filter paper, soaked with 200 mM NaCl, in a petri dish. After two hours, the filter paper with the seedlings was moved to stacks of sterile filter paper, soaked in 600 mM NaCl, in a petri dish. After 10 hours, the seedlings were moved to petri dishes containing ½ MS 0.6% agar supplemented with 2 µg/ml benomyl. The seedlings were scored after 5 days. The transgenic plants are then screened for their improved salt tolerance demonstrating that transgene expression (or repression in the case of PP-1) confers salt tolerance.

Example 8

Detection of the PP2A-1 Transgene in the Transgenic *Arabidopsis* Lines

To check for the presence of the PP2A-1 transgene in transgenic *Arabidopsis* lines, PCR was performed on genomic DNA which contaminates the RNA samples taken as described in Example 9 below. Two and one half microliters of the RNA sample was used in a 50 µl PCR reaction using Taq DNA polymerase (Roche Molecular Biochemicals) according to the manufacturer's instructions.

Binary vector plasmid with each gene cloned in was used as positive control, and the wild-type C24 genomic DNA was used as negative control in the PCR reactions. 10 µl PCR reaction was analyzed on 0.8% agarose—ethidium bromide gel.

PP2A-1: The primers used in the reactions are:

5' CCGTTATCCGAGGTCGAGGTCAGAG 3' (SEQ ID NO:40)

5' CCAGGTCCCGAATGTGGTCCAAGGA 3' (SEQ ID NO:41)

The PCR program was as following: 35 cycles of 1 minute at 94° C., 30 seconds at 62° C. and 1 minute at 72° C., followed by 5 minutes at 72° C. A 0.45 kilobase fragment was produced from the positive control and the transgenic plants.

The transgenes were successfully amplified from the T1 transgenic lines, but not from the wild type C24. This result indicates that the T1 transgenic plants contain at least one copy of the transgenes. There was no indication of existence of either identical or very similar genes in the untransformed *Arabidopsis thaliana* control that could be amplified by this method from the wild-type plants.

Example 9

Detection of the PP2A-1 Transgene mRNA in Transgenic *Arabidopsis* Lines

Transgene expression was detected using RT-PCR. Total RNA was isolated from stress-treated plants using a procedure adapted from Verwoerd et al. (1989 NAR 17:2362). Leaf samples (50–100 mg) were collected and ground to a fine powder in liquid nitrogen. Ground tissue was resuspended in 500 µl of a 80° C., 1:1 mixture, of phenol to extraction buffer (100 mM LiCl, 100 mM Tris pH8, 10 mM EDTA, 1% SDS), followed by brief vortexing to mix. After the addition of 250 µl of chloroform, each sample was vortexed briefly. Samples were then centrifuged for 5 minutes at 12,000×g. The upper aqueous phase was removed to a fresh eppendorf tube. RNA was precipitated by adding $\frac{1}{10}^{th}$ volume 3 M sodium acetate and 2 volumes 95% ethanol. Samples were mixed by inversion and placed on ice for 30 minutes. RNA was pelleted by centrifugation at 12,000×g for 10 minutes. The supernatant was removed and pellets briefly air-dried. RNA sample pellets were resuspended in 10 µl DEPC treated water. To remove contaminating DNA from the samples, each was treated with RNase-free DNase (Roche) according to the manufacturer's recommendations. cDNA was synthesized from total RNA using the Superscript First-Strand Synthesis System for RT-PCR (Gibco-BRL) following manufacturer's recommendations.

PCR amplification of a gene-specific fragment from the synthesized cDNA was performed using Taq DNA polymerase (Roche) and gene-specific primers (see Example 8 for primers) in the following reaction: 1× PCR buffer, 1.5 mM $MgCl_2$, 0.2 µM each primer, 0.2 µM dNTPs, 1 unit polymerase, 5 µl cDNA from synthesis reaction. Amplification was performed under the following conditions: Denaturation, 95° C., 1 minute; annealing, 62° C., 30 seconds; extension, 72° C., 1 minute, 35 cycles; extension, 72° C., 5 minutes; hold, 4° C., forever. PCR products were run on a 1% agarose gel, stained with ethidium bromide, and visualized under UV light using the Quantity-One gel documentation system (Bio-Rad).

Expression of the transgenes was detected in the T1 transgenic line. This result indicated that the transgenes are expressed in the transgenic lines and demonstrated that their gene product improved plant stress tolerance in the transgenic line. In agreement with the previous statement, no expression of identical or very similar endogenous genes could be detected by this method. These results are in agreement with the data from Example 8.

Example 10

Engineering Stress-tolerant Soybean Plants by Over-expressing the PP2A-1 and Repressing the PP-1 Gene The constructs pBPSSH004 and pBPSLVM018 are used to transform soybean as described below.

Seeds of soybean are surface sterilized with 70% ethanol for 4 minutes at room temperature with continuous shaking, followed by 20% (v/v) Clorox supplemented with 0.05% (v/v) Tween for 20 minutes with continuous shaking. Then, the seeds are rinsed 4 times with distilled water and placed on moistened sterile filter paper in a Petri dish at room temperature for 6 to 39 hours. The seed coats are peeled off, and cotyledons are detached from the embryo axis. The embryo axis is examined to make sure that the meristematic region is not damaged. The excised embryo axes are collected in a half-open sterile Petri dish and air-dried to a moisture content less than 20% (fresh weight) in a sealed Petri dish until further use.

*Agrobacterium tumefaciens* culture is prepared from a single colony in LB solid medium plus appropriate antibiotics (e.g. 100 mg/l streptomycin, 50 mg/l kanamycin) followed by growth of the single colony in liquid LB medium to an optical density at 600 nm of 0.8. Then, the bacteria culture is pelleted at 7000 rpm for 7 minutes at room temperature, and resuspended in MS (Murashige and Skoog, 1962) medium supplemented with 100 µM acetosyringone. Bacteria cultures are incubated in this pre-induction medium for 2 hours at room temperature before use. The axis of soybean zygotic seed embryos at approximately 15% moisture content are imbibed for 2 hours at room temperature with the pre-induced *Agrobacterium* suspension culture. The embryos are removed from the imbibition culture and transferred to Petri dishes containing solid MS medium supplemented with 2% sucrose and incubated for 2 days, in the dark at room temperature.

Alternatively, the embryos are placed on top of moistened (liquid MS medium) sterile filter paper in a Petri dish and incubated under the same conditions described above. After this period, the embryos are transferred to either solid or liquid MS medium supplemented with 500 mg/L carbenicillin or 300 mg/L cefotaxime to kill the agrobacteria. The liquid medium is used to moisten the sterile filter paper. The embryos are incubated during 4 weeks at 25° C., under 150 µmol m$^{-2}$ sec$^{-1}$ and 12 hours photoperiod. Once the seedlings have produced roots, they are transferred to sterile metromix soil. The medium of the in vitro plants is washed off before transferring the plants to soil. The plants are kept under a plastic cover for 1 week to favor the acclimatization process. Then the plants are transferred to a growth room where they are incubated at 25° C., under 150 µmol m$^{-2}$ sec$^{-1}$ light intensity and 12 hours photoperiod for about 80 days.

The transgenic plants are then screened for their improved drought, salt and/or cold tolerance according to the screening method described in Example 7 demonstrating that transgene expression confers stress tolerance.

Example 11

Engineering Stress-tolerant Rapeseed/Canola Plants by Over-expressing the PP2A-1 and Repressing PP-1 Genes The constructs pBPSSH004 and pBPSLVM018 are used to transform rapeseed/canola as described below.

The method of plant transformation described herein is also applicable to *Brassica* and other crops. Seeds of canola are surface sterilized with 70% ethanol for 4 minutes at room temperature with continuous shaking, followed by 20% (v/v) Clorox supplemented with 0.05% (v/v) Tween for 20 minutes, at room temperature with continuous shaking. Then, the seeds are rinsed 4 times with distilled water and placed on moistened sterile filter paper in a Petri dish at room temperature for 18 hours. Then the seed coats are removed and the seeds are air dried overnight in a half-open sterile Petri dish. During this period, the seeds lose approximately 85% of its water content. The seeds are then stored at room temperature in a sealed Petri dish until further use. DNA constructs and embryo imbibition are as described in Example 10. Samples of the primary transgenic plants (T0) are analyzed by PCR to confirm the presence of T-DNA. These results are confirmed by Southern hybridization in which DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labelled probe by PCR, and used as recommended by the manufacturer.

The transgenic plants are then screened for their improved stress tolerance according to the screening method described in Example 7 demonstrating that transgene expression confers drought tolerance.

Example 12

Engineering Stress-tolerant Corn Plants by Over-expressing the PP2A-1 and Repressing PP-1 Genes The constructs pBPSSH004 and pBPSLVM018 are used to transform corn as described below.

Transformation of maize (Zea Mays L.) is performed with the method described by Ishida et al. (1996, Nature Biotech 14745–50). Immature embryos are co-cultivated with *Agrobacterium tumefaciens* that carry "super binary" vectors, and transgenic plants are recovered through organogenesis. This procedure provides a transformation efficiency of between 2.5% and 20%. The transgenic plants are then screened for their improved drought, salt and/or cold tolerance according to the screening method described in Example 7 demonstrating that transgene expression confers stress tolerance.

Example 13

Engineering Stress-tolerant Wheat Plants by Over-expressing the PP2A-1 and Repressing PP-1 Genes The constructs pBPSSH004 and pBPSLVM018 are used to transform wheat as described below.

Transformation of wheat is performed with the method described by Ishida et al. (1996, Nature Biotech. 14745–50). Immature embryos are co-cultivated with *Agrobacterium tumefaciens* that carry "super binary" vectors, and transgenic plants are recovered through organogenesis. This procedure provides a transformation efficiency between 2.5% and 20%. The transgenic plants are then screened for their improved stress tolerance according to the screening method described in Example 7 demonstrating that transgene expression confers stress tolerance.

Example 14

Monitoring Changes in mRNA Concentration of PpPP-1 in *Physcomitrella patens* Cultures Cold Treated DNA Microarray Slide Preparation PCR amplification was performed in 96 well plates from selected *Physcomitrella patens* ESTs cloned in the pBluescript vector. The PCR buffer set (Boehringer Mannheim) was employed for PCR reaction. Each PCR reaction mixture contains 10 µl of PCR Buffer without MgCl$_2$, 10 µl of MgSO$_4$, 3 µl of SK-Fwd primer (MWG-Biotech, Sequence: 5'-CGCCAAGCGCGCAATTAACCCTCACT-3' SEQ ID NO:42), 3 µl SK-Rev primer (MWG-Biotech, Sequence: 5'GCGTAATACGACTCACTATAGGGCGA-3' SEQ ID NO:43), 2 µl dNTP, 1 µl Taq DNA polymerase (Roche), 72 µl water and 1 µl DNA template. After denaturing at 95° C. for three minutes, the PCR reactions were performed with 35 cycles of three consecutive steps including denaturing at 95° C. for 45 seconds, annealing at 63° C. for 45 seconds, and elongation at 72° C. for 60 seconds. The last elongation was 72° C. for 10 minutes. The PCR products were then purified with QIAquick PCR purification kit (Qiagen, Inc.), eluted with water and the DNA concentration measured at 260 nm in a spectrophotometer.

2 to 5 µg of each PCR product were dried down and dissolved in 50 µl of DMSO. The PCR products were then formatted from 96 well plates to 384 well plates for printing. Microarray GenIII arrayer (Molecular Dynamics) was employed to print the PCR products to microarray slides (Molecular Dynamics) with the format recommended by the manufacturer. The printed spots were about 290 µm in diameter and were spaced about 320 um from center to center. After printing, the slide was left in the dust free chamber for one hour to dry out. UV cross-link was performed with 600 µJ/mm. The cross-linked slides were ready for hybridization and were stored in dark and dry chambers.

Microarray Probe Synthesis

Total RNA was extracted from cold-treated *Physcomitrella patens* cultures (12 hours at 4° C. in the dark) following the RNA extraction method described in Ausubel et al. (Curr. Prot. in Mol. Biol. 1987, J. Wiley and Sons, New York). Oligotex mRNA midi kit (Qiagen Inc.) was applied to isolate mRNA from total RNA with an approach combining both batch and standard protocol recommended by the manufacturer. After binding the total RNA with Oligotex, the sample was centrifuged at 14,000 g to separate the Oligotex:mRNA with the liquid phase instead of running through a column. After four washes with OW2 buffer as described in batch protocol, the Oligotex:mRNA was resuspended in 400 µl OW2 and then collected by the column as the standard protocol. The mRNA was eluted following standard protocol.

Cy3 and Cy5 labeled cDNA probes were synthesized from mRNA with Superscript Choice System for cDNA synthesis (Gibco BRL). Both oligo-(dT)$_{25}$ primer (Genosys Biotechnologies) and Nonamer primer (Amersham Pharmacia Biotech) were mixed with mRNA to reach a total volume of 20 µl. The mixture was first heated at 70° C. for 10 minutes and then left at room temperature for 15 minutes before transferring to ice. Once the sample is on ice, add 8 µl First Strand Synthesis Buffer, 4 µl 0.1M DTT, 2 µl dNTP (Amersham Pharmacia Biotech), 2 µl Cy3- or Cy5-dCTP (Amersham Pharmacia Biotech), 2 µl RNase Inhibitor (Gibco BRL) and 2 µl SuperScript II Reverse Transcriptase. The first strand synthesis was performed at 42° C. for 8 hours and the mixture was then heated at 94° C. for three minutes after the reaction.

After the first strand synthesis, 4 µl of 2.5M sodium hydroxide was added to the reaction and the mixture was incubated at 37° C. for ten minutes. 20 µl of 2M MOPS (pH 5.0) and 500 µl of PB buffer (Qiagen Inc.) were then added to each reaction. The probe was then purified by the QIAquick PCR Purification Kit (Qiagen Inc.) with the protocol provided by the manufacturer.

cDNA Microarray Hybridization and Washes

The purified Cy3- and Cy5-labeled probes were mixed and vacuum died to give a final volume of 9 µl. 9 µl Microarray Hybridization Solution (Amersham Pharmacia Biotech) and 18 µl Formamide (Sigma) were then added to the cDNA probes to give a final volume of 36 µl. The mixture was applied to the printed microarray slide that was then covered with a clean dust-free cover slide with no air trapped. The hybridization was performed in a hybridization chamber at 42° C. for 16 to 20 hours. After the hybridization, the slides were washed two times with 0.5×SSC, 0.2% SDS at room temperature for 5 minutes and 15 minutes. Two times of stringent washes were performed with 0.25×SSC, 0.1% SDS at 55° C. for 10 and 30 minutes respectively. After the washes, the slides were briefly rinsed with Millipore water and dried under compressed nitrogen.

Scanning, Microarray Data Analysis

The cDNA microarrays were scanned using the microarray GenIII Scanner (Molecular Dynamics) equipped with two laser channels. The scanned images were firstly viewed and adjusted in ImageQuant software (Molecular Dynamics) and then analyzed by ArrayVision software (Molecular Dynamics). The signal intensity for each spot was extracted by ArrayVision software (Molecular Dynamics) and transferred to Excel (Microsoft). The data obtained was normalized by dividing the difference of the intensity value and background and the difference of the control value and background. The ratio was then obtained by dividing the normalized data. The transcript level of PpPP-1 decreased 2 times as compared to the untreated control.

Example 15

Identification of Identical and Heterologous Genes

Gene sequences can be used to identify identical or heterologous genes from cDNA or genomic libraries. Identical genes (e.g. full-length cDNA clones) can be isolated via nucleic acid hybridization using for example cDNA libraries. Depending on the abundance of the gene of interest, 100,000 up to 1,000,000 recombinant bacteriophages are plated and transferred to nylon membranes. After denaturation with alkali, DNA is immobilized on the membrane by e.g. UV cross-linking. Hybridization is carried out at high stringency conditions. In aqueous solution, hybridization and washing is performed at an ionic strength of 1 M NaCl and a temperature of 68° C. Hybridization probes are generated by e.g. radioactive ($^{32}$P) nick transcription labeling (High Prime, Roche, Mannheim, Germany). Signals are detected by autoradiography.

Partially identical or heterologous genes that are related but not identical can be identified in a manner analogous to the above-described procedure using low stringency hybridization and washing conditions. For aqueous hybridization, the ionic strength is normally kept at 1 M NaCl while the temperature is progressively lowered from 68 to 42° C.

Isolation of gene sequences with homologies (or sequence identity/similarity) only in a distinct domain of (for example 10–20 amino acids) can be carried out by using synthetic radio labeled oligonucleotide probes. Radio labeled oligonucleotides are prepared by phosphorylation of the 5-prime end of two complementary oligonucleotides with T4 polynucleotide kinase. The complementary oligonucleotides are annealed and ligated to form concatemers. The double stranded concatemers are than radiolabeled by, for example, nick transcription. Hybridization is normally performed at low stringency conditions using high oligonucleotide concentrations.

Oligonucleotide hybridization solution:
6×SSC
0.01 M sodium phosphate
1 mM EDTA (pH 8)
0.5% SDS
100 µg/ml denatured salmon sperm DNA
0.1% nonfat dried milk During hybridization, temperature is lowered stepwise to 5–10° C. below the estimated oligonucleotide Tm or down to room temperature followed by washing steps and autoradiography. Washing is performed with low stringency such as 3 washing steps using 4× SSC. Further details are described by Sambrook, J. et al. (1989), "Molecular Cloning: A Laboratory Manual", Cold Spring Harbor Laboratory Press or Ausubel, F. M. et al. (1994) "Current Protocols in Molecular Biology", John Wiley & Sons.

Example 16

Identification of Identical Genes by Screening Expression Libraries with Antibodies c-DNA clones can be used to produce recombinant polypeptide for example in *E. coli* (e.g. Qiagen QIAexpress pQE system). Recombinant polypeptides are then normally affinity purified via Ni-NTA affinity chromatography (Qiagen). Recombinant polypeptides are then used to produce specific antibodies for example by using standard techniques for rabbit immunization. Antibodies are affinity purified using a Ni-NTA column saturated with the recombinant antigen as described by Gu et al., 1994 BioTechniques 17:257–262. The antibody can than be used to screen expression cDNA libraries to identify identical or heterologous genes via an immunological screening (Sambrook, J. et al. (1989), "Molecular Cloning: A Laboratory Manual", Cold Spring Harbor Laboratory Press or Ausubel, F. M. et al. (1994) "Current Protocols in Molecular Biology", John Wiley & Sons).

Example 17

In Vivo Mutagenesis

In vivo mutagenesis of microorganisms can be performed by passage of plasmid (or other vector) DNA through *E. coli* or other microorganisms (e.g. *Bacillus* spp. or yeasts such as *Saccharomyces cerevisiae*) that are impaired in their capabilities to maintain the integrity of their genetic information. Typical mutator strains have mutations in the genes for the DNA repair system (e.g., mutHLS, mutD, mutT, etc.; for reference, see Rupp, W. D. (1996) DNA repair mechanisms, in: *Escherichia coli* and *Salmonella*, p. 2277–2294, ASM: Washington.) Such strains are well known to those skilled in the art. The use of such strains is illustrated, for example, in Greener, A. and Callahan, M. (1994) *Strategies* 7: 32–34. Transfer of mutated DNA molecules into plants is preferably done after selection and testing in microorganisms. Transgenic plants are generated according to various examples within the exemplification of this document.

Example 18

In Vitro Analysis of the Function of *Physcomitrella* Genes in Transgenic Organisms The determination of activities and kinetic parameters of enzymes is well established in the art. Experiments to determine the activity of any given altered enzyme must be tailored to the specific activity of the wild-type enzyme, which is well within the ability of one skilled in the art. Overviews about enzymes in general, as well as specific details concerning structure, kinetics, principles, methods, applications and examples for the determination of many enzyme activities may be found, for example, in the following references: Dixon, M., and Webb, E. C., (1979) Enzymes. Longmans: London; Fersht, (1985) Enzyme Structure and Mechanism. Freeman: New York; Walsh, (1979) Enzymatic Reaction Mechanisms. Freeman: San Francisco; Price, N. C., Stevens, L. (1982) Fundamentals of Enzymology. Oxford Univ. Press: Oxford; Boyer, P. D., ed. (1983) The Enzymes, $3^{rd}$ ed. Academic Press: New York; Bisswanger, H., (1994) Enzymkinetik, $2^{nd}$ ed. VCH: Weinheim (ISBN 3527300325); Bergmeyer, H. U., Bergmeyer, J., Graβl, M., eds. (1983–1986) Methods of Enzymatic Analysis, $3^{rd}$ ed., vol. I–XII, Verlag Chemie: Weinheim; and Ullmann's Encyclopedia of Industrial Chemistry (1987) vol. A9, Enzymes. VCH: Weinheim, p. 352–363.

The activity of polypeptides that bind to DNA can be measured by several well-established methods, such as DNA band-shift assays (also called gel retardation assays). The effect of such polypeptides on the expression of other molecules can be measured using reporter gene assays (such as that described in Kolmar, H. et al. (1995) *EMBO J.* 14: 3895–3904 and references cited therein). Reporter gene test systems are well known and established for applications in both prokaryotic and eukaryotic cells, using enzymes such as β-galactosidase, green fluorescent polypeptide, and several others.

The determination of activity of membrane-transport polypeptides can be performed according to techniques such as those described in Gennis, R. B. Pores, Channels and Transporters, in Biomembranes, Molecular Structure and Function, pp. 85–137, 199–234 and 270–322, Springer: Heidelberg (1989).

Example 19

Purification of the Desired Product from Transformed Organisms

Recovery of the desired product from plant material (i.e., *Physcomitrella patents* or *Arabidopsis thaliana*), fungi, algae, ciliates, *C. glutamicum* cells, or other bacterial cells transformed with the nucleic acid sequences described herein, or the supernatant of the above-described cultures can be performed by various methods well known in the art. If the desired product is not secreted from the cells, can be harvested from the culture by low-speed centrifugation, the cells can be lysed by standard techniques, such as mechanical force or sonification. Organs of plants can be separated mechanically from other tissue or organs. Following homogenization cellular debris is removed by centrifugation, and the supernatant fraction containing the soluble polypeptides is retained for further purification of the desired compound. If the product is secreted from desired cells, then the cells are removed from the culture by low-speed centrifugation, and the supernatant fraction is retained for further purification.

The supernatant fraction from either purification method is subjected to chromatography with a suitable resin, in which the desired molecule is either retained on a chromatography resin while many of the impurities in the sample are not, or where the impurities are retained by the resin while the sample is not. Such chromatography steps may be repeated as necessary, using the same or different chromatography resins. One skilled in the art would be well versed in the selection of appropriate chromatography resins and in their most efficacious application for a particular molecule to be purified. The purified product may be concentrated by filtration or ultrafiltration, and stored at a temperature at which the stability of the product is maximized.

There is a wide array of purification methods known to the art and the preceding method of purification is not meant to be limiting. Such purification techniques are described, for example, in Bailey, J. E. & Ollis, D. F. Biochemical Engineering Fundamentals, McGraw-Hill: New York (1986). Additionally, the identity and purity of the isolated compounds may be assessed by techniques standard in the art. These include high-performance liquid chromatography (HPLC), spectroscopic methods, staining methods, thin layer chromatography, NIRS, enzymatic assay, or microbiologically. Such analysis methods are reviewed in: Patek et al., 1994 *Appl. Environ. Microbiol.* 60:133–140; Malakhova et al., 1996 *Biotekhnologiya* 11:27–32; and Schmidt et al., 1998 *Bioprocess Engineer.* 19:67–70. Ulmann's Encyclopedia of Industrial Chemistry, (1996) vol. A27, VCH: Weinheim, p. 89–90, p. 521–540, p. 540–547, p. 559–566, 575–581 and p. 581–587; Michal, G. (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, vol. 17.

Example 20

Identification of PpPP2A-1 Orthologs

The *Brassica napus*, *Glycine max*, and *Oryza sativa* partial cDNAs (ESTs) for BnPP2A-1, BnPP2A-2, BnPP2A-3, GmPP2A-1, GmPP2A-2, GmPP2A-3, GmPP2A-4, GmPP2A-5, OsPP2A-1, OsPP2A-2, OsPP2A-3, OsPP2A-4, and OsPP2A-5 were identified in a privately licensed database by searching for ESTs with similarity to the *Physcomitrella patens* PP2A-1 nucleotide sequence, and the full-length cDNAs of the identified ESTs were sequenced. These particular clones were chosen for further analyses (see Table 6 below).

TABLE 6

| Gene name | Hyseq cloneID | Hyseq source | position for translation | vs. PpPP2A-1 identity/similarity | vs public identity/similarity |
|---|---|---|---|---|---|
| BnPP2A-1 | BN48706417 | canola | 150–1067 | 78%/86% | AAG52565: 96%/97% |
| BnPP2A-2 | BN51288093 | canola | 90–1046 | 42%/54% | AAC39460: 90%/95% |
| BnPP2A-3 | BN51387173 | canola | 155–1036 | 40%/54% | BAB09762: 92%/92% |
| OsPP2A-1 | OS41502678 | rice | 140–1081 | 88%/90% | AAD048068: 99%/99% |
| OsPP2A-2 | OS32806943 | rice | 173–1093 | 79%/86% | AAC72838: 96%/98% |
| OsPP2A-3 | OS35083313 | rice | 208–1155 | 42%/57% | AAA33545: 94%/98% |
| OsPP2A-4 | OS33003814 | rice | 58–978 | 88%/90% | AAD22116: 100%/100% |
| OsPP2A-5 | OS34738749 | rice | 104–1021 | 78%/87% | BAA92697: 78%/87% |
| GmPP2A-1 | GM50770660 | soybean | 97–1005 | 55%/67% | CAA87385: 55%/67% |
| GmPP2A-2 | GM48922444 | soybean | 28–975 | 41%/57% | BAA92244: 41%/57% |
| GmPP2A-3 | GM50131069 | soybean | 206–1144 | 88%/91% | BAA92699: 88%/91% |
| GmPP2A-4 | GM47171610 | soybean | 114–1082 | 43%/56% | CAA05491: 43%/56% |
| GmPP2A-5 | GM49671923 | soybean | 91–1008 | 78%/87% | BAA92697: 78%/87% |

APPENDIX

Nucleotide sequence of the partial PP2A-1 from *Physcomitrella patens* (SEQ ID NO:1)

```
GAAGTCTTCCATACGTGGCATTTCCGTACTTTCGAAGACACTCGTCATAGAAACC

ATACACTTGGGTGATCTGCCGACTCTCATGATTGCCACGCAGAATGGTAATACGA

TCAGGATATCGTACTTTTAAAGCCACTAGCAGTGTAGCAGTTTCAACTGAATAAT

AACCACGATCCACATAATCTCCCATAAATAAGTAATTGGTGTCTGGACACATTCC

TCCAATTCGGAAGAGTTCAGCAAGATCATGAAACTGGCCATGAATATCACCACA

AATTGTGACTGGACACTTCACTGGCTGAACATTATTTTCCCGCATCAATATCTCCT

TCGCCTTCTCACATAGTCCTCTGACCTCGACCTCGGATAACGGTTTGCATTGTATG

AGCTGAGCAATCTGTGTGTCCAGCTGCCCATTAGAGGATATCGGAGGCACACTC

ATGTCGTCCCTCCTGTTGCGCTTCCCCTTCTCCACGCTATCGCCCTACCCTCCGTT

TCCGCTGATCTCCGCCTCAAAAACCAACTCCGACACTCTCGAAACGCAATCTGCA

ACACCGACAACAAAAAGAAAATCACGTGACGAAAGAAAGGGTGAGAAGCAACA

GGGCGAAAAAGAAAATCACGGACGAAAGAAAGGGTGAGATGCAACAGGGCGAG

AGGGGGAACGCAAGAGGAACGACAGAGGAGCGACCTACGGTGAGCTGGTGC
```

Nucleotide sequence of the full-length PpPP2A-1 from *Physcomitrella patens* (SEQ ID NO:2)

```
CTTGTTCTAGGGTTGCGATTGCGTTTCGAGAGTGTCGGAGTTGGTTTTTGAGGCG

GAGATCAGCGGAAACGGAGGGTAGGGCGATAGCGTGGAGAAGGGGAAGCGCAA

CAGGAGGGACGACATGAGTGTGCCTCCGATATCCTCTAATGGGCAGCTGGACAC
```

-continued
APPENDIX

```
ACAGATTGCTCAGCTCATACAATGCAAACCGTTATCCGAGGTCGAGGTCAGAGG

ACTATGTGAGAAGGCGAAGGAGATATTGATGCGGGAAAATAATGTTCAGCCAGT

GAAGTGTCCAGTCACAATTTGTGGTGATATTCATGGCCAGTTTCATGATCTTGCT

GAACTCTTCCGAATTGGAGGAATGTGTCCAGACACCAATTACTTATTTATGGGAG

ATTATGTGGATCGTGGTTATTATTCAGTTGAAACTGCTACACTGCTAGTGGCTTTA

AAAGTACGATATCCTGATCGTATTACCATTCTGCGTGGCAATCATGAGAGTCGGC

AGATCACCCAAGTATGGTTTCTATGACGAGTGTCTTCGAAAGTACGGAAATGC

CAACGTATGGAAGATCTTCACTGACCTGTTTGATTATTTTCCTTTAACAGCACTCG

TAGAGTCGGAGATTTTTTGTTTACATGGAGGGCTTTCGCCAAGCATCGATTCCTT

GGACCACATTCGGGACCTGGATCGAGTTCAAGAGGTTCCTCATGAAGGTCCGAT

GTGTGATCTACTTTGGTCTGACCCCGATGACCGTTGTGGTTGGGGCATTTCTCCCC

GTGGTGCTGGCTACACATTTGGCCAGGATATATCTGAGCAGTTCAATCACAACAA

CAATCTGAAGTTGGTCGCAAGGGCACATCAATTAGTTATGGAGGGCTACAATTG

GGGACATGAACACAAGGTGGTCACTATTTTCAGCGCACCTAATTATTGCTATCGC

TGTGGAAACATGGCTTCTATATTGGAAGTGGATGACAATATGGGCCACACTTTCA

TTCAGTTTGAACCAGCCCCGAGACGAGGTGAACCAGATGTGACAAGGCGCACGC

CAGACTACTTCTTATAGTGGGACTTTCTGATAGTAGTTTTTAAAGTATGCTTTGAG

CTATTTTGGATCGTCTGTAGTCCATGCATTCAATGATGTAGATTTTCCTCAGGTTA

GCATGGTGTTACCAAGCGATAGCAGCCTGAATGCTGTCATAACCGCCACACCAT

CATATGATATGTATTTCATTGAGCGGGCATGCTACTCTGCGCTTGAGATGTAAGC

GAGTCTCTATTTGGAGTG
```

Deduced amino acid sequence of PpPP2A-1 from *Physcomitrella patens* (SEQ ID NO:3)

```
MSVPPISSNGQLDTQIAQLIQCKPLSEVEVRGLCEKAKEILMRENNVQPVKCPVTICG

DIHGQFHDLAELFRIGGMCPDTNYLFMGDYVDRGYYSVETATLLVALKVRYPDRITI

LRGNHESRQITQVYGFYDECLRKYGNANVWKIFTDLFDYFPLTALVESEIFCLHGGLS

PSIDSLDHIRDLDRVQEVPHEGPMCDLLWSDPDDRCGWGISPRGAGYTFGQDISEQF

NHNNNLKLVARAHQLVMEGYNWGHEHKVVTIFSAPNYCYRCGNMASILEVDDNM

GHTFIQFEPAPRRGEPDVTRRTPDYFL*
```

Nucleotide sequence of the partial PpPP-1 from *Physcomitrella patens* (SEQ ID NO:4)

```
GGCACGAGGTTTTAGCTGCGCGCGGAAGAAGCAGCGTGCGCGGCGGTGGTTGTT

TGGTTTTTGTTTCCTGTGTTGCTGTTAGCTGCGCAAAGGAAGGGGACTGGACACA

ACGTGATGGACTTAGATCAGTGGCTTGAGAAAGTGAAGAGCGGCAACTACCTCT

TGGAAGACGAGCTCAAGCAACTATGTGAATATGTGAAAGAAATATTGGTGGAGG

AATCCAATGTTCAGCCTGTCAACAGTCCCGTTACTGTTTGTGGCGATATCCATGG

CCAGTTTCATGACTTGATGAAGCTTTTTCAGACTGGAGGACACGTCCCCAGCACA

AACTACATCTTCATGGGTGATTTTGTGGATCGAGGTTACAACAGTTTGGAAGTAT

TTACAATACTTTTGCTGCTGAAAGCAAGATACCCTGCTCATATGACGTTGTTGAG

GGGTAACCATGAGAGTAGACAGATAACTCAGGTATATGGATTTTATGACGAATG

CCAGCGGAAGT
```

-continued
APPENDIX

Nucleotide sequence of the full-length PpPP-1 from *Physcomitrella patens* (SEQ ID NO:5)

GCCCTTATCCCGGGAGGAAGGGGACTGGACACAACGTGATGGACTTAGATCAGT

GGCTTGAGAAAGTGAAGAGCGGCAACTACCTCTTGGAAGACGAGCTCAAGCAAC

TATGTGAATATGTGAAAGAAATATTGGTGGAGGAATCCAATGTTCAGCCTGTCA

ACAGTCCCGTTACTGTTTGTGGCGATATCCATGGCCAGTTTCATGACTTGATGAA

GCTTTTTCAGACTGGAGGACACGTCCCCAGCACAAACTACATCTTCATGGGTGAT

TTTGTGGATCGAGGTTACAACAGTTTGGAAGTATTTACAATACTTTTGCTGCTGA

AAGCAAGATACCCTGCTCATATGACGTTGTTGAGGGGTAACCATGAGAGTAGAC

AGATAACTCAGGTATATGGATTTTATGACGAATGCCAGCGGAAGTATGGAAACC

CAAATGCTTGGCGGTACTGCACTGATGTTTTTGACTACCTTACACTCTCAGCCAT

AATAGATGGAAGGGTGTTGTGTGTTCATGGAGGTCTGTCTCCAGACATTCGGACA

ATTGATCAGATTAGGGTGATAGAGAGGCAGTGTGAGATTCCTCATGAAGGGCCA

TTCTGTGACTTGATGTGGAGTGATCCTGAGGATATCGAAACTTGGGCTGTTAGCC

CACGAGGTGCTGGGTGGCTTTTTGGTGCACGCGTTACCTCTGAGTTCAATCACAT

AAACGGATTGGAGCTTGTATGCCGTGCGCATCAATTAGTTCAAGAGGGATTGAA

GTACATGTTTCCTGACAAAGGACTTGTCACGGTGTGGTCCGCTCCAAACTATTGC

TACAGATGTGGAAATGTTGCTTCAATCTTAAGCTTCAACGAAAATATGGAGAGA

GATGTGAAATTTTTTACTGAGACCGAGGAGAACCAGGCTATGATGGCACCTCGA

GCAGGAGTTCCTTACTTCTTGTAGAGATATTTGTCGCAGATACCACATGACGACC

GGAAAGCATCATATGGTGCGTTAACGCAAGGGC

Deduced amino acid sequence of PpPP-1 from *Physcomitrella patens* (SEQ ID NO:6)

MDLDQWLEKVKSGNYLLEDELKQLCEYVKEILVEESNVQPVNSPVTVCGDIHGQFHDLMKL

FQTGGHVPSTNYIFMGDFVDRGYNSLEVFTILLLLKARYPAHMTLLRGNHESRQITQVYGFY

DECQRKYGNPNAWRYCTDVFDYLTLSAIIDGRVLCVHGGLSPDIRTIDQIRVIERQCEIPHE

GPFCDLMWSDPEDIETWAVSPRGAGWLFGARVTSEFNHINGLELVCRAHQLVQEGLKYM

FPDKGLVTVWSAPNYCYRCGNVASILSFNENMERDVKFFTETEENQAMMAPRAGVPYFL*

Nucleotide sequence of BnPP2A-1 from *Brassica napus* (SEQ ID NO:7)

TTGAAATTGAAATTCGCATTTTTGCTATGGGAACTGAGTGATGGTAGATAATTCG

AATCCAAATCCGCATCCGGATCCAATACTATCCGAATCCGGATTTTGAGTTTTTGG

TCAGATCGGGGATCGGATCTGAGGGAAGGAGAAGACGATGCCGGAGACGGGAGA

CATCGATCGTCAGATCGAGCAGCTGATGGAGTGTAAAGCGTTGTCCGAGGCGGAG

GTGAAGACGCTGTGCGAGCAAGCGAGGGCGATTCTGGTGGAGGAGTGGAATGTT

CAGCCGGTTAAGTGTCCGGTCACCGTCTGCGGCGACATCCACGGCCAGTTTTACG

ATCTGATTGAGCTTTTTAAGATCGGTGGTTCTTCGCCTGACACCAATTATCTCTTC

ATGGGCGATTACGTAGATCGAGGGTATTATTCTGTGGAGACAGTCTCGCTCTTGG

TAGCACTCAAAGTTCGCTACAGAGATAGGCTTACCATCTTAAGAGGGAATCACGA

AAGCCGCCAAATTACTCAAGTGTATGGATTTTATGATGAGTGCTTGAGAAAATAT

GGAAATGCTAATGTCTGGAAACACTTCACTGACCTTTTTGATTATCTTCCTCTTAC

AGCTCTCATCGAGAGTCAGGTTTTCTGTTTACATGGAGGGCTCTCACCTTCTTTAG

-continued
APPENDIX

```
ATACACTTGACAACATCCGTTCTCTAGATCGAATCCAAGAGGTTCCACATGAAGG

ACCTATGTGTGATCTGTTATGGTCCGATCCAGATGATCGATGCGGTTGGGGAATA

TCTCCTCGTGGCGCAGGCTACACGTTCGGACAAGATATCGCTACTCAGTTTAACC

ACACCAATGGACTCAGTCTGATCTCAAGAGCACACCAACTTGTCATGGAAGGTTA

TAATTGGTGCCAAGAAAAGAACGTTGTGACTGTGTTTAGCGCCCCAAACTATTGC

TACCGATGCGGCAACATGGCTGCTATTCTAGAGATAGACGAGAACATGGACCAG

AACTTCCTTCAGTTCGATCCAGCCCCACGTCAAGTAGAACCCGAAACTACACGCA

AAACTCCAGATTACTTTTTGTAAGTACCCAAAAAGAAAAAAACATCCTTAACCTT

GTTCTGTAATTTCATTTCCTGTTCGTTAAACTCGTAGTTGTCTTTTTGGTTTTTAGTT

AAGAATGTGTAACCTTTTAACTGATACAAAGCGTTACAAAAGATTCTGGTCCATA

TGAATAAGGCAATTGTTGTTGAGAGCTA
```

Deduced amino acid sequence of BnPP2A-1 from *Brassica napus* (SEQ ID NO:8)

```
MPETGDIDRQIEQLMECKALSEAEVKTLCEQARAILVEEWNVQPVKCPVTVCGDIHG

QFYDLIELFKIGGSSPDTNYLFMGDYVDRGYYSVETVSLLVALKVRYRDRLTILRGNH

ESRQITQVYGFYDECLRKYGNANVWKHFTDLFDYLPLTALIESQVFCLHGGLSPSLDT

LDNIRSLDRIQEVPHEGPMCDLLWSDPDDRCWGISPRGAGYTFGQDIATQFNHTNGL

SLISRAHQLVMEGYNWCQEKNVVTVFSAPNYCYRCGNMAAILEIDENMDQNFLQFD

PAPRQVEPETTRKTPDYFL*
```

Nucleotide sequence of BnPP2A-2 from *Brassica napus* (SEQ ID NO:9)

```
ATTTTATTCACCTACTTAACTCTCTCCGTCGTCGGATTTGTATTCGTTTCCGAGAAA

GGGGGTTTAAGGTTTTTAGGCTTGTCGGTACGATGGACGAGAATTTGCTGGACGA

TATAATACGGCGGCTGTTGGAGACTAACAACGGGAAGCAGGTGAAGCTACTCGA

GGCTGAGATACGCCAGCTCTGCTCTGCTTCCAAAGAGGTTTTTCTCAGCCAGCCTA

ATCTCCTCGAGCTCGAGGCTCCTATCAAGATTTGCGGTGATGTTCATGGTCAGTTT

CCAGACCTCTTGCGGTTGTTTGAGTACGGCGGCTACCCTCCAGCTGCAAATTACTT

GTTCCTCGGAGACTACGTTGATCGTGGTAAGCGGAGCATAGAGACCATATGCCTT

CTCCTTGCCTACAAGCTCAAATACAAGCTCAACTTCTTTCTCCTCAGAGGCAATCA

CGAATGCGCTTCTATCAACCGTGTTTACGGCTTCTACGATGAGTGCAAGAGAAGA

TACAACGTGCGCCTGTGGAAGAGTTTCACCGACTGTTTCAACTGCCTCCCCGTTGC

TGCTCTCATCGACGACAAGATCCTCTGTATGCACGGTGGACTTTCTCCTGATCTCA

AGACCTTGGATGATATCAGGCGGATTCCTCGTCCTGTTGATGTTCCTGATCAGGGC

GTCCTTTGTGATTTGTTATGGGCTGATCCTGACAAAGAAATCCAAGGCTGGGGGG

AGAATGACAGAGGTGTGTCTTATACATTTGGTCCCGACAAAGTGGCTGAGTTCCT

TCAGACTCATGACCTTGATCTTGTTTGCCGAGCTCATCAGGTTGTAGAAGATGGAT

ATGAGTTCTTTGCAAAGAGACAACTGGTGACAATATTCTCTGCACCCAACTACTG

TGGTGAGTTTGACAATGCTGGCGCAATGATGAGTGTTGATGATAGTTTGACATGTT

CTTTCCAAATCCTCAAGTCAACTGAGAAGAAAGGAAGATTTGGATACAACAACAA

CGTTCATAGGCCAGGAACCCCACCTCATAAGGGGGGAAAAGGTGGTTGAGATGG

GGGAATCAAGAGAAGAGTGAAGCCGAAGGGTTCGAACTTTATGGTCAATGTAAT
```

-continued
APPENDIX

```
GTAGGTGATTTGAGGCAATACCGTTTGTTGTTTTGTTTGATTGATGCAAAGATTTT
GGTTTTGTTAGATTGTTTTGTAACTGATACGGCATTTTTCAACTTAAGAAAGTTGG
GTTTATAAAAAAAAAAAAAAAAAAAAAAAAAAAAAAAAAA
```

Deduced amino acid sequence of BnPP2A-2 from Brassica napus (SEQ ID NO:10)

```
MDENLLDDIIRRLLETNNGKQVKLLEAEIRQLCSASKEVFLSQPNLLELEAPIKICGDVH
GQFPDLLRLFEYGGYPPAANYLFLGDYVDRGKRSIETICLLLAYKLKYKLNFFLLRGN
HECASINRVYGFYDECKRRYNVRLWKSFTDCFNCLPVAALIDDKILCMHGGLSPDLK
TLDDIRRIPRPVDVPDQGVLCDLLWADPDKEIQGWGENDRGVSYTFGPDKVAEFLQT
HDLDLVCRAHQVVEDGYEFFAKRQLVTIFSAPNYCGEFDNAGAMMSVDDSLTCSFQI
LKSTEKKGRFGYNNNVHRPGTPPHKGGKGG*
```

Nucleotide sequence of BnPP2A-3 from Brassica napus (SEQ ID NO:11)

```
GGCGAAAACTTTTTTGGTCTGAAGATCGAGAAAAGATTTCGAAAATCAAATTTGG
GTTCCTGGGCAATCGATTTATGTCCGAAAGATTGAAGCTTTTGTAAGATAAAAAG
ATCGATTGGTGTTGTTAAGTTTCGATCGCGTGGGGGTCTTTGTAATGACGCAGCAA
GGGCAGGGAAGCATGGACCCTGCCGTTCTCGACGACATCATTCGTCGTTTGTTGG
ATTACAGAAACCCTAAGCCTGGAACCAAACAGGTCATGCTCAACGAGTCTGAGAT
CCGACAGCTTTGCAGCGTGTCTAGAGAGATTTTCCTTCAGCAGCCTAACCTCCTTG
AGCTCGAGGCTCCAATTAAGATCTGTGGTGATATTCATGGACAGTACTCAGATCT
ACTGAGGCTATTTGAGTACGGAGGCTTACCTCCTGCAGCTAACTATCTATTCCTAG
GAGATTACGTGGATCGCGGGAAGCAGAGCCTAGAAACAATCTGCCTTCTCCTTGC
CTACAAGATCAAATACCCTGAGAACTTCTTCCTCCTAAGAGGCAACCACGAATGC
GCTTCCATCAACCGAATCTACGGATTCTACGATGAACGTAAACGCAGGTTCAGTG
TCAGACTCTGGAAAGTGTTTACAGATTCTTTCAACTGCCTCCCTGTAGCTGCTGTA
ATAGACGATAAGATATTGTGTATGCACGGTGGCCTTTCTCCTGATTTGACCAGCGT
GGAACAGATTAAGAACATTAAGCGACCTACCGATGTTCCGGACTCCGGTTTGTTA
TGTGATCTGCTTTGGTCTGATCCGAGCAAAGATGTGAAAGGCTGGGGGATGAATG
ACCGTGGAGTTTCTTACACGTTTGGGCCTGATAAAGTTGCTGAGTTTTTGATAAAG
AATGATATGGATCTCATCTGTCGTGCTCACCAGGTTGTAGAGGATGGTTATGAGTT
CTTTGCGGATAGACAGCTTGTTACTATATTTTCAGCTCCTAATTACTGTGGTGAAT
TCGATAATGCTGGTGCTATGATGAGTGTTGATGAGAGTTAATGTGCTCTTTTCAAA
TTCTTAAGCCTGCGGATCGGAGGCCTCGGTTCTTATGAGTTAGAGCCTCACTGGA
AAGAAGACGAAATTGGCGAGATGAAAACGGGAGAGAGAGAGAGACATTTGA
AACTCCCGGAGACTTTGTCCTGAGGCCTTTGCAAGAAGGCAGGAAAAAAAAACA
CAGTGTTACATGTTATATCATATAATCTTATTTGAACTTTTGTAATTTCTTTTCTCA
AAACTTTTATGTTATTAAAAAAAAAAAAAAAAAAAAAAAAAAAAAAAAAAAAA
AAAA
```

Deduced amino acid sequence of BnPP2A-3 from Brassica napus (SEQ ID NO:12)

```
MTQQGQGSMDPAVLDDIIRRLLDYRNPKPGTKQVMLNESEIRQLCSVSREIFLQQPNL
LELEAPIKICGDIHGQYSDLLRLFEYGGLPPAANYLFLGDYVDRGKQSLETICLLLAYKI
```

-continued
APPENDIX

KYPENFFLLRGNHECASINRIYGFYDERKRRFSVRLWKVFTDSFNCLPVAAVIDDKILC

MHGGLSPDLTSVEQIKNIKRPTDVPDSGLLCDLLWSDPSKDVKGWGMNDRGVSYTFG

PDKVAEFLIKNDMDLICRAHQVVEDGYEFFADRQLVTIFSAPNYCGEFDNAGAMMSV

DES*

Nucleotide sequence of GmPP2A-1 from Glycine Max (SEQ ID NO:13)

CCTAACCCATCGTTCGCACGGAGCCGTGGTGGTTCTGGCTCTGTCCTTTTTTCCTTT

CTCTCGTTACCAGAACCAGAAGAACCATTTGTGGCCAACATGGATTTGGACCAGT

GGATCTCCAAGGTCAAAGAGGGCCAGCATCTTCTTGAAGACGAGCTTCAACTTCT

CTGCGAATATGTAAAAGAGATCCTTATCGAGGAGTCCAATGTGCAGCCTGTCAAT

AGTCCAGTGACTGTTTGTGGTGATATTCATGGTCAATTCCATGATCTAATGAAACT

TTTCCAGACTGGGGGTCATGTGCCTGAGACAAATTATATTTTTATGGGAGACTTTG

TTGATCGAGGTTACAATAGTCTTGAAGTTTTTACCATCCTTTTACTTCTAAAAGCT

AGATACCCAGCTAATATTACTCTTTTACGTGGAAATCATGAAAGTAGACAATTAA

CCCAGGTCTATGGATTTTATGATGAATGCCAGAGGAAGTATGGCAATGCCAATGC

TTGGCGGTATTGTACAGATGTGTTTGACTATTTAACACTTTCTGCAATTATTGATG

GAACTGTGCTTTGTGTTCATGGGGCCTTTCTCCTGACATTCGAACAATTGATCAG

ATAAGGGTCATTGACCGGAACTGTGAAATTCCTCATGAGGGTCCTTTCTGTGATCT

AATGTGGAGTGATCCTGAAGATATTGAAACATGGGCAGTCAGTCCCCGTGGAGCA

GGTTGGCTTTTTGGATCCAGGGTCACTTCGGAGTTCAATCACATAAATAACCTTGA

TCTTGTTTGTCGAGCGCACCAACTCGTTCAGGAAGGCCTTAAGTATATGTTCCAAG

ATAAAGGCCTTGTAACTGTATGGTCTGCACCTAATTACTGTTACCGATGTGGAAAT

GTAGCTTCTATTCTGAGTTTCAATGAAAATATGGAAAGAGAAGTTAAATTTTTCAC

CGAAACAGAGGAGAACAATCAGATGAGAGGGCCCAGGACAGGCGTTCCATATTT

CTTATAAGTTGGTGCAAATTTTGTTTTGAATTTATTGTAAAATTAGACACTCATGT

ATTTATGCTTTGCCTTTTAAAGGTGGATTTTATTGGTCACAAGATTACCAATCAAA

CTATATCTTAGCTCTGGGTCGCACAGATAATTTTATGTTTAAATTTTTATTGAAAA

AAAAAAAAAAAAAAA

Deduced amino acid sequence of GmPP2A-1 from Glycine Max (SEQ ID NO:14)

MDLDQWISKVKEGQHLLEDELQLLCEYVKEILIEESNVQPVNSPVTVCGDIHGQFHDL

MKLFQTGGHVPETNYIFMGDFVDRGYNSLEVFTILLLLKARYPANITLLRGNHESRQL

TQVYGFYDECQRKYGNANAWRYCTDVFDYLTLSAIIDGTVLCVHGGLSPDIRTIDQIR

VIDRNCEIPHEGPFCDLMWSDPEDIETWAVSPRGAGWLFGSRVTSEFNHINNLDLVCR

AHQLVQEGLKYMFQDKGLVTVWSAPNYCYRCGNVASILSFNENMEREVKFFTETEE

NNQMRGPRTGVPYFL*

Nucleotide sequence of GmPP2A-2 from Glycine Max (SEQ ID NO:15)

AAGAAGAAGAGGTTTTGATCGGATGCGATGAGCACACAGGGGCAAGTGATTATT

GATGAGGCGGTTCTGGATGACATAATCCGGCGCTTAACGGAGGTCCGACTGGCCC

GACCCGGCAAGCAGGTTCAGCTCTCCGAGTCTGAGATCAAGCAACTCTGCGTCGC

TTCCAGAGACATCTTCATTAACCAGCCCAATTTGCTTGAACTCGAAGCCCCCATCA

-continued
APPENDIX

```
AGATTTGTGGTGACATTCATGGGCAGTACAGTGATTTGTTAAGGCTATTTGAGTAT
GGGGGTTTGCCTCCTACTGCGAATTATCTCTTTTTGGGGAATACGTGGACCGTGG
GAAGCAGAGCTTAGAAACCATATGTCTTTTGCTTGCGTATAAAATCAAATATCCA
GAAAACTTTTTCCTGTTAAGGGGGAATCATGAGTGTGCTTCCATTAATAGGATTTA
TGGGTTTTATGATGAATGTAAGCGAAGGTTTAACGTGAGGCTTTGGAAAGCCTTT
ACCGACTGTTTTAACTTCCTTCCTGTGGCAGCCCTTATAGATGATAAAATATTGTG
CATGCATGGTGGTCTTTCCCCTGAACTCACAAACTTGGATGAAATCAGGAATCTA
CCTCGTCCTACTGCGATTCCCGACACCGGCTTGCTTTGTGATTTGCTTTGGTCTGAT
CCTGGTAGGGATGTGAAGGGTTGGGGTATGAATGACAGAGGAGTGTCCTACACCT
TTGGCCCTGATAAGGTCGCTGAGTTCTTGACAAAGCATGACTTGGACCTCATTTGT
CGTGCTCATCAGGTTGTAGAGGATGGGTATGAATTCTTTGCTGATAGGCAACTTGT
TACGATATTTTCAGCTCCAAACTATTGTGGTGAATTTGACAATGCTGGTGCGATGA
TGAGTGTGGACGAAAACTTGATGTGCTCATTTCAGATTCTTAAGCCTGCAGAGAA
AAAATCAAAGTTTGTGATGTCAAACAAGATGTGATGGTTGGCACATCACTGTCAA
GTAATTAACCAAGATGTATTCGTGGAGCTAAATTAAATCCTGAAGATTTAGATTG
CATGGTCTTAAGTTCTATCTATTCTGAGGTGATGATGATGAACAAACAAGTTTACT
GCTATAACATCCAGTCAGGCAGTGAGCATGAGGTACTACAAGAGATATTAAGCAC
TGTTGGATGGCCATAAAAGCAAAGGCTTTTATCTTTTTTTTCTTTTCTTGTTTTAT
AATTATTCTGCAACACAATATGTACATATATGTGTTGTAGATGCTCTGGAAATGAC
CTTCTTTGCTCTGAAAGGTCCTCTTAGACTATCGATTTACACTGATAGAGCAGTTT
GTGTTGATGATTGTGGCCAATTTTATCCAGTTAGTAAAGGTGCAATTGATGGATTT
TATGGTTTAAAAAAAAAAAAAAAAAAAA
```

Deduced amino acid sequence of GmPP2A-2 from *Glycine Max* (SEQ ID NO:16)

```
MSTQGQVIIDEAVLDDIIRRLTEVRLARPGKQVQLSESEIKQLCVASRDIFINQPNLLELE
APIKICGDIHGQYSDLLRLFEYGGLPPTANYLFLGEYVDRGKQSLETICLLLAYKIKYPE
NFFLLRGNHECASINRIYGFYDECKRRFNVRLWKAFTDCFNFLPVAALIDDKILCMHG
GLSPELTNLDEIRNLPRPTAIPDTGLLCDLLWSDPGRDVKGWGMNDRGVSYTFGPDK
VAEFLTKHDLDLICRAHQVVEDGYEFFADRQLVTIFSAPNYCGEFDNAGAMMSVDEN
LMCSFQILKPAEKKSKFVMSNKM*
```

Nucleotide sequence of GmPP2A-3 from *Glycine Max* (SEQ ID NO:17)

```
TCTTTCCCTCCACAAGAAAAAAAATCAGAAAAAGGAAATGAGAGATTGTTGGA
CACCGTGCAAATCAAGCACTTTGCTTGTTATTTCACGCGCCCTCTCTCCATTTTGA
CCTCCCTTTCCTCTTCGTTCCCCACTCACTGCAACGGCGCCGGAGATCCGTCGCTC
TCCTCCTCCTCCTCCTCCTCCTCCTCCTCCGCCGCGATGGGCGCCAATTCCAT
GCTCTCCGAGTCCTCTCACGATCTCGACGACCAGATCTCCCAGCTCATGCAGTGC
AAGCCACTCTCCGAGCAACAGGTCAGAGGTTTATGTGAGAAGGCTAAGGAGATTT
TAATGGATGAAAGTAATGTTCAGCCTGTTAAAAGCCCTGTGACAATTTGTGGCGA
TATTCATGGGCAATTTCATGATCTTGCTGAACTGTTTCGAATTGGAGGGAAGTGTC
CAGATACTAACTACTTGTTTATGGGTGATTATGTGGACCGGGGTTATTATTCAGTT
```

-continued
APPENDIX

```
GAGACTGTATCGCTCCTTGTGGCACTGAAAGTTCGGTATCCCCAGCGAATTACTAT

TCTTAGAGGAAACCATGAAAGCCGTCAGATTACTCAAGTATATGGATTTTATGAT

GAATGCCTTAGAAAGTATGGTAATGCTAATGTTTGGAAGACCTTTACAGACCTTTT

TGATTTTTTTCCATTGACTGCATTGGTTGAATCTGAAATATTCTGTTTGCATGGTGG

ACTGTCACCTTCAATTGAGACCCTTGATAACATAAGGAACTTTGATCGTGTTCAAG

AGGTTCCTCATGAAGGCCCCATGTGTGATCTATTGTGGTCTGACCCAGATGACAG

ATGTGGCTGGGGAATTTCTCCTCGTGGTGCTGGATATACTTTTGGCCAGGATATAT

CTGAACAATTCAATCACACTAACAGCCTTAAATTGATTGCTAGAGCTCATCAGCTT

GTTATGGATGGATTTAACTGGGCTCATGAACAAAAGGTGGTTACCATTTTTAGTGC

ACCTAACTACTGTTACCGATGTGGGAACATGGCTTCCATATTGGAGGTTGATGATT

GCAAGGGTCACACATTCATCCAGTTTGAACCTGCTCCTAGGAGAGGAGAACCTGA

TGTCACTCGTAGAACGCCTGATTACTTCTTATAATGTAGCTGTTGAATGTCATACT

GTTATATCATGGTTACCTCTACTGCACTAATTTCAGGTAGTTGCGCATCCTCATAT

CACGAGATTGCTGTAAACATTTAAATCCATGGATATACACGTTCCGTGCTTTTGGG

GGTTGTCCAAAGACTGCTTTGATGTATAATAGGCAGGTAACATTCCACTGATTAC

ACTCGAGGAATTGCTGGACACCTTGTCTGGAGAAGTCGCCAAGATGATGTCATAA

TACGTATTGTTCCAGCAAAATGTGGATATTTTTTGTTTGTTTTTCGTGTTTATTTTT

TGTATCTTATGTTCAGTAACTCCCTTTTATGGCTTTACAAGCTATATGACTGGATTT

TGTTGGTCGTGGATGTTTTTGTCGTGTTCTATCATTTTTCAGTTAAAGTTGCATGAT

ATAGTGAAAAAAAAAAAAAAAAAA
```

Deduced amino acid sequence of GmPP2A-3 from *Glycine Max* (SEQ ID NO:18)

```
MGANSMLSESSHDLDDQISQLMQCKPLSEQQVRGLCEKAKEILMDESNVQPVKSPVTI

CGDIHGQFHDLAELFRIGGKCPDTNYLFMGDYVDRGYYSVETVSLLVALKVRYPQRI

TILRGNHESRQITQVYGFYDECLRKYGNANVWKTFTDLFDFFPLTALVESEIFCLHGGL

SPSIETLDNIRNFDRVQEVPHEGPMCDLLWSDPDDRCGWGISPRGAGYTFGQDISEQF

NHTNSLKLIARAHQLVMDGFNWAHEQKVVTIFSAPNYCYRCGNMASILEVDDCKGH

TFIQFEPAPRRGEPDVTRRTPDYFL*
```

Nucleotide sequence of GmPP2A-4 from *Glycine Max* (SEQ ID NO:19)

```
GCTCACTCTTCCAACTACTACTGTTGTTCTTCTTCGTCGTCTTGGCCTTCGCATCTT

CACAATCACATCCAATAGAGACACGTTGACTTTGCTGGAAGAAGAAGAAGAAGA

GAATGGAACAATCGCTTTTGGATGACATAATCAATCGCCTCCTCGAAGTTCCTAC

CCTACCGGCTAAGCAGGTTCAGCTATCCGAGTCCGAGATCCGTCAACTCTGCGTA

GTTTCCAGAGAAATTTTCTTGCAACAACCTAATTTATTGGAGCTCGAAGCACCTAT

TAAGATTTGTGGTGATGTACATGGGCAATATTCTGATCTTTTAAGGCTTTTTGAGT

ACGGTGGATTACCTCCTGAAGCCAACTATTTGTTTTTGGGGATTATGTTGATCGA

GGGAAGCAGAGTTTAGAAACAATTTGCCTCCTCCTTGCTTATAAAATAAAATATC

CTGAGAACTTTTTCTTGTTAAGGGGAAACCATGAATGTGCTTCTATAAACCGGAT

ATATGGATTTTATGATGAGTGCAAGAGAAGGTTCAATGTAAGGTTATGGAAGACA

TTTACAGACTGCTTCAATTGCCTGCCTGTGGCAGCCCTTGTCGATGAAAAGATTTT
```

-continued
APPENDIX

```
GTGTATGCATGGGGGACTTTCTCCCGACTTAAATAATTTGGACCAAATTAGAAAT
TTACAGCGGCCCACAGATGTTCCTGATACAGGTTTGCTTTGTGATCTGCTTTGGTC
TGACCCGAGCAAAGATGTTCAAGGATGGGGAATGAATGACAGAGGAGTTTCATA
CACATTTGGTGCTGATAAGGTCTCACAATTTCTTCAGAAACATGATCTTGATCTTG
TTTGTCGTGCTCATCAGGTTGTGGAAGATGGATACGAGTTCTTTGCTAATCGACAA
CTTGTAACAATATTTTCAGCACCTAATTATTGTGGGAGTTTGACAATGCTGGTGC
TATGATGAGTGTTGATGAGACGCTAATGTGCTCTTTCCAAATATTAAAGCCAGCT
GATAAAAAAGCAAAGCTCAATTTTGGAAGTACAACCACTGCTAAGCCTGGAAACT
CTCCAGCAGGTGTAAAGGTTGGAAGATATTAGTCCTTCCTGGATGCGAAAGTGTG
AAATTAAATTTGGCTAAAAGATTGCTACTACTACGGATCAGCTTGGGCTTGAACT
CCTAATGGTTGCAAGAAGGGGAAAATCAAGTTCCATTTCGCCTACTATGATATTTT
GGAATTGTAAAATCAAAGAGAACACCATTATGAAGTTTGTAAACCATTGTTTATT
ATTGGTACAAATTTGCATTTCAAGATGGAGAGCCATAATCTCCTTGTCTTCCTTGT
ACACTAATAACTGGTATATTTTCTTAACTGTAAGCTTCACAAGCGTAGATGGATAC
ATCCGAATCTGTTGCTGAGAACCATTTAAAAATGCTTATACGATTTGGCATATATG
GATGGCAGTTGAGGCTGGTGAAAAAAAAAAAAAAAAA
```

Deduced amino acid sequence of GmPP2A-4 from *Glycine Max* (SEQ ID NO:20)

```
MEQSLLDDIINRLLEVPTLPAKQVQLSESEIRQLCVVSREIFLQQPNLLELEAPIKICGDV
HGQYSDLLRLFEYGGLPPEANYLFLGDYVDRGKQSLETICLLLAYKIKYPENFFLLRGN
HECASINRIYGFYDECKRRFNVRLWKTFTDCFNCLPVAALVDEKILCMHGGLSPDLNN
LDQIRNLQRPTDVPDTGLLCDLLWSDPSKDVQGWGMNDRGVSYTFGADKVSQFLQK
HDLDLVCRAHQVVEDGYEFFANRQLVTIFSAPNYCGEFDNAGAMMSVDETLMCSFQI
LKPADKKAKLNFGSTTTAKPGNSPAGVKVGRY*
```

Nucleotide sequence of GmPP2A-5 from *Glycine Max* (SEQ ID NO:21)

```
ACCGTCCCGGTCGCGCCAACCGCCGCAACCCGAAGAAACCGAATCGATCTGAGA
GAAGGTGCGATCTCGGAGGTGGGAGCCAAACGAAACGATGCCGTCTCACGCGGA
TCTGGAGCGACAGATCGAGCAGCTGATGGACTGCAAGCCTCTGTCGGAGTCGGAG
GTGAAGGCGCTGTGCGATCAAGCGAGGACGATTCTTGTGGAGGAGTGGAACGTG
CAACCGGTTAAGTGCCCCGTCACCGTCTGCGGCGATATTCACGGCCAGTTCTACG
ATCTCATCGAGCTGTTTCGGATTGGAGGGAACGCTCCCGATACCAATTATCTCTTC
ATGGGTGATTATGTAGATCGTGGATACTATTCAGTGGAGACTGTTACACTTTTGGT
GGCTTTGAAAGTCCGTTATAGAGATAGAATCACAATTCTCAGGGGAAATCATGAA
AGCCGTCAAATTACTCAAGTGTATGCTTCTATGATGAATGCTTGAGAAAATATG
GAAATGCGAATGTCTGGAAATACTTTACAGACTTGTTTGATTATTTGCCTCTGACT
GCCCTCATTGAGAGTCAGATTTTCTGCTTGCATGGAGGTCTCTCACCTTCTTTGGA
TACACTGGATAACATCAGAGCATTGGATCGTATTCAAGAGGTTCCACATGAAGGA
CCAATGTGTGATCTCTTGTGGTCTGACCCTGATGATCGCTGTGGATGGGGAATATC
TCCACGTGGTGCAGGATACACATTTGGGCAGGATATAGCTGCTCAGTTTAATCAT
ACCAATGGCCTCTCCCTGATATCGAGAGCACATCAGCTTGTTATGGAAGGATTCA
```

-continued
APPENDIX

```
ATTGGTGCCAGGACAAGAATGTGGTGACTGTATTTAGTGCTCCAAATTACTGTTAT

CGATGTGGGAATATGGCTGCCATACTAGAAATAGGAGAGAATATGGATCAGAATT

TTCTTCAGTTTGATCCAGCTCCCAGGCAAATTGAGCCTGACACCACACGCAAGAC

TCCAGATTATTTTTTGTAACTTCATTTATCTGCCTGTTTGTAGTTACTGCTTTCTGC

CATTACTGTAGATGTGTCTTTAAGGAAAGGAGTTTTACTGTGTAAGTGGAGGGTG

GTCATCAACATAATTCTTTCTTTTGGAGTTTACCTGTTGCTGCTGCCGCTGCCTTAT

CTGTACAAGAAACCAATAGAACTGACACATGACACCAATTGGGGTTGTTGTATAT

TTTTGGGAGGAAGCAGCATAACATGGTATATCTTTTCTGTAATCCTTTTTCTTTTCT

TTAAATTAAATCTCAAGTTAAAGAGCAGATTTTTGAGTCCTGACAATGATGTCCTT

TTGAGACTTTTGATGATGCCAAATGAAATTGCAGGTTTTCAAAAAAAAAAAAAAA

A
```

Deduced amino acid sequence of GmPP2A-5 from *Glycine Max* (SEQ ID NO:22)

```
MPSHADLERQIEQLMDCKPLSESEVKALCDQARTILVEEWNVQPVKCPVTVCGDIHG

QFYDLIELFRIGGNAPDTNYLFMGDYVDRGYYSVETVTLLVALKVRYRDRITILRGNH

ESRQITQVYGFYDECLRKYGNANVWKYFTDLFDYLPLTALIESQIFCLHGGLSPSLDTL

DNIRALDRIQEVPHEGPMCDLLWSDPDDRCGWGISPRGAGYTFGQDIAAQFNHTNGL

SLISRAHQLVMEGFNWCQDKNVVTVFSAPNYCYRCGNMAAILEIGENMDQNFLQFDP

APRQIEPDTTRKTPDYFL*
```

Nucleotide sequence of OsPP2A-1 from *Oryza sativa* (SEQ ID NO:23)

```
GCGCCCCCCAACCGCATCTCAATCTCTCTCCTCTCTCTCTCTCCAGCTCGCCTCC

CCCTCGCCGGCGACGAGCTCTCCCCCGGCTAGGGTTAGACCAGGTGCCCCTCTTG

TCTGCGGCGGAGGAGGTGGGAGGAAGGATGGAGGAGTCCGTGGGCTCGCGCGGC

GGCGGCGGCGGCGCCTGGACGCCCAGATCGAGCAGCTCATGGAGTGCCGCCCG

CTCTCCGAGCCCGAGGTCAAGACGTTGTGCGAGAAGGCGAAGGAGATATTGATG

GAAGAAAGCAACGTTCAGCCAGTTAAGAGCCCAGTCACAATTTGTGGTGATATCC

ATGGGCAATTCCATGATCTAGTAGAGCTCTTTCGGATTGGTGGGAAGTGTCCAGA

TACAAATTATTTGTTTATGGGAGATTATGTAGATCGTGGCTACTATTCTGTTGAGA

CTGTTACACTTTTGGTTGCACTGAAGGTGCGCTACCCACAGCGGATTACAATCCTT

CGTGGAAACCATGAGAGTCGGCAGATCACACAGGTGTATGGATTCTACGACGAAT

GCCTACGAAAGTATGGAAGTGCAAATGTCTGGAAGATCTTCACCGATCTTTTTGA

CTATTTTCCATTGACAGCATTGGTTGAATCAGAGATTTTCTGCCTCCATGGTGGTT

TATCGCCATCAATCGACAATCTTGATAGTGTTCGCAGCTTAGATCGTGTTCAAGAG

GTCCCTCATGAGGGACCAATGTGTGATCTTCTATGGTCTGACCCGGATGATCGAT

GCGGTTGGGGCATATCTCCTCGTGGTGCTGGCTACACTTTTGGCCAGGACATATCG

GAGCAGTTTAACCATACCAATAATCTCAAACTTGTAGCCCGGGCTCATCAATTAG

TTATGGAAGGATATAACTGGGCGCACGAACAAAAGGTCGTGACCATATTCAGTGC

ACCTAATTATTGTTATCGCTGTGGCAACATGGCATCCATCCTGGAGGTTGATGACT

GCAGGAATCACACATTTATTCAGTTTGAACCAGCTCCTAGGAGAGGTGAACCAGA

TGTGACACGGAGAACACCTGATTATTTCCTTTAAATTATCTGTTGTAATTTGTATT
```

-continued
APPENDIX

```
GTTTTGTTTCTTTTGTTTCTCTAAGACCGCAATAGTGAGTGCTGGTCAGTAAAATT
TTGTTGGATCCCTTTGGTAACTAAACTGGCCAGCGATAGCATGAGAATGCCGATG
CCCAAAAAAAATGTGAAACTTATGCCCCTCATTGATCATTGTGAGAATGGTGCTG
TCATCCAGGATGCAACGCATTGCATACGATTCAGTCTCTTACCCACCCTTCCCAAG
CCATGTTTAGGTGGCATTGTGTTGACAGATATCAAAATTCCATTTTGGTATAAGCT
GCTTGAGTTATGTATTGGCTGGTTTTGTAACTGATGTGCTTGGACCTTCTATCATT
AATGACAGACAAGCTGATCTCTCGGTTGCGAAAAAAAAAAAAAAAAAA
```

Deduced amino acid sequence of OsPP2A-1 from *Oryza sativa* (SEQ ID NO:24)

```
MEESVGSRGGGGGGLDAQIEQLMECRPLSEPEVKTLCEKAKEILMEESNVQPVKSPVT
ICGDIHGQFHDLVELFRIGGKCPDTNYLFMGDYVDRGYYSVETVTLLVALKVRYPQRI
TILRGNHESRQITQVYGFYDECLRKYGSANVWKIFTDLFDYFPLTALVESEIFCLHGGL
SPSIDNLDSVRSLDRVQEVPHEGPMCDLLWSDPDDRCGWGISPRGAGYTFGQDISEQF
NHTNNLKLVARAHQLVMEGYNWAHEQKVVTIFSAPNYCYRCGNMASILEVDDCRN
HTFIQFEPAPRRGEPDVTRRTPDYFL*
```

Nucleotide sequence of OsPP2A-2 from *Oryza sativa* (SEQ ID NO:25)

```
GAGGCTTGAGCTCCACCTCCACCTCCTCCACCTCCAACCCCCGATCCCCCGCAAA
CCCTAGCCCTCTCCCCCACCCTCCTCGCCGGCGGCGAGCGGCGGCGGCGCGCGGC
GGGACCCGGAGCCCCCAGTAGCGCCTCCTCCGTCCTCCCCTCCCTGAGGTGCGGG
GGAGAGGATGCCGTCGTCGCACGGGGATCTGGACCGGCAGATCGCGCAGCTGCG
GGAGTGCAAGCACCTGGCGGAGGGGGAGGTGAGGGCGCTGTGCGAGCAGGCGAA
GGCCATCCTCATGGAGGAGTGGAACGTGCAGCCGGTGCGGTGCCCCGTCACGGTC
TGCGGCGACATCCACGGCCAGTTCTACGACCTCATCGAGCTCTTCCGCATCGGCG
GCGAGGCGCCCGACACCAACTACCTCTTCATGGGCGACTACGTCGACCGTGGCTA
CTACTCAGTGGAGACTGTTTCGTTGTTGGTGGCTTTGAAAGTACGCTACAGAGATC
GAATTACAATATTGAGAGGAAATCATGAGAGCAGACAAATCACTCAAGTGTACG
GCTTCTACGATGAATGCTTGAGAAAGTATGGAAATGCAAATGTATGGAAATACTT
TACAGACTTGTTTGATTATTTGCCTCTCACAGCTCTTATAGAAAACCAGGTGTTCT
GCCTTCACGGTGGTCTCTCTCCATCATTGGATACTTTAGATAACATCCGTGCTCTT
GATCGTATACAAGAGGTTCCTCATGAAGGACCCATGTGTGATCTTTTGTGGTCTGA
CCCAGATGACAGATGCGGGTGGGAATTTCACCGAGAGGAGCAGGTTATACATTT
GGGCAAGATATCGCTCAACAGTTTAACCATACAAATGGTCTATCTCTCATCTCAA
GGGCACATCAACTTGTAATGGAAGGATTTAATTGGTGTCAGGACAAGAATGTTGT
GACGGTCTTCAGTGCACCAAACTACTGTTATCGCTGTGGTAACATGGCTGCAATTC
TTGAGATTGGCGAAAACATGGATCAGAACTTCCTCCAATTTGATCCAGCTCCTCG
GCAAATTGAACCAGACACAACACGCAAGACTCCCGACTACTTTTTGTAATTTGTG
GTGTTGACAATTTTAACTCACCTGTGTTGATGCTCCTCTCCTCCGCGGTGTCGGGG
TCTGTAGATCTTCTGTCCTTAGATACGGGTTCCACGAGCCCGGCTGTATGTCTCTC
AATTCTTTTGTTTGGAGATTTGTTGCTGCTTCTCAACCTTTATACAAGACGTTAAA
AGTTACATGCACTGGATTTTTTTCTCC
```

-continued
APPENDIX

Deduced amino acid sequence of OsPP2A-2 from Oryza sativa (SEQ ID NO:26)

MPSSHGDLDRQIAQLRECKHLAEGEVRALCEQAKAILMEEWNVQPVRCPVTVCGDIH

GQFYDLIELFRIGGEAPDTNYLFMGDYVDRGYYSVETVSLLVALKVRYRDRITILRGN

HESRQITQVYGFYDECLRKYGNANVWKYFTDLFDYLPLTALIENQVFCLHGGLSPSLD

TLDNIRALDRIQEVPHEGPMCDLLWSDPDDRCGWGISPRGAGYTFGQDIAQQFNHTN

GLSLISRAHQLVMEGFNWCQDKNVVTVFSAPNYCYRCGNMAAILEIGENMDQNFLQ

FDPAPRQIEPDTTRKTPDYFL*

Nucleotide sequence of OsPP2A-3 from Oryza sativa (SEQ ID NO:27)

CCAATGCCAAGAACAAGAAATCAGAGAGCCCAAGCAAAAAATCCAATCCGAATC

CCCTCCAAAAACCCACCAAACAATCTCCTCCATCTCCAAGAACAAGAACAAGAG

AGCATCCTAGAACATTAGGGGATAAAGGAGGAGGAGAAGAAGACCAAGAAAAG

TTTCGAGAGGAGAGGGAGGAGAGTTCAAGAACTTGGAGAGAAGGGGATGGATCC

GGTGTTGCTGGACGACATCATCCGGAGGCTTATCGAGGTGAAGAATCTGAAGCCG

GGGAAGAACGCGCAGCTTTCGGAGTCGGAGATTAAGCAGCTCTGCGCAACCTCCA

AGGAGATCTTCCTGAATCAGCCCAACCTGCTCGAGCTCGAGGCCCCCATCAAAAT

CTGCGGTGATGTTCATGGACAGTATTCTGATCTCCTGAGGCTGTTTGATTATGGTG

GGTATCCACCTCAGTCCAACTATCTCTTCTTGGGCGATTATGTGGACCGGGGAAA

GCAAAGCCTTGAGACGATATGCCTTCTTTTGGCTTATAAGATCAAGTACCCTGAA

AACTTCTTCCTACTCAGAGGCAACCATGAATGTGCATCGGTCAACCGCATCTATG

GATTTTATGACGAGTGCAAGCGCAGATTCAGTGTAAAACTCTGGAAGACTTTTAC

TGACTGTTTTAACTGCTTACCAGTGGCAGCATTGATAGATGAAAAGATTCTTTGTA

TGCACGGAGGTCTTTCTCCAGAGTTGAATAAGCTGGATCAAATACTCAACCTCAA

CCGCCCCACGGATGTGCCTGATACTGGGTTACTTTGTGATCTCCTTTGGTCCGATC

CATCCAATGACGCACAAGGGTGGGCTATGAATGATCGAGGTGTCTCATATACATT

CGGGCCAGACAAAGTGTCTGAATTTCTTGAGAAGCATGATTTAGACCTCATCTGT

CGAGCCCATCAGGTTGTCGAAGATGGGTACGAGTTCTTTGCTAACCGCCAACTTG

TAACAATATTCTCGGCCCCTAATTACTGTGGAGAATTTGATAATGCTGGTGCCATG

ATGAGTGTAGATGATACACTGATGTGCTCTTTTCAAATACTAAAACCAGCGAGGA

AAATGTTGGGTGGTTCCACGAATTCCAAATCCGGCTTCAAGTCACTGAGAGGGTG

GTGACGATGAGCAAAGCTGTGATCTGATCTGCTGGCGCATGTCTTCTACAGCGGC

TGCGACTAACCGGCATTTTCGCCTACAGCTCGGGTCCATAAACAGCGAAGCAGAT

AGAAATGTGTACAACTTTCCAGCCGATGGAACTGTACATCATCGTTCATGTTGGA

TTAACACTTGTTGTAATGTATTATTGGTTTTACCATGCGGATCTCTTATCATATGA

GAGGATGTGAATGAAAACTGTTCTCCCGTCCTCCCCCCTAAATTCAGAAAAGTTC

AGACAGAAGGACTCCAATAAAAATAGCTAGAATCGAATGCTTTTGAACCAAAAA

AAAAAAAAAAAA

Deduced amino acid sequence of OsPP2A-3 from Oryza sativa (SEQ ID NO:28)

MDPVLLDDIIRRLIEVKNLKPGKNAQLSESEIKQLCATSKEIFLNQPNLLELEAPIKICGD

VHGQYSDLLRLFDYGGYPPQSNYLFLGDYVDRGKQSLETICLLLAYKIKYPENFFLLR

GNHECASVNRIYGFYDECKRRFSVKLWKTFTDCFNCLPVAALIDEKILCMHGGLSPEL

NKLDQILNLNRPTDVPDTGLLCDLLWSDPSNDAQGWAMNDRGVSYTFGPDKVSEFL

EKHDLDLICRAHQVVEDGYEFFANRQLVTIFSAPNYCGEFDNAGAMMSVDDTLMCSF

QILKPARKMLGGSTNSKSGFKSLRGW*

Nucleotide sequence of OsPP2A-4 from *Oryza sativa* (SEQ ID NO:29)

GCCGCGCCGAGATCTAGGGTTGGGCGCGCGACGCCCCCCCCCGCGGCGAGG

AGGATGAGCAGCCCCCATGGCGGCCTCGACGACCAGATCGAGCGCCTCATGCAGT

GCAAGCCCCTCCCCGAGCCCGAGGTCAGAGCACTTTGCGAGAAGGCAAAAGAGA

TATTGATGGAGGAGAGCAACGTTCAACCTGTAAAGAGTCCTGTTACAATATGTGG

TGATATTCATGGGCAGTTTCATGACCTTGCAGAACTGTTCCGAATCGGTGGAAAG

TGCCCAGATACAAACTACTTGTTTATGGGAGATTACGTGGATCGTGGTTATTATTC

TGTTGAAACTGTCACGCTTTTGGTGGCTTTAAAGGTTCGTTATCCTCAGCGAATTA

CTATTCTCAGAGGAAACCACGAAAGTCGACAGATCACTCAAGTTTATGGATTCTA

TGACGAGTGCTTAAGGAAGTACGGGAATGCAAATGTGTGGAAAACTTTTACAGAT

CTCTTCGATTACTTCCCCTTGACAGCATTGGTTGAGTCAGAAATATTTTGCCTGCA

TGGTGGATTATCGCCATCCATTGAGACACTTGATAACATACGTAACTTCGATCGTG

TCCAAGAAGTTCCCCATGAAGGGCCCATGTGTGATCTTCTGTGGTCTGATCCAGA

CGATCGATGTGGTTGGGGTATTTCTCCTCGAGGTGCTGGATACACCTTCGGGCAG

GATATATCAGAGCAGTTCAACCATACCAATAATTTAAGACTTATTGCTAGAGCTC

ACCAGTTGGTCATGGAGGGATTCAATTGGGCTCATGAGCAAAAAGTTGTTACCAT

ATTTAGTGCACCTAATTATTGCTATCGCTGTGGGAACATGGCATCAATCTTGGAAG

TTGATGATTGCAGGGAGCATACATTCATCCAGTTTGAGCCAGCCCCAAGAAGGGG

AGAGCCAGATGTAACTCGTAGAACACCTGACTATTTCCTGTGATGTAAAAGTGGT

GGACTGTCTCTGCAGCAAATGTTTGATAGCTAGCTGGGAGGATTCATCGTGTTCTC

ACTTATCTCTAATTGGCTGATGCTTGGCTTGGGGGCTGCAGTGGTGACTCGAAGC

ATCAAGTAGCAAATTTGTATTATGAAAGGAAAACTATTCTCTTTGTATTCATTTTG

TTCGCCTTTCTTCCCCACAAATTTCACCTAATTTTCTTTTTTCTTTTTTCATGATCCT

TGTAGAGATGAACAATGTAGTTGTATGGCTCCCTGTTGAGCCGGTAGGTCTTTCTG

AGTACATCTTGATTTGCCGTACATAATTGCTTGAAAAACAAGTATTAGAATTCTTT

GTGACCAAAAAAAAAAAAAAAAAAA

Deduced amino acid sequence of OsPP2A-4 from *Oryza sativa* (SEQ ID NO:30)

MSSPHGGLDDQIERLMQCKPLPEPEVRALCEKAKEILMEESNVQPVKSPVTICGDIHG

QFHDLAELFRIGGKCPDTNYLFMGDYVDRGYYSVETVTLLVALKVRYPQRITILRGNH

ESRQITQVYGFYDECLRKYGNANVWKTFTDLFDYFPLTALVESEIFCLHGGLSPSIETL

DNIRNFDRVQEVPHEGPMCDLLWSDPDDRCGWGISPRGAGYTFGQDISEQFNHTNNL

RLIARAHQLVMEGFNWAHEQKVVTIFSAPNYCYRCGNMASILEVDDCREHTFIQFEPA

PRRGEPDVTRRTPDYFL*

Nucleotide sequence of OsPP2A-5 from *Oryza sativa* (SEQ ID NO:31)

GCCGTCACCGTCGCGCCAACTGCCGCAAACCGAATAAACCGAATCGATCTGAGAG

-continued
APPENDIX

AAGAAGAAGAAGAAGACGCGATCTCGGAGGTGGGAGCGAAACGAAACGATGCC

GTCTCACGCGGATCTGGAACGACAGATCGAGCAGCTGATGGAGTGCAAGCCTCTG

TCGGAGTCGGAGGTGAAGGCGCTGTGTGATCAAGCGAGGGCGATTCTCGTGGAG

GAATGGAACGTGCAACCGGTGAAGTGCCCCGTCACCGTCTGCGGCGATATTCACG

GCCAGTTTTACGATCTCATCGAGCTGTTTCGGATTGGAGGGAACGCACCCGATAC

CAATTATCTCTTCATGGGTGATTATGTAGATCGTGGATACTATTCAGTGGAGACTG

TTACACTTTTGGTGGCTTTGAAAGTCCGTTACAGAGATAGAATCACAATTCTCAGG

GGAAATCATGAAAGTCGTCAAATTACTCAAGTGTATGGCTTCTATGATGAATGCT

TGAGAAAATATGGAAATGCCAATGTCTGGAAATACTTTACAGACTTGTTTGATTA

TTTACCTCTGACTGCCCTCATTGAGAGTCAGATTTTCTGCTTGCATGGAGGTCTCT

CACCTTCTTTGGATACACTGGATAACATCAGAGCATTGGATCGTATACAAGAGGT

TCCACATGAAGGACCAATGTGTGATCTCTTGTGGTCTGACCCTGATGATCGCTGTG

GATGGGAATATCTCCACGTGGTGCAGGATACACATTTGGACAGGATATAGCTGC

TCAGTTTAATCATACCAATGGTCTCTCCCTGATATCGAGAGCTCATCAGCTTGTTA

TGGAAGGATTCAATTGGTGCCAGGACAAAAATGTGGTGACTGTATTTAGTGCACC

AAATTACTGTTACCGATGTGGGAATATGGCTGCTATACTAGAAATAGGAGAGAAT

ATGGATCAGAATTTCCTTCAGTTTGATCCAGCGCCCAGGCAAATTGAGCCTGACA

CCACACGCAAGACTCCAGATTATTTTTTATAATTTCATTTATCTGCCTGTTTGTAGT

TACTGCTCTCTGCCATTACTGTAGATGTGTCTTTAAGGAAAGGAGTTTTGCTGTTT

AAGTGGAGGGTGGTCATCAACATAATTCTTTCTTTTGGAGTTTACCTCCTGCTGCT

GCCGCTGCCGCTGCCTTATTTGTACAAGAAACCAATAGAACTGACACAAGCCACC

AATTGGGGTTGTATATTTTTGGGAGGAAGCGGTAATAACATGGTATATCTTGTTCT

GTAATCCTTTTTCTTTAAATTGAATCTCAAGTTAGAGAGCAAAAAAAAAAAAAAA

AAA

Deduced amino acid sequence of OsPP2A-5 from *Oryza sativa* (SEQ ID NO:32)

MPSHADLERQIEQLMECKPLSESEVKALCDQARAILVEEWNVQPVKCPVTVCGDIHG

QFYDLIELFRIGGNAPDTNYLFMGDYVDRGYYSVETVTLLVALKVRYRDRITILRGNH

ESRQITQVYGFYDECLRKYGNANVWKYFTDLFDYLPLTALIESQIFCLHGGLSPSLDTL

DNIRALDRIQEVPHEGPMCDLLWSDPDDRCGWGISPRGAGYTFGQDIAAQFNHTNGL

SLISRAHQLVMEGFNWCQDKNVVTVFSAPNYCYRCGNMAAILEIGENMDQNFLQFDP

APRQIEPDTTRKTPDYFL*

---

We claim:

1. An isolated Protein Phosphatase Stress-Related Polypeptide (PPSRP) coding nucleic acid, wherein the nucleic acid comprises a polynucleotide selected from the group consisting of:
   a) a polynucleotide as shown in SEQ ID NO:2;
   b) a polynucleotide encoding a polypeptide as shown in SEQ ID NO:3;
   c) a polynucleotide that hybridizes under high stringent conditions to a full-length polynucleotide sequence as shown in SEQ ID NO:2;

d) a plynucleotide having at least 95% sequence identity to the coding region of the polynucleotide as shown in SEQ ID NO:2; and e) a polynucleotide encoding a polypeptide having at least 95% sequence identity to the polypeptide as shown in SEQ ID NO:3, wherein the PPSRP coding nucleic acid confers drought resistance when transformed into a plant as compared to a wild type variety of the plant.

2. The PPSRP coding nucleic acid of claim 1, wherein the PPSRP coding nucleic acid comprises the polynucleotide as shown in SEQ ID NO:2.

3. The PPSRP coding nucleic acid of claim 1, wherein the PPSRP coding nucleic acid encodes a polypeptide as shown in SEQ ID NO:3.

4. The PPSRP coding nucleic acid of claim 1, wherein the PPSRP coding nucleic acid has at least 95% sequence identity to the polynucleotide as shown in SEQ ID NO:2.

5. The PPSRP coding nucleic acid of claim 1, wherein the PPSRP coding nucleic acid encodes a polypeptide having at least 95% sequence identity to the polypeptide as shown in SEQ ID NO:3.

6. The PPSRP coding nucleic acid of claim 1, wherein the plant is a monocot.

7. The PPSRP coding nucleic acid of claim 1, wherein the plant is a dicot.

8. The PPSRP coding nucleic acid of claim 1, wherein the plant is selected from maize, wheat, rye, oat, triticale, rice, barley, soybean, peanut, cotton, rapeseed, canola, manihot, pepper, sunflower, tagetes, solanaceous plants, potato, tobacco, eggplant, tomato, Vicia species, pea, alfalfa, coffee, cacao, tea, Salix species, oil palm, coconut, perennial grass and a forage crop.

9. A method of producing a transgenic plant containing JPPSRP coding nucleic acid wherein the plant has an increased tolerance to an environmental stress as compared to a wild type variety of the plant comprising, transforming a plant cell with an expression vector comprising the nucleic acid and generating from the plant cell the transgenic plant, wherein the nucleic acid is selected from the group consisting of:

a) a polynucleotide as shown in SEQ ID NO:2;

b) a polynucleotide encoding a polypeptide as shown in SEQ ID NO:3;

c) a polynucleotide that hybridizes under high stringent conditions to a full-length polynucleotide sequence as shown in SEQ ID NO:2;

d) a polynucleotide having at least 95% sequence identity to the coding region of the polynucleotide as shown in SEQ ID NO:2; and e) a polynucleotide encoding a polypeptide having at least 95% sequence identity to the polypeptide as shown in SEQ ID NO:3.

* * * * *

SEQUENCE LISTING

<160> NUMBER OF SEQ ID NOS: 46

<210> SEQ ID NO 1
<211> LENGTH: 708
<212> TYPE: DNA
<213> ORGANISM: Physcomitrella patens

<400> SEQUENCE: 1

```
gaagtcttcc atacgtggca tttccgtact ttcgaagaca ctcgtcatag aaaccataca      60
cttgggtgat ctgccgactc tcatgattgc cacgcagaat ggtaatacga tcaggatatc     120
gtacttttaa agccactagc agtgtagcag tttcaactga ataataacca cgatccacat     180
aatctcccat aaataagtaa ttggtgtctg acacattcc tccaattcgg aagagttcag      240
caagatcatg aaactggcca tgaatatcac acaaattgt gactggacac ttcactggct      300
gaacattatt ttcccgcatc aatatctcct tcgccttctc acatagtcct ctgacctcga     360
cctcggataa cggtttgcat gtatgagct gagcaatctg tgtgtccagc tgcccattag      420
aggatatcgg aggcacactc atgtcgtccc tcctgttgcg cttcccttc tccacgctat      480 cgccctaccc tccgtttccg ctgatctccg cctcaaaaac caactccgac actctcgaaa     540
cgcaatctgc aacaccgaca acaaaaagaa aatcacgtga cgaaagaaag ggtgagaagc     600
aacagggcga aaagaaaat cacggacgaa agaaagggtg agatgcaaca gggcgagagg      660
gggaacgcaa gaggaacgac agaggagcga cctacggtga gctggtgc                 708
```

<210> SEQ ID NO 2
<211> LENGTH: 1279
<212> TYPE: DNA
<213> ORGANISM: Physcomitrella patens

<400> SEQUENCE: 2

```
cttgttctag ggttgcgatt gcgtttcgag agtgtcggag ttggtttttg aggcggagat      60
cagcggaaac ggagggtagg gcgatagcgt ggagaagggg aagcgcaaca ggagggacga    120
catgagtgtg cctccgatat cctctaatgg gcagctggac acacagattg ctcagctcat    180
acaatgcaaa ccgttatccg aggtcgaggt cagaggacta tgtgagaagg cgaaggagat    240
attgatgcgg gaaaataatg ttcagccagt gaagtgtcca gtcacaattt gtggtgatat    300
tcatggccag tttcatgatc ttgctgaact cttccgaatt ggaggaatgt gtccagacac    360
caattactta tttatgggag attatgtgga tcgtggttat tattcagttg aaactgctac    420
actgctagtg gctttaaaag tacgatatcc tgatcgtatt accattctgc gtggcaatca    480
tgagagtcgg cagatcaccc aagtgtatgg tttctatgac gagtgtcttc gaaagtacgg    540
aaatgccaac gtatggaaga tcttcactga cctgtttgat tattttcctt taacagcact    600
cgtagagtcg gagattttt gtttacatgg agggctttcg ccaagcatcg attccttgga    660
ccacattcgg gacctggatc gagttcaaga ggttcctcat gaaggtccga tgtgtgatct    720
actttggtct gaccccgatg accgttgtgg ttggggcatt tctccccgtg gtgctggcta    780
cacatttggc caggatatat ctgagcagtt caatcacaac aacaatctga gttggtcgc    840 aagggcacat caattagtta tggagggcta caattgggga catgaacaca aggtggtcac    900 tatttttcagc gcacctaatt attgctatcg ctgtggaaac atggcttcta tattggaagt    960
ggatgacaat atgggccaca ctttcattca gtttgaacca gccccgagac gaggtgaacc   1020
agatgtgaca aggcgcacgc cagactactt cttatagtgg gacttctga tagtagtttt   1080 taaagtatgc tttgagctat tttggatcgt ctgtagtcca tgcattcaat gatgtagatt   1140
ttcctcaggt tagcatggtg ttaccaagcg atagcagcct gaatgctgtc ataaccgcca   1200
caccatcata tgatatgtat ttcattgagc gggcatgcta ctctgcgctt gagatgtaag   1260
cgagtctcta tttggagtg                                                1279
```

<210> SEQ ID NO 3

<211> LENGTH: 311
<212> TYPE: PRT
<213> ORGANISM: Physcomitrella patens

<400> SEQUENCE: 3

```
Met Ser Val Pro Pro Ile Ser Ser Asn Gly Gln Leu Asp Thr Gln Ile
  1               5                  10                  15

Ala Gln Leu Ile Gln Cys Lys Pro Leu Ser Glu Val Glu Val Arg Gly
                 20                  25                  30

Leu Cys Glu Lys Ala Lys Glu Ile Leu Met Arg Glu Asn Asn Val Gln
             35                  40                  45

Pro Val Lys Cys Pro Val Thr Ile Cys Gly Asp Ile His Gly Gln Phe
 50                  55                  60

His Asp Leu Ala Glu Leu Phe Arg Ile Gly Gly Met Cys Pro Asp Thr
 65                  70                  75                  80

Asn Tyr Leu Phe Met Gly Asp Tyr Val Asp Arg Gly Tyr Tyr Ser Val
                 85                  90                  95

Glu Thr Ala Thr Leu Leu Val Ala Leu Lys Val Arg Tyr Pro Asp Arg
            100                 105                 110

Ile Thr Ile Leu Arg Gly Asn His Glu Ser Arg Gln Ile Thr Gln Val
            115                 120                 125

Tyr Gly Phe Tyr Asp Glu Cys Leu Arg Lys Tyr Gly Asn Ala Asn Val
130                 135                 140

Trp Lys Ile Phe Thr Asp Leu Phe Asp Tyr Phe Pro Leu Thr Ala Leu
145                 150                 155                 160

Val Glu Ser Glu Ile Phe Cys Leu His Gly Gly Leu Ser Pro Ser Ile
                165                 170                 175

Asp Ser Leu Asp His Ile Arg Asp Leu Asp Arg Val Gln Glu Val Pro
            180                 185                 190

His Glu Gly Pro Met Cys Asp Leu Leu Trp Ser Asp Pro Asp Asp Arg
            195                 200                 205

Cys Gly Trp Gly Ile Ser Pro Arg Gly Ala Gly Tyr Thr Phe Gly Gln
210                 215                 220

Asp Ile Ser Glu Gln Phe Asn His Asn Asn Leu Lys Leu Val Ala
225                 230                 235                 240

Arg Ala His Gln Leu Val Met Glu Gly Tyr Asn Trp Gly His Glu His
                245                 250                 255

Lys Val Val Thr Ile Phe Ser Ala Pro Asn Tyr Cys Tyr Arg Cys Gly
            260                 265                 270

Asn Met Ala Ser Ile Leu Glu Val Asp Asp Asn Met Gly His Thr Phe
            275                 280                 285

Ile Gln Phe Glu Pro Ala Pro Arg Arg Gly Glu Pro Asp Val Thr Arg
            290                 295                 300

Arg Thr Pro Asp Tyr Phe Leu
305                 310
```

<210> SEQ ID NO 4
<211> LENGTH: 502
<212> TYPE: DNA
<213> ORGANISM: Physcomitrella patens

<400> SEQUENCE: 4

```
ggcacgaggt tttagctgcg cgcggaagaa gcagcgtgcg cggcggtggt tgtttggttt    60
ttgtttcctg tgttgctgtt agctgcgcaa aggaagggga ctggacacaa cgtgatggac   120
ttagatcagt ggcttgagaa agtgaagagc ggcaactacc tcttggaaga cgagctcaag   180
```

```
caactatgtg aatatgtgaa agaaatattg gtggaggaat ccaatgttca gcctgtcaac      240
agtcccgtta ctgtttgtgg cgatatccat ggccagtttc atgacttgat gaagcttttt      300
cagactggag gacacgtccc cagcacaaac tacatcttca tgggtgattt tgtggatcga      360
ggttacaaca gtttggaagt atttacaata cttttgctgc tgaaagcaag ataccctgct      420
catatgacgt tgttgagggg taaccatgag agtagacaga taactcaggt atatggattt      480
tatgacgaat gccagcggaa gt                                               502

<210> SEQ ID NO 5
<211> LENGTH: 1014
<212> TYPE: DNA
<213> ORGANISM: Physcomitrella patens

<400> SEQUENCE: 5
gcccttatcc cgggaggaag gggactggac acaacgtgat ggacttagat cagtggcttg       60
agaaagtgaa gagcggcaac tacctcttgg aagacgagct caagcaacta tgtgaatatg      120
tgaaagaaat attggtggag gaatccaatg ttcagcctgt caacagtccc gttactgttt      180
gtggcgatat ccatggccag tttcatgact tgatgaagct ttttcagact ggaggacacg      240
tccccagcac aaactacatc ttcatgggtg attttgtgga tcgaggttac aacagtttgg      300
aagtatttac aatacttttg ctgctgaaag caagataccc tgctcatatg acgttgttga      360
ggggtaacca tgagagtaga cagataactc aggtatatgg attttatgac gaatgccagc      420
ggaagtatgg aaacccaaat gcttggcggt actgcactga tgttttttgac taccttacac      480 tctcagccat aatagatgga agggtgttgt gtgttcatgg aggtctgtct ccagacattc      540
ggacaattga tcagattagg gtgatagaga ggcagtgtga gattcctcat gaagggccat      600
tctgtgactt gatgtggagt gatcctgagg atatcgaaac ttgggctgtt agcccacgag      660
gtgctgggtg gcttttttggt gcacgcgtta cctctgagtt caatcacata aacggattgg      720
agcttgtatg ccgtgcgcat caattagttc aagagggatt gaagtacatg tttcctgaca      780
aaggacttgt cacggtgtgg tccgctccaa actattgcta cagatgtgga atgttgcttt      840
caatcttaag cttcaacgaa aatatggaga gagatgtgaa atttttttact gagaccgagg      900 agaaccaggc tatgatggca cctcgagcag gagttcctta cttcttgtag agatatttgt      960
cgcagatacc acatgacgac cggaaagcat catatggtgc gttaacgcaa gggc           1014

<210> SEQ ID NO 6
<211> LENGTH: 303
<212> TYPE: PRT
<213> ORGANISM: Physcomitrella patens

<400> SEQUENCE: 6

Met Asp Leu Asp Gln Trp Leu Glu Lys Val Lys Ser Gly Asn Tyr Leu
  1               5                  10                  15

Leu Glu Asp Glu Leu Lys Gln Leu Cys Glu Tyr Val Lys Glu Ile Leu
                 20                  25                  30

Val Glu Glu Ser Asn Val Gln Pro Val Asn Ser Pro Thr Val Cys
             35                  40                  45

Gly Asp Ile His Gly Gln Phe His Asp Leu Met Lys Leu Phe Gln Thr
         50                  55                  60

Gly Gly His Val Pro Ser Thr Asn Tyr Ile Phe Met Gly Asp Phe Val
 65                  70                  75                  80

Asp Arg Gly Tyr Asn Ser Leu Glu Val Phe Thr Ile Leu Leu Leu Leu
```

```
                        85                  90                  95
Lys Ala Arg Tyr Pro Ala His Met Thr Leu Leu Arg Gly Asn His Glu
            100                 105                 110

Ser Arg Gln Ile Thr Gln Val Tyr Gly Phe Tyr Asp Glu Cys Gln Arg
            115                 120                 125

Lys Tyr Gly Asn Pro Asn Ala Trp Arg Tyr Cys Thr Asp Val Phe Asp
            130                 135                 140

Tyr Leu Thr Leu Ser Ala Ile Ile Asp Gly Arg Val Leu Cys Val His
145                 150                 155                 160

Gly Gly Leu Ser Pro Asp Ile Arg Thr Ile Asp Gln Ile Arg Val Ile
                165                 170                 175

Glu Arg Gln Cys Glu Ile Pro His Glu Gly Pro Phe Cys Asp Leu Met
            180                 185                 190

Trp Ser Asp Pro Glu Asp Ile Glu Thr Trp Ala Val Ser Pro Arg Gly
            195                 200                 205

Ala Gly Trp Leu Phe Gly Ala Arg Val Thr Ser Glu Phe Asn His Ile
            210                 215                 220

Asn Gly Leu Glu Leu Val Cys Arg Ala His Gln Leu Val Gln Glu Gly
225                 230                 235                 240

Leu Lys Tyr Met Phe Pro Asp Lys Gly Leu Val Thr Val Trp Ser Ala
                245                 250                 255

Pro Asn Tyr Cys Tyr Arg Cys Gly Asn Val Ala Ser Ile Leu Ser Phe
            260                 265                 270

Asn Glu Asn Met Glu Arg Asp Val Lys Phe Phe Thr Glu Thr Glu Glu
            275                 280                 285

Asn Gln Ala Met Met Ala Pro Arg Ala Gly Val Pro Tyr Phe Leu
            290                 295                 300

<210> SEQ ID NO 7
<211> LENGTH: 1243
<212> TYPE: DNA
<213> ORGANISM: Brassica napus

<400> SEQUENCE: 7
ttgaaattga aattcgcatt tttgctatgg ggaactgagt gatggtagat aattcgaatc     60
caaatccgca tccggatcca atactatccg aatccggatt ttgagttttt ggtcagatcg    120
gggatcggat ctgagggaag gagaagacga tgccggagac gggagacatc gatcgtcaga    180
tcgagcagct gatggagtgt aaagcgttgt ccgaggcgga ggtgaagacg ctgtgcgagc    240
aagcgagggc gattctggtg gaggagtgga atgttcagcc ggttaagtgt ccggtcaccg    300
tctgcggcga catccacggc cagttttacg atctgattga ctttttaag atcggtggtt    360 cttcgcctga caccaattat ctcttcatgg gcgattacgt agatcgaggg tattattctg    420
tggagacagt ctcgctcttg gtagcactca aagttcgcta cagagatagg cttaccatct    480
taagagggaa tcacgaaagc cgccaaatta ctcaagtgta tggattttat gatgagtgct    540
tgagaaaata tggaaatgct aatgtctgga acacttcac tgaccttttt gattatcttc    600
ctcttacagc tctcatcgag agtcaggttt ctgtttaca tggagggctc tcaccttctt    660
tagatacact tgacaacatc cgttctctag atcgaatcca agaggttcca catgaaggac    720
ctatgtgtga tctgttatgg tccgatccag atgatcgatg cggttgggga atatctcctc    780
gtggcgcagg ctacacgttc ggacaagata tcgctactca gtttaaccac accaatggac    840
tcagtctgat ctcaagagca caccaacttg tcatggaagg ttataattgg tgccaagaaa    900
```

-continued

```
agaacgttgt gactgtgttt agcgccccaa actattgcta ccgatgcggc aacatggctg      960
ctattctaga gatagacgag aacatggacc agaacttcct tcagttcgat ccagccccac     1020
gtcaagtaga acccgaaact acacgcaaaa ctccagatta cttttttgtaa gtacccaaaa    1080 agaaaaaaac atccttaacc ttgttctgta atttcatttc ctgttcgtta aactcgtagt    1140 tgtcttttttg gttttttagtt aagaatgtgt aaccttttaa ctgatacaaa gcgttacaaa   1200
agattctggt ccatatgaat aaggcaattg ttgttgagag cta                       1243
```

<210> SEQ ID NO 8
<211> LENGTH: 306
<212> TYPE: PRT
<213> ORGANISM: Brassica napus

<400> SEQUENCE: 8

```
Met Pro Glu Thr Gly Asp Ile Asp Arg Gln Ile Glu Gln Leu Met Glu
 1               5                  10                  15

Cys Lys Ala Leu Ser Glu Ala Glu Val Lys Thr Leu Cys Glu Gln Ala
             20                  25                  30

Arg Ala Ile Leu Val Glu Glu Trp Asn Val Gln Pro Val Lys Cys Pro
         35                  40                  45

Val Thr Val Cys Gly Asp Ile His Gly Gln Phe Tyr Asp Leu Ile Glu
     50                  55                  60

Leu Phe Lys Ile Gly Gly Ser Ser Pro Asp Thr Asn Tyr Leu Phe Met
 65                  70                  75                  80

Gly Asp Tyr Val Asp Arg Gly Tyr Tyr Ser Val Glu Thr Val Ser Leu
                 85                  90                  95

Leu Val Ala Leu Lys Val Arg Tyr Arg Asp Arg Leu Thr Ile Leu Arg
            100                 105                 110

Gly Asn His Glu Ser Arg Gln Ile Thr Gln Val Tyr Gly Phe Tyr Asp
        115                 120                 125

Glu Cys Leu Arg Lys Tyr Gly Asn Ala Asn Val Trp Lys His Phe Thr
    130                 135                 140

Asp Leu Phe Asp Tyr Leu Pro Leu Thr Ala Leu Ile Glu Ser Gln Val
145                 150                 155                 160

Phe Cys Leu His Gly Gly Leu Ser Pro Ser Leu Asp Thr Leu Asp Asn
                165                 170                 175

Ile Arg Ser Leu Asp Arg Ile Gln Glu Val Pro His Glu Gly Pro Met
            180                 185                 190

Cys Asp Leu Leu Trp Ser Asp Pro Asp Asp Arg Cys Gly Trp Gly Ile
        195                 200                 205

Ser Pro Arg Gly Ala Gly Tyr Thr Phe Gly Gln Asp Ile Ala Thr Gln
    210                 215                 220

Phe Asn His Thr Asn Gly Leu Ser Leu Ile Ser Arg Ala His Gln Leu
225                 230                 235                 240

Val Met Glu Gly Tyr Asn Trp Cys Gln Glu Lys Asn Val Val Thr Val
                245                 250                 255

Phe Ser Ala Pro Asn Tyr Cys Tyr Arg Cys Gly Asn Met Ala Ala Ile
            260                 265                 270

Leu Glu Ile Asp Glu Asn Met Asp Gln Asn Phe Leu Gln Phe Asp Pro
        275                 280                 285

Ala Pro Arg Gln Val Glu Pro Glu Thr Thr Arg Lys Thr Pro Asp Tyr
    290                 295                 300

Phe Leu
305
```

<210> SEQ ID NO 9
<211> LENGTH: 1259
<212> TYPE: DNA
<213> ORGANISM: Brassica napus

<400> SEQUENCE: 9

```
attttattca cctacttaac tctctccgtc gtcggatttg tattcgtttc cgagaaaggg    60
ggtttaaggt ttttaggctt gtcggtacga tggacgagaa tttgctggac gatataatac   120
ggcggctgtt ggagactaac aacgggaagc aggtgaagct actcgaggct gagatacgcc   180
agctctgctc tgcttccaaa gaggtttttc tcagccagcc taatctcctc gagctcgagg   240
ctcctatcaa gatttgcggt gatgttcatg gtcagtttcc agacctcttg cggttgtttg   300
agtacggcgg ctaccctcca gctgcaaatt acttgttcct cggagactac gttgatcgtg   360
gtaagcggag catagagacc atatgccttc tccttgccta caagctcaaa tacaagctca   420
acttctttct cctcagaggc aatcacgaat gcgcttctat caaccgtgtt tacggcttct   480
acgatgagtg caagagaaga tacaacgtgc gcctgtggaa gagtttcacc gactgtttca   540
actgcctccc cgttgctgct ctcatcgacg acaagatcct ctgtatgcac ggtggacttt   600
ctcctgatct caagaccttg gatgatatca ggcggattcc tcgtcctgtt gatgttcctg   660
atcagggcgt cctttgtgat tgttatggg ctgatcctga caagaaatc caaggctggg   720
gggagaatga cagaggtgtg tcttatacat ttggtcccga caagtggct gagttccttc   780
agactcatga ccttgatctt gtttgccgag ctcatcaggt tgtagaagat ggatatgagt   840
tctttgcaaa gagacaactg gtgacaatat tctctgcacc caactactgt ggtgagtttg   900
acaatgctgg cgcaatgatg agtgttgatg atagtttgac atgttctttc caaatcctca   960
agtcaactga gaagaaagga agatttggat acaacaacaa cgttcatagg ccaggaaccc  1020
cacctcataa ggggggaaaa ggtggttgag atggggggaat caagagaaga gtgaagccga  1080
agggttcgaa ctttatggtc aatgtaatgt aggtgatttg aggcaatacc gtttgttgtt  1140
ttgttttgatt gatgcaaaga ttttggtttt gttagattgt tttgtaactg atacggcatt  1200
tttcaactta agaaagttgg gtttataaaa aaaaaaaaaa aaaaaaaaaa aaaaaaaa    1259
```

<210> SEQ ID NO 10
<211> LENGTH: 319
<212> TYPE: PRT
<213> ORGANISM: Brassica napus

<400> SEQUENCE: 10

```
Met Asp Glu Asn Leu Leu Asp Asp Ile Ile Arg Arg Leu Leu Glu Thr
  1               5                  10                  15

Asn Asn Gly Lys Gln Val Lys Leu Leu Glu Ala Glu Ile Arg Gln Leu
             20                  25                  30

Cys Ser Ala Ser Lys Glu Val Phe Leu Ser Gln Pro Asn Leu Leu Glu
         35                  40                  45

Leu Glu Ala Pro Ile Lys Ile Cys Gly Asp Val His Gly Gln Phe Pro
     50                  55                  60

Asp Leu Leu Arg Leu Phe Glu Tyr Gly Gly Tyr Pro Pro Ala Ala Asn
 65                  70                  75                  80

Tyr Leu Phe Leu Gly Asp Tyr Val Asp Arg Gly Lys Arg Ser Ile Glu
                 85                  90                  95

Thr Ile Cys Leu Leu Leu Ala Tyr Lys Leu Lys Tyr Lys Leu Asn Phe
            100                 105                 110
```

Phe Leu Leu Arg Gly Asn His Glu Cys Ala Ser Ile Asn Arg Val Tyr
        115                 120                 125

Gly Phe Tyr Asp Glu Cys Lys Arg Arg Tyr Asn Val Arg Leu Trp Lys
130                 135                 140

Ser Phe Thr Asp Cys Phe Asn Cys Leu Pro Val Ala Ala Leu Ile Asp
145                 150                 155                 160

Asp Lys Ile Leu Cys Met His Gly Gly Leu Ser Pro Asp Leu Lys Thr
                165                 170                 175

Leu Asp Asp Ile Arg Arg Ile Pro Arg Pro Val Asp Val Pro Asp Gln
                180                 185                 190

Gly Val Leu Cys Asp Leu Leu Trp Ala Asp Pro Asp Lys Glu Ile Gln
                195                 200                 205

Gly Trp Gly Glu Asn Asp Arg Gly Val Ser Tyr Thr Phe Gly Pro Asp
            210                 215                 220

Lys Val Ala Glu Phe Leu Gln Thr His Asp Leu Asp Leu Val Cys Arg
225                 230                 235                 240

Ala His Gln Val Val Glu Asp Gly Tyr Glu Phe Phe Ala Lys Arg Gln
                245                 250                 255

Leu Val Thr Ile Phe Ser Ala Pro Asn Tyr Cys Gly Glu Phe Asp Asn
                260                 265                 270

Ala Gly Ala Met Met Ser Val Asp Asp Ser Leu Thr Cys Ser Phe Gln
                275                 280                 285

Ile Leu Lys Ser Thr Glu Lys Lys Gly Arg Phe Gly Tyr Asn Asn Asn
                290                 295                 300

Val His Arg Pro Gly Thr Pro Pro His Lys Gly Gly Lys Gly Gly
305                 310                 315

<210> SEQ ID NO 11
<211> LENGTH: 1331
<212> TYPE: DNA
<213> ORGANISM: Brassica napus

<400> SEQUENCE: 11
ggcgaaaact tttttggtct gaagatcgag aaaagatttc gaaaatcaaa tttgggttcc    60
tgggcaatcg atttatgtcc gaaagattga agcttttgta agataaaaag atcgattggt   120
gttgttaagt ttcgatcgcg tgggggtctt tgtaatgacg cagcaagggc agggaagcat   180
ggaccctgcc gttctcgacg acatcattcg tcgtttgttg gattacagaa accctaagcc   240
tggaaccaaa caggtcatgc tcaacgagtc tgagatccga cagcttttgca gcgtgtctag   300 agagattttc cttcagcagc ctaacctcct tgagctcgag gctccaatta agatctgtgg   360
tgatattcat ggacagtact cagatctact gaggctattt gagtacggag gcttacctcc   420
tgcagctaac tatctattcc taggagatta cgtggatcgc gggaagcaga gcctagaaac   480
aatctgcctt ctccttgcct acaagatcaa atacctgag aacttcttcc tcctaagagg   540
caaccacgaa tgcgcttcca tcaaccgaat ctacggattc tacgatgaac gtaaacgcag   600
gttcagtgtc agactctgga aagtgtttac agattcttc aactgcctcc ctgtagctgc   660
tgtaatagac gataagatat tgtgtatgca cggtggcctt tctcctgatt tgaccagcgt   720
ggaacagatt aagaacatta gcgacctac cgatgttccg gactccggtt tgttatgtga   780
tctgcttggg tctgatccga gcaaagatgt gaaaggctgg gggatgaatg accgtggagt   840 ttcttcacacg tttgggcctg ataaagttgc tgagtttttg ataaagaatg atatggatct   900
catctgtcgt gctcaccagg ttgtagagga tggttatgag ttctttgcgg atagacagct   960

-continued

```
tgttactata ttttcagctc ctaattactg tggtgaattc gataatgctg gtgctatgat    1020
gagtgttgat gagagttaat gtgctctttt caaattctta agcctgcgga tcggaggcct    1080
cggttcttat gagttagagc ctcactggaa agaagacgaa attggcgaga tgaaaacggg    1140
agagagagag agagacattt gaaactcccg gagactttgt cctgaggcct ttgcaagaag    1200
gcaggaaaaa aaaacacagt gttacatgtt atatcatata atcttatttg aacttttgta    1260
atttcttttc tcaaaacttt tatgttatta aaaaaaaaaa aaaaaaaaaa aaaaaaaaaa    1320
aaaaaaaaaa a                                                         1331
```

<210> SEQ ID NO 12
<211> LENGTH: 294
<212> TYPE: PRT
<213> ORGANISM: Brassica napus

<400> SEQUENCE: 12

```
Met Thr Gln Gln Gly Gln Gly Ser Met Asp Pro Ala Val Leu Asp Asp
  1               5                  10                  15

Ile Ile Arg Arg Leu Leu Asp Tyr Arg Asn Pro Lys Pro Gly Thr Lys
                 20                  25                  30

Gln Val Met Leu Asn Glu Ser Glu Ile Arg Gln Leu Cys Ser Val Ser
             35                  40                  45

Arg Glu Ile Phe Leu Gln Gln Pro Asn Leu Leu Glu Leu Glu Ala Pro
         50                  55                  60

Ile Lys Ile Cys Gly Asp Ile His Gly Gln Tyr Ser Asp Leu Leu Arg
 65                  70                  75                  80

Leu Phe Glu Tyr Gly Gly Leu Pro Pro Ala Ala Asn Tyr Leu Phe Leu
                 85                  90                  95

Gly Asp Tyr Val Asp Arg Gly Lys Gln Ser Leu Glu Thr Ile Cys Leu
            100                 105                 110

Leu Leu Ala Tyr Lys Ile Lys Tyr Pro Glu Asn Phe Phe Leu Leu Arg
        115                 120                 125

Gly Asn His Glu Cys Ala Ser Ile Asn Arg Ile Tyr Gly Phe Tyr Asp
    130                 135                 140

Glu Arg Lys Arg Arg Phe Ser Val Arg Leu Trp Lys Val Phe Thr Asp
145                 150                 155                 160

Ser Phe Asn Cys Leu Pro Val Ala Ala Val Ile Asp Asp Lys Ile Leu
                165                 170                 175

Cys Met His Gly Gly Leu Ser Pro Asp Leu Thr Ser Val Glu Gln Ile
            180                 185                 190

Lys Asn Ile Lys Arg Pro Thr Asp Val Pro Asp Ser Gly Leu Leu Cys
        195                 200                 205

Asp Leu Leu Trp Ser Asp Pro Ser Lys Asp Val Lys Gly Trp Gly Met
    210                 215                 220

Asn Asp Arg Gly Val Ser Tyr Thr Phe Gly Pro Asp Lys Val Ala Glu
225                 230                 235                 240

Phe Leu Ile Lys Asn Asp Met Asp Leu Ile Cys Arg Ala His Gln Val
                245                 250                 255

Val Glu Asp Gly Tyr Glu Phe Phe Ala Asp Arg Gln Leu Val Thr Ile
            260                 265                 270

Phe Ser Ala Pro Asn Tyr Cys Gly Glu Phe Asp Asn Ala Gly Ala Met
        275                 280                 285

Met Ser Val Asp Glu Ser
    290
```

<210> SEQ ID NO 13
<211> LENGTH: 1184
<212> TYPE: DNA
<213> ORGANISM: Glycine max

<400> SEQUENCE: 13

```
cctaacccat cgttcgcacg gagccgtggt ggttctggct ctgtcctttt ttcctttctc      60
tcgttaccag aaccagaaga accatttgtg gccaacatgg atttggacca gtggatctcc     120
aaggtcaaag agggccagca tcttcttgaa gacgagcttc aacttctctg cgaatatgta     180
aaagagatcc ttatcgagga gtccaatgtg cagcctgtca atagtccagt gactgtttgt     240
ggtgatattc atggtcaatt ccatgatcta atgaaacttt tccagactgg gggtcatgtg     300
cctgagacaa attatatttt tatgggagac tttgttgatc gaggttacaa tagtcttgaa     360
gtttttacca tccttttact tctaaaagct agatacccag ctaatattac tcttttacgt     420
ggaaatcatg aaagtagaca attaacccag gtctatggat tttatgatga atgccagagg     480
aagtatggca atgccaatgc ttggcggtat tgtacagatg tgtttgacta tttaacactt     540
tctgcaatta ttgatggaac tgtgctttgt gttcatgggg cctttctcc tgacattcga      600
acaattgatc agataagggt cattgaccgg aactgtgaaa ttcctcatga gggtcctttc     660
tgtgatctaa tgtggagtga tcctgaagat attgaaacat gggcagtcag tccccgtgga     720
gcaggttggc tttttggatc cagggtcact tcggagttca atcacataaa taaccttgat     780
cttgtttgtc gagcgcacca actcgttcag gaaggcctta agtatatgtt ccaagataaa     840
ggccttgtaa ctgtatggtc tgcacctaat tactgttacc gatgtggaaa tgtagcttct     900
attctgagtt tcaatgaaaa atatggaaga gaagttaaat ttttcaccga acagaggag     960
aacaatcaga tgagagggcc caggacaggc gttccatatt tcttataagt tggtgcaaat    1020
tttgttttga atttattgta aaattagaca ctcatgtatt tatgctttgc cttttaaagg    1080
tggattttat tggtcacaag attaccaatc aaactatatc ttagctctgg gtcgcacaga    1140
taattttatg tttaaatttt tattgaaaaa aaaaaaaaa aaaa                      1184
```

<210> SEQ ID NO 14
<211> LENGTH: 303
<212> TYPE: PRT
<213> ORGANISM: Glycine max

<400> SEQUENCE: 14

```
Met Asp Leu Asp Gln Trp Ile Ser Lys Val Lys Glu Gly Gln His Leu
  1               5                  10                  15

Leu Glu Asp Glu Leu Gln Leu Leu Cys Glu Tyr Val Lys Glu Ile Leu
             20                  25                  30

Ile Glu Glu Ser Asn Val Gln Pro Val Asn Ser Pro Val Thr Val Cys
         35                  40                  45

Gly Asp Ile His Gly Gln Phe His Asp Leu Met Lys Leu Phe Gln Thr
     50                  55                  60

Gly Gly His Val Pro Glu Thr Asn Tyr Ile Phe Met Gly Asp Phe Val
 65                  70                  75                  80

Asp Arg Gly Tyr Asn Ser Leu Glu Val Phe Thr Ile Leu Leu Leu Leu
                 85                  90                  95

Lys Ala Arg Tyr Pro Ala Asn Ile Thr Leu Leu Arg Gly Asn His Glu
            100                 105                 110

Ser Arg Gln Leu Thr Gln Val Tyr Gly Phe Tyr Asp Glu Cys Gln Arg
```

```
                    115                 120                 125
Lys Tyr Gly Asn Ala Asn Ala Trp Arg Tyr Cys Thr Asp Val Phe Asp
            130                 135                 140

Tyr Leu Thr Leu Ser Ala Ile Ile Asp Gly Thr Val Leu Cys Val His
145                 150                 155                 160

Gly Gly Leu Ser Pro Asp Ile Arg Thr Ile Asp Gln Ile Arg Val Ile
                165                 170                 175

Asp Arg Asn Cys Glu Ile Pro His Glu Gly Pro Phe Cys Asp Leu Met
            180                 185                 190

Trp Ser Asp Pro Glu Asp Ile Glu Thr Trp Ala Val Ser Pro Arg Gly
            195                 200                 205

Ala Gly Trp Leu Phe Gly Ser Arg Val Thr Ser Glu Phe Asn His Ile
    210                 215                 220

Asn Asn Leu Asp Leu Val Cys Arg Ala His Gln Leu Val Gln Glu Gly
225                 230                 235                 240

Leu Lys Tyr Met Phe Gln Asp Lys Gly Leu Val Thr Val Trp Ser Ala
                245                 250                 255

Pro Asn Tyr Cys Tyr Arg Cys Gly Asn Val Ala Ser Ile Leu Ser Phe
            260                 265                 270

Asn Glu Asn Met Glu Arg Glu Val Lys Phe Phe Thr Glu Thr Glu Glu
        275                 280                 285

Asn Asn Gln Met Arg Gly Pro Arg Thr Gly Val Pro Tyr Phe Leu
    290                 295                 300
```

<210> SEQ ID NO 15
<211> LENGTH: 1417
<212> TYPE: DNA
<213> ORGANISM: Glycine max

<400> SEQUENCE: 15

```
aagaagaaga ggttttgatc ggatgcgatg agcacacagg ggcaagtgat tattgatgag      60
gcggttctgg atgacataat ccggcgctta acggaggtcc gactggcccg acccggcaag     120
caggttcagc tctccgagtc tgagatcaag caactctgcg tcgcttccag agacatcttc     180
attaaccagc ccaatttgct tgaactcgaa gcccccatca agatttgtgg tgacattcat     240
gggcagtaca gtgatttgtt aaggctattt gagtatgggg gttttgcctcc tactgcgaat    300
tatctctttt tgggggaata cgtggaccgt gggaagcaga gcttagaaac catatgtctt     360
ttgcttgcgt ataaaatcaa atatccagaa aacttttttcc tgttaagggg gaatcatgag   420
tgtgcttcca ttaataggat ttatgggttt tatgatgaat gtaagcgaag gtttaacgtg     480
aggctttgga agcctttac cgactgtttt aacttccttc ctgtggcagc ccttatagat     540
gataaaatat tgtgcatgca tggtggtctt tcccctgaac tcacaaactt ggatgaaatc     600
aggaatctac ctcgtcctac tgcgattccc gacaccggct tgctttgtga tttgctttgg     660
tctgatcctg gtagggatgt gaagggttgg ggtatgaatg acagaggagt gtcctacacc     720
tttggccctg ataaggtcgc tgagttcttg acaaagcatg acttggacct catttgtcgt     780
gctcatcagg ttgtagagga tgggtatgaa ttcttttgctg ataggcaact tgttacgata     840
ttttcagctc caaactattg tggtgaattt gacaatgctg gtgcgatgat gagtgtggac     900
gaaaacttga tgtgctcatt tcagattctt aagcctgcag agaaaaaatc aaagtttgtg    960
atgtcaaaca agatgtgatg gttggcacat cactgtcaag taattaacca agatgtattc   1020
gtggagctaa attaaatcct gaagatttag attgcatggt cttaagttct atctattctg   1080
```

-continued

```
aggtgatgat gatgaacaaa caagtttact gctataacat ccagtcaggc agtgagcatg    1140
aggtactaca agagatatta agcactgttg gatggccata aaagcaaagg cttttatctt    1200
tttttttctt ttcttgtttt ataattattc tgcaacacaa tatgtacata tatgtgttgt    1260
agatgctctg gaaatgacct tctttgctct gaaaggtcct cttagactat cgatttacac    1320
tgatagagca gtttgtgttg atgattgtgg ccaatttat ccagttagta aaggtgcaat     1380
tgatggattt tatggtttaa aaaaaaaaaa aaaaaaa                             1417
```

<210> SEQ ID NO 16
<211> LENGTH: 316
<212> TYPE: PRT
<213> ORGANISM: Glycine max

<400> SEQUENCE: 16

```
Met Ser Thr Gln Gly Gln Val Ile Ile Asp Glu Ala Val Leu Asp Asp
  1               5                  10                  15

Ile Ile Arg Arg Leu Thr Glu Val Arg Leu Ala Arg Pro Gly Lys Gln
             20                  25                  30

Val Gln Leu Ser Glu Ser Glu Ile Lys Gln Leu Cys Val Ala Ser Arg
         35                  40                  45

Asp Ile Phe Ile Asn Gln Pro Asn Leu Leu Glu Leu Glu Ala Pro Ile
     50                  55                  60

Lys Ile Cys Gly Asp Ile His Gly Gln Tyr Ser Asp Leu Leu Arg Leu
 65                  70                  75                  80

Phe Glu Tyr Gly Gly Leu Pro Pro Thr Ala Asn Tyr Leu Phe Leu Gly
                 85                  90                  95

Glu Tyr Val Asp Arg Gly Lys Gln Ser Leu Glu Thr Ile Cys Leu Leu
            100                 105                 110

Leu Ala Tyr Lys Ile Lys Tyr Pro Glu Asn Phe Phe Leu Leu Arg Gly
        115                 120                 125

Asn His Glu Cys Ala Ser Ile Asn Arg Ile Tyr Gly Phe Tyr Asp Glu
    130                 135                 140

Cys Lys Arg Arg Phe Asn Val Arg Leu Trp Lys Ala Phe Thr Asp Cys
145                 150                 155                 160

Phe Asn Phe Leu Pro Val Ala Ala Leu Ile Asp Asp Lys Ile Leu Cys
                165                 170                 175

Met His Gly Gly Leu Ser Pro Glu Leu Thr Asn Leu Asp Glu Ile Arg
            180                 185                 190

Asn Leu Pro Arg Pro Thr Ala Ile Pro Asp Thr Gly Leu Leu Cys Asp
        195                 200                 205

Leu Leu Trp Ser Asp Pro Gly Arg Asp Val Lys Gly Trp Gly Met Asn
    210                 215                 220

Asp Arg Gly Val Ser Tyr Thr Phe Gly Pro Asp Lys Val Ala Glu Phe
225                 230                 235                 240

Leu Thr Lys His Asp Leu Asp Leu Ile Cys Arg Ala His Gln Val Val
                245                 250                 255

Glu Asp Gly Tyr Glu Phe Phe Ala Asp Arg Gln Leu Val Thr Ile Phe
            260                 265                 270

Ser Ala Pro Asn Tyr Cys Gly Glu Phe Asp Asn Ala Gly Ala Met Met
        275                 280                 285

Ser Val Asp Glu Asn Leu Met Cys Ser Phe Gln Ile Leu Lys Pro Ala
    290                 295                 300

Glu Lys Lys Ser Lys Phe Val Met Ser Asn Lys Met
305                 310                 315
```

<210> SEQ ID NO 17
<211> LENGTH: 1587
<212> TYPE: DNA
<213> ORGANISM: Glycine max

<400> SEQUENCE: 17

```
tctttccctc cacaagaaaa aaaaatcaga aaaaggaaat gagagattgt tggacaccgt      60
gcaaatcaag cactttgctt gttatttcac gcgccctctc tccattttga cctcccttc     120
ctcttcgttc cccactcact gcaacggcgc cggagatccg tcgctctcct cctcctcctc    180
ctcctcctcc tcctcctccg ccgcgatggg cgccaattcc atgctctccg agtcctctca    240
cgatctcgac gaccagatct cccagctcat gcagtgcaag ccactctccg agcaacaggt    300
cagaggttta tgtgagaagg ctaaggagat tttaatggat gaaagtaatg ttcagcctgt    360
taaaagccct gtgacaattt gtggcgatat tcatgggcaa tttcatgatc ttgctgaact    420
gtttcgaatt ggagggaagt gtccagatac taactacttg tttatgggtg attatgtgga    480
ccggggttat tattcagttg agactgtatc gctccttgtg gcactgaaag ttcggtatcc    540
ccagcgaatt actattctta gaggaaaacca tgaaagccgt cagattactc aagtatatgg    600
attttatgat gaatgcctta gaaagtatgg taatgctaat gtttggaaga cctttacaga    660
cctttttgat tttttttccat tgactgcatt ggttgaatct gaaatattct gtttgcatgg    720
tggactgtca ccttcaattg agacccttga taacataagg aactttgatc gtgttcaaga    780
ggttcctcat gaaggcccca tgtgtgatct attgtggtct gacccagatg acagatgtgg    840
ctggggaatt tctcctcgtg gtgctggata cttttggc caggatatat ctgaacaatt    900
caatcacact aacagcctta aattgattgc tagagctcat cagcttgtta tggatggatt    960
taactgggct catgaacaaa aggtggttac cattttagt gcacctaact actgttaccg   1020
atgtgggaac atggcttcca tattggaggt tgatgattgc aagggtcaca cattcatcca   1080
gtttgaacct gctcctagga gaggagaacc tgatgtcact cgtagaacgc tgattacttt   1140
cttataatgt agctgttgaa tgtcatactg ttatatcatg ttacctcta ctgcactaat   1200
ttcaggtagt tgcgcatcct catatcacga gattgctgta acatttaaa tccatggata   1260
tacacgttcc gtgctttgg gggttgtcca aagactgctt tgatgtataa taggcaggta   1320
acattccact gattacactc gaggaattgc tggacaccttt gtctggagaa gtcgccaaga   1380
tgatgtcata atacgtattg ttccagcaaa atgtggatat ttttttgtttg ttttttcgtg   1440
tttatttttt gtatcttatg ttcagtaact ccctttatg gctttacaag ctatatgact   1500
ggattttgtt ggtcgtggat gtttttgtcg tgttctatca ttttcagtt aaagttgcat   1560
gatatagtga aaaaaaaaa aaaaaaa                                        1587
```

<210> SEQ ID NO 18
<211> LENGTH: 313
<212> TYPE: PRT
<213> ORGANISM: Glycine max

<400> SEQUENCE: 18

Met Gly Ala Asn Ser Met Leu Ser Glu Ser Ser His Asp Leu Asp Asp
 1               5                  10                  15

Gln Ile Ser Gln Leu Met Gln Cys Lys Pro Leu Ser Glu Gln Gln Val
            20                  25                  30

Arg Gly Leu Cys Glu Lys Ala Lys Glu Ile Leu Met Asp Glu Ser Asn
        35                  40                  45

```
Val Gln Pro Val Lys Ser Pro Val Thr Ile Cys Gly Asp Ile His Gly
         50                  55                  60

Gln Phe His Asp Leu Ala Glu Leu Phe Arg Ile Gly Gly Lys Cys Pro
 65                  70                  75                  80

Asp Thr Asn Tyr Leu Phe Met Gly Asp Tyr Val Asp Arg Gly Tyr Tyr
                 85                  90                  95

Ser Val Glu Thr Val Ser Leu Leu Val Ala Leu Lys Val Arg Tyr Pro
            100                 105                 110

Gln Arg Ile Thr Ile Leu Arg Gly Asn His Glu Ser Arg Gln Ile Thr
        115                 120                 125

Gln Val Tyr Gly Phe Tyr Asp Glu Cys Leu Arg Lys Tyr Gly Asn Ala
    130                 135                 140

Asn Val Trp Lys Thr Phe Thr Asp Leu Phe Asp Phe Phe Pro Leu Thr
145                 150                 155                 160

Ala Leu Val Glu Ser Glu Ile Phe Cys Leu His Gly Gly Leu Ser Pro
                165                 170                 175

Ser Ile Glu Thr Leu Asp Asn Ile Arg Asn Phe Asp Arg Val Gln Glu
            180                 185                 190

Val Pro His Glu Gly Pro Met Cys Asp Leu Leu Trp Ser Asp Pro Asp
        195                 200                 205

Asp Arg Cys Gly Trp Gly Ile Ser Pro Arg Gly Ala Gly Tyr Thr Phe
    210                 215                 220

Gly Gln Asp Ile Ser Glu Gln Phe Asn His Thr Asn Ser Leu Lys Leu
225                 230                 235                 240

Ile Ala Arg Ala His Gln Leu Val Met Asp Gly Phe Asn Trp Ala His
                245                 250                 255

Glu Gln Lys Val Val Thr Ile Phe Ser Ala Pro Asn Tyr Cys Tyr Arg
            260                 265                 270

Cys Gly Asn Met Ala Ser Ile Leu Glu Val Asp Asp Cys Lys Gly His
        275                 280                 285

Thr Phe Ile Gln Phe Glu Pro Ala Pro Arg Arg Gly Glu Pro Asp Val
    290                 295                 300

Thr Arg Arg Thr Pro Asp Tyr Phe Leu
305                 310

<210> SEQ ID NO 19
<211> LENGTH: 1480
<212> TYPE: DNA
<213> ORGANISM: Glycine max

<400> SEQUENCE: 19
gctcactctt ccaactacta ctgttgttct tcttcgtcgt cttggccttc gcatcttcac      60
aatcacatcc aatagagaca cgttgacttt gctggaagaa gaagaagaag agaatggaac     120
aatcgctttt ggatgacata atcaatcgcc tcctcgaagt tcctacccta ccggctaagc     180
aggttcagct atccgagtcc gagatccgtc aactctgcgt agtttccaga gaaatttctc     240
tgcaacaacc taatttattg gagctcgaag cacctattaa gatttgtggt gatgtacatg     300
ggcaatattc tgatctttta aggctttttg agtacggtgg attacctcct gaagccaact     360
atttgttttt gggggattat gttgatcgag ggaagcagag tttagaaaca atttgcctcc     420
tccttgctta taaataaaaa tatcctgaga acttttttctt gttaagggga aaccatgaat     480
gtgcttctat aaaccggata tatggatttt atgatgagtg caagagaagg ttcaatgtaa     540
ggttatggaa gacatttaca gactgcttca attgcctgcc tgtggcagcc cttgtcgatg     600
```

```
aaaagattttt gtgtatgcat gggggacttt ctcccgactt aaataatttg gaccaaatta      660
gaaatttaca gcggcccaca gatgttcctg atacaggttt gctttgtgat ctgctttggt      720
ctgacccgag caaagatgtt caaggatggg aatgaatga cagaggagtt tcatacacat      780
ttggtgctga taaggtctca caatttcttc agaaacatga tcttgatctt gtttgtcgtg      840
ctcatcaggt tgtggaagat ggatacgagt tctttgctaa tcgacaactt gtaacaatat      900
tttcagcacc taattattgt ggggagtttg acaatgctgg tgctatgatg agtgttgatg      960
agacgctaat gtgctctttc caaatattaa agccagctga taaaaaagca aagctcaatt     1020
ttggaagtac aaccactgct aagcctggaa actctccagc aggtgtaaag gttggaagat     1080
attagtcctt cctggatgcg aaagtgtgaa attaaatttg gctaaaagat tgctactact     1140
acggatcagc ttgggcttga actcctaatg gttgcaagaa ggggaaaatc aagttccatt     1200
tcgcctacta tgatattttg gaattgtaaa atcaaagaga acaccattat gaagtttgta     1260
aaccattgtt tattattggt acaaatttgc atttcaagat ggagagccat aatctccttg     1320
tcttccttgt acactaataa ctggtatatt ttcttaactg taagcttcac aagcgtagat     1380
ggatacatcc gaatctgttg ctgagaacca tttaaaaatg cttatacgat ttggcatata     1440
tggatggcag ttgaggctgg tgaaaaaaaa aaaaaaaaa                             1480
```

<210> SEQ ID NO 20
<211> LENGTH: 323
<212> TYPE: PRT
<213> ORGANISM: Glycine max

<400> SEQUENCE: 20

```
Met Glu Gln Ser Leu Leu Asp Asp Ile Ile Asn Arg Leu Leu Glu Val
  1               5                  10                  15

Pro Thr Leu Pro Ala Lys Gln Val Gln Leu Ser Glu Ser Glu Ile Arg
                 20                  25                  30

Gln Leu Cys Val Val Ser Arg Glu Ile Phe Leu Gln Gln Pro Asn Leu
             35                  40                  45

Leu Glu Leu Glu Ala Pro Ile Lys Ile Cys Gly Asp Val His Gly Gln
 50                  55                  60

Tyr Ser Asp Leu Leu Arg Leu Phe Glu Tyr Gly Gly Leu Pro Pro Glu
 65                  70                  75                  80

Ala Asn Tyr Leu Phe Leu Gly Asp Tyr Val Asp Arg Gly Lys Gln Ser
                 85                  90                  95

Leu Glu Thr Ile Cys Leu Leu Ala Tyr Lys Ile Lys Tyr Pro Glu
            100                 105                 110

Asn Phe Phe Leu Leu Arg Gly Asn His Glu Cys Ala Ser Ile Asn Arg
            115                 120                 125

Ile Tyr Gly Phe Tyr Asp Glu Cys Lys Arg Arg Phe Asn Val Arg Leu
            130                 135                 140

Trp Lys Thr Phe Thr Asp Cys Phe Asn Cys Leu Pro Val Ala Ala Leu
145                 150                 155                 160

Val Asp Glu Lys Ile Leu Cys Met His Gly Gly Leu Ser Pro Asp Leu
                165                 170                 175

Asn Asn Leu Asp Gln Ile Arg Asn Leu Gln Arg Pro Thr Asp Val Pro
            180                 185                 190

Asp Thr Gly Leu Leu Cys Asp Leu Leu Trp Ser Asp Pro Ser Lys Asp
            195                 200                 205

Val Gln Gly Trp Gly Met Asn Asp Arg Gly Val Ser Tyr Thr Phe Gly
```

```
                210             215                 220
Ala Asp Lys Val Ser Gln Phe Leu Gln Lys His Asp Leu Asp Leu Val
225                 230                 235                 240

Cys Arg Ala His Gln Val Val Glu Asp Gly Tyr Glu Phe Phe Ala Asn
                245                 250                 255

Arg Gln Leu Val Thr Ile Phe Ser Ala Pro Asn Tyr Cys Gly Glu Phe
            260                 265                 270

Asp Asn Ala Gly Ala Met Met Ser Val Asp Glu Thr Leu Met Cys Ser
            275                 280                 285

Phe Gln Ile Leu Lys Pro Ala Asp Lys Lys Ala Lys Leu Asn Phe Gly
        290                 295                 300

Ser Thr Thr Thr Ala Lys Pro Gly Asn Ser Pro Ala Gly Val Lys Val
305                 310                 315                 320

Gly Arg Tyr

<210> SEQ ID NO 21
<211> LENGTH: 1386
<212> TYPE: DNA
<213> ORGANISM: Glycine max

<400> SEQUENCE: 21
accgtcccgg tcgcgccaac cgccgcaacc cgaagaaacc gaatcgatct gagagaaggt      60
gcgatctcgg aggtgggagc caaacgaaac gatgccgtct cacgcggatc tggagcgaca     120
gatcgagcag ctgatggact gcaagcctct gtcggagtcg gaggtgaagg cgctgtgcga     180
tcaagcgagg acgattcttg tggaggagtg gaacgtgcaa ccggttaagt gccccgtcac     240
cgtctgcggc gatattcacg gccagttcta cgatctcatc gagctgtttc ggattggagg     300
gaacgctccc gataccaatt atctcttcat gggtgattat gtagatcgtg gatactattc     360
agtggagact gttacacttt tggtggcttt gaaagtccgt tatagagata aatcacaat     420
tctcagggga aatcatgaaa gccgtcaaat tactcaagtg tatggcttct atgatgaatg     480
cttgagaaaa tatggaaatg cgaatgtctg gaaatacttt acagacttgt ttgattattt     540
gcctctgact gccctcattg agagtcagat tttctgcttg catggaggtc tctcaccttc     600
tttggataca ctggataaca tcagagcatt ggatcgtatt caagaggttc acatgaagg     660
accaatgtgt gatctcttgt ggtctgaccc tgatgatcgc tgtggatggg aatatctcc     720
acgtggtgca ggatacacat ttgggcagga tatagctgct cagtttaatc ataccaatgg     780
cctctccctg atatcgagag cacatcagct tgttatggaa ggattcaatt ggtgccagga     840
caagaatgtg gtgactgtat ttagtgctcc aaattactgt tatcgatgtg gaatatggc     900
tgccatacta gaaataggag agaatatgga tcagaatttt cttcagtttg atccagctcc     960
caggcaaatt gagcctgaca ccacacgcaa gactccagat tattttttgt aacttcattt    1020
atctgcctgt ttgtagttac tgcttctgc cattactgta gatgtgtctt taaggaaagg    1080
agttttactg tgtaagtgga gggtggtcat caacataatt ctttctttg gagtttacct    1140
gttgctgctg ccgctgcctt atctgtacaa gaaaccaata gaactgacac atgacaccaa    1200
ttggggttgt tgtatatttt tgggaggaag cagcataaca tggtatatct tttctgtaat    1260
ccttttctt tcctttaaat taaatctcaa gttaaagagc agatttttga gtcctgacaa    1320
tgatgtcctt ttgagacttt tgatgatgcc aaatgaaatt gcaggttttc aaaaaaaaa    1380
aaaaaa                                                              1386
```

<210> SEQ ID NO 22
<211> LENGTH: 306
<212> TYPE: PRT
<213> ORGANISM: Glycine max

<400> SEQUENCE: 22

Met Pro Ser His Ala Asp Leu Glu Arg Gln Ile Glu Gln Leu Met Asp
 1               5                  10                  15

Cys Lys Pro Leu Ser Glu Ser Glu Val Lys Ala Leu Cys Asp Gln Ala
             20                  25                  30

Arg Thr Ile Leu Val Glu Glu Trp Asn Val Gln Pro Val Lys Cys Pro
         35                  40                  45

Val Thr Val Cys Gly Asp Ile His Gly Gln Phe Tyr Asp Leu Ile Glu
     50                  55                  60

Leu Phe Arg Ile Gly Gly Asn Ala Pro Asp Thr Asn Tyr Leu Phe Met
 65                  70                  75                  80

Gly Asp Tyr Val Asp Arg Gly Tyr Tyr Ser Val Glu Thr Val Thr Leu
                 85                  90                  95

Leu Val Ala Leu Lys Val Arg Tyr Arg Asp Arg Ile Thr Ile Leu Arg
            100                 105                 110

Gly Asn His Glu Ser Arg Gln Ile Thr Gln Val Tyr Gly Phe Tyr Asp
        115                 120                 125

Glu Cys Leu Arg Lys Tyr Gly Asn Ala Asn Val Trp Lys Tyr Phe Thr
    130                 135                 140

Asp Leu Phe Asp Tyr Leu Pro Leu Thr Ala Leu Ile Glu Ser Gln Ile
145                 150                 155                 160

Phe Cys Leu His Gly Gly Leu Ser Pro Ser Leu Asp Thr Leu Asp Asn
                165                 170                 175

Ile Arg Ala Leu Asp Arg Ile Gln Glu Val Pro His Glu Gly Pro Met
            180                 185                 190

Cys Asp Leu Leu Trp Ser Asp Pro Asp Asp Arg Cys Gly Trp Gly Ile
        195                 200                 205

Ser Pro Arg Gly Ala Gly Tyr Thr Phe Gly Gln Asp Ile Ala Ala Gln
    210                 215                 220

Phe Asn His Thr Asn Gly Leu Ser Leu Ile Ser Arg Ala His Gln Leu
225                 230                 235                 240

Val Met Glu Gly Phe Asn Trp Cys Gln Asp Lys Asn Val Val Thr Val
                245                 250                 255

Phe Ser Ala Pro Asn Tyr Cys Tyr Arg Cys Gly Asn Met Ala Ala Ile
            260                 265                 270

Leu Glu Ile Gly Glu Asn Met Asp Gln Asn Phe Leu Gln Phe Asp Pro
        275                 280                 285

Ala Pro Arg Gln Ile Glu Pro Asp Thr Thr Arg Lys Thr Pro Asp Tyr
    290                 295                 300

Phe Leu
305

<210> SEQ ID NO 23
<211> LENGTH: 1487
<212> TYPE: DNA
<213> ORGANISM: Oryza sativa

<400> SEQUENCE: 23
gcgcccccca accgcatctc aatctctctc ctctctctct ctctccagct cgcctccccc      60
tcgccggcga cgagctctcc cccggctagg gttagaccag gtgcccctct tgtctgcggc     120

-continued

```
ggaggaggtg ggaggaagga tggaggagtc cgtgggctcg cgcggcggcg gcggcggcgg      180
cctggacgcc cagatcgagc agctcatgga gtgccgcccg ctctccgagc ccgaggtcaa      240
gacgttgtgc gagaaggcga aggagatatt gatggaagaa agcaacgttc agccagttaa      300
gagcccagtc acaatttgtg gtgatatcca tgggcaattc catgatctag tagagctctt      360
tcggattggt gggaagtgtc cagatacaaa ttatttgttt atgggagatt atgtagatcg      420
tggctactat tctgttgaga ctgttacact tttggttgca ctgaaggtgc gctacccaca      480
gcggattaca atccttcgtg gaaaccatga gagtcggcag atcacacagg tgtatggatt      540
ctacgacgaa tgcctacgaa agtatggaag tgcaaatgtc tggaagatct tcaccgatct      600
ttttgactat tttccattga cagcattggt tgaatcagag attttctgcc tccatggtgg      660
tttatcgcca tcaatcgaca atcttgatag tgttcgcagc ttagatcgtg ttcaagaggt      720
ccctcatgag ggaccaatgt gtgatcttct atggtctgac ccggatgatc gatgcggttg      780
gggcatatct cctcgtggtg ctggctacac ttttggccag gacatatcgg agcagtttaa      840
ccataccaat aatctcaaac ttgtagcccg ggctcatcaa ttagttatgg aaggatataa      900
ctgggcgcac gaacaaaagg tcgtgaccat attcagtgca cctaattatt gttatcgctg      960
tggcaacatg gcatccatcc tggaggttga tgactgcagg aatcacacat ttattcagtt     1020
tgaaccagct cctaggagag gtgaaccaga tgtgacacgg agaacacctg attatttcct     1080
ttaaattatc tgttgtaatt tgtattgttt tgtttctttt gtttctctaa gaccgcaata     1140
gtgagtgctg gtcagtaaaa tttttgttgga tccctttggt aactaaactg ccagcgata     1200 gcatgagaat gccgatgccc aaaaaaaatg tgaaacttat gcccctcatt gatcattgtg     1260
agaatggtgc tgtcatccag gatgcaacgc attgcatacg attcagtctc ttacccaccc     1320
ttcccaagcc atgtttaggt ggcattgtgt tgacagatat caaaattcca ttttggtata     1380
agctgcttga gttatgtatt ggctggtttt gtaactgatg tgcttggacc ttctatcatt     1440
aatgacagac aagctgatct ctcggttgcg aaaaaaaaaa aaaaaaa                   1487
```

<210> SEQ ID NO 24
<211> LENGTH: 314
<212> TYPE: PRT
<213> ORGANISM: Oryza sativa

<400> SEQUENCE: 24

```
Met Glu Glu Ser Val Gly Ser Arg Gly Gly Gly Gly Gly Gly Leu Asp
  1               5                  10                  15

Ala Gln Ile Glu Gln Leu Met Glu Cys Arg Pro Leu Ser Glu Pro Glu
             20                  25                  30

Val Lys Thr Leu Cys Glu Lys Ala Lys Glu Ile Leu Met Glu Glu Ser
         35                  40                  45

Asn Val Gln Pro Val Lys Ser Pro Val Thr Ile Cys Gly Asp Ile His
     50                  55                  60

Gly Gln Phe His Asp Leu Val Glu Leu Phe Arg Ile Gly Gly Lys Cys
 65                  70                  75                  80

Pro Asp Thr Asn Tyr Leu Phe Met Gly Asp Tyr Val Asp Arg Gly Tyr
                 85                  90                  95

Tyr Ser Val Glu Thr Val Thr Leu Leu Val Ala Leu Lys Val Arg Tyr
            100                 105                 110

Pro Gln Arg Ile Thr Ile Leu Arg Gly Asn His Glu Ser Arg Gln Ile
        115                 120                 125

Thr Gln Val Tyr Gly Phe Tyr Asp Glu Cys Leu Arg Lys Tyr Gly Ser
```

```
                130                 135                 140
Ala Asn Val Trp Lys Ile Phe Thr Asp Leu Phe Asp Tyr Phe Pro Leu
145                 150                 155                 160

Thr Ala Leu Val Glu Ser Glu Ile Phe Cys Leu His Gly Gly Leu Ser
                165                 170                 175

Pro Ser Ile Asp Asn Leu Asp Ser Val Arg Ser Leu Asp Arg Val Gln
                180                 185                 190

Glu Val Pro His Glu Gly Pro Met Cys Asp Leu Leu Trp Ser Asp Pro
                195                 200                 205

Asp Asp Arg Cys Gly Trp Gly Ile Ser Pro Arg Gly Ala Gly Tyr Thr
210                 215                 220

Phe Gly Gln Asp Ile Ser Glu Gln Phe Asn His Thr Asn Asn Leu Lys
225                 230                 235                 240

Leu Val Ala Arg Ala His Gln Leu Val Met Glu Gly Tyr Asn Trp Ala
                245                 250                 255

His Glu Gln Lys Val Val Thr Ile Phe Ser Ala Pro Asn Tyr Cys Tyr
                260                 265                 270

Arg Cys Gly Asn Met Ala Ser Ile Leu Glu Val Asp Asp Cys Arg Asn
                275                 280                 285

His Thr Phe Ile Gln Phe Glu Pro Ala Pro Arg Arg Gly Glu Pro Asp
                290                 295                 300

Val Thr Arg Arg Thr Pro Asp Tyr Phe Leu
305                 310

<210> SEQ ID NO 25
<211> LENGTH: 1298
<212> TYPE: DNA
<213> ORGANISM: Oryza sativa

<400> SEQUENCE: 25
gaggcttgag ctccacctcc acctcctcca cctccaaccc ccgatccccc gcaaacccta      60
gccctctccc ccaccctcct cgccggcggc gagcggcggc ggcgcgcggc gggacccgga     120
gcccccagta gcgcctcctc cgtcctcccc tccctgaggt gcggggagaa ggatgccgtc     180
gtcgcacggg gatctggacc ggcagatcgc gcagctgcgg gagtgcaagc acctggcgga     240
gggggaggtg agggcgctgt gcgagcaggc gaaggccatc ctcatggagg agtgaaacgt     300
gcagccggtg cggtgccccg tcacggtctg cggcgacatc cacggccagt tctacgacct     360
catcgagctc ttccgcatcg gcggcgaggc gcccgacacc aactacctct tcatgggcga     420
ctacgtcgac cgtggctact actcagtgga gactgtttcg ttgttggtgg ctttgaaagt     480
acgctacaga gatcgaatta caatattgag aggaaatcat gagagcagac aaatcactca     540
agtgtacggc ttctacgatg aatgcttgag aaagtatgga aatgcaaatg tatggaaata     600
ctttacagac ttgtttgatt atttgcctct cacagctctt atagaaaacc aggtgttctg     660
ccttcacggt ggtctctctc catcattgga tactttagat aacatccgtg ctcttgatcg     720
tatacaagag gttcctcatg aaggacccat gtgtgatctt tgtggtctg acccagatga     780 cagatgcggg tggggaattt caccgagagg agcaggttat acatttgggc aagatatcgc     840
tcaacagttt aaccatacaa atggtctatc tctcatctca aggcacatc aacttgtaat     900 ggaaggattt aattggtgtc aggacaagaa tgttgtgacg gtcttcagtg caccaaacta     960
ctgttatcgc tgtggtaaca tggctgcaat tcttgagatt ggcgaaaaca tggatcagaa    1020
cttcctccaa tttgatccag ctcctcggca aattgaacca gacacaacac gcaagactcc    1080
```

-continued

```
cgactactttt tgtaatttg tggtgttgac aattttaact cacctgtgtt gatgctcctc    1140
tcctccgcgg tgtcggggtc tgtagatctt ctgtccttag atacgggttc cacgagcccg    1200
gctgtatgtc tctcaattct tttgtttgga gattttgttg ctgcttctca acctttatac    1260
aagacgttaa aagttacatg cactggattt ttttctcc                            1298
```

<210> SEQ ID NO 26
<211> LENGTH: 307
<212> TYPE: PRT
<213> ORGANISM: Oryza sativa

<400> SEQUENCE: 26

```
Met Pro Ser Ser His Gly Asp Leu Asp Arg Gln Ile Ala Gln Leu Arg
  1               5                  10                  15

Glu Cys Lys His Leu Ala Glu Gly Val Arg Ala Leu Cys Glu Gln
                 20                  25                  30

Ala Lys Ala Ile Leu Met Glu Glu Trp Asn Val Gln Pro Val Arg Cys
             35                  40                  45

Pro Val Thr Val Cys Gly Asp Ile His Gly Gln Phe Tyr Asp Leu Ile
         50                  55                  60

Glu Leu Phe Arg Ile Gly Gly Glu Ala Pro Asp Thr Asn Tyr Leu Phe
 65                  70                  75                  80

Met Gly Asp Tyr Val Asp Arg Gly Tyr Tyr Ser Val Glu Thr Val Ser
                 85                  90                  95

Leu Leu Val Ala Leu Lys Val Arg Tyr Arg Asp Arg Ile Thr Ile Leu
                100                 105                 110

Arg Gly Asn His Glu Ser Arg Gln Ile Thr Gln Val Tyr Gly Phe Tyr
            115                 120                 125

Asp Glu Cys Leu Arg Lys Tyr Gly Asn Ala Asn Val Trp Lys Tyr Phe
        130                 135                 140

Thr Asp Leu Phe Asp Tyr Leu Pro Leu Thr Ala Leu Ile Glu Asn Gln
145                 150                 155                 160

Val Phe Cys Leu His Gly Gly Leu Ser Pro Ser Leu Asp Thr Leu Asp
                165                 170                 175

Asn Ile Arg Ala Leu Asp Arg Ile Gln Glu Val Pro His Glu Gly Pro
            180                 185                 190

Met Cys Asp Leu Leu Trp Ser Asp Pro Asp Asp Arg Cys Gly Trp Gly
        195                 200                 205

Ile Ser Pro Arg Gly Ala Gly Tyr Thr Phe Gly Gln Asp Ile Ala Gln
    210                 215                 220

Gln Phe Asn His Thr Asn Gly Leu Ser Leu Ile Ser Arg Ala His Gln
225                 230                 235                 240

Leu Val Met Glu Gly Phe Asn Trp Cys Gln Asp Lys Asn Val Val Thr
                245                 250                 255

Val Phe Ser Ala Pro Asn Tyr Cys Tyr Arg Cys Gly Asn Met Ala Ala
            260                 265                 270

Ile Leu Glu Ile Gly Glu Asn Met Asp Gln Asn Phe Leu Gln Phe Asp
        275                 280                 285

Pro Ala Pro Arg Gln Ile Glu Pro Asp Thr Thr Arg Lys Thr Pro Asp
    290                 295                 300

Tyr Phe Leu
305
```

<210> SEQ ID NO 27
<211> LENGTH: 1497

<212> TYPE: DNA
<213> ORGANISM: Oryza sativa

<400> SEQUENCE: 27

```
ccaatgccaa gaacaagaaa tcagagagcc caagcaaaaa atccaatccg aatcccctcc      60
aaaaacccac caaacaatct cctccatctc caagaacaag aacaagagag catcctagaa     120
cattagggga taaggagga ggagaagaag accaagaaaa gtttcgagag gagagggagg     180
agagttcaag aacttggaga aaggggatg gatccggtgt tgctggacga catcatccgg     240
aggcttatcg aggtgaagaa tctgaagccg gggaagaacg cgcagctttc ggagtcggag     300
attaagcagc tctgcgcaac ctccaaggag atcttcctga atcagcccaa cctgctcgag     360
ctcgaggccc ccatcaaaat ctgcggtgat gttcatggac agtattctga tctcctgagg     420
ctgtttgatt atggtgggta tccacctcag tccaactatc tcttcttggg cgattatgtg     480
gaccggggaa agcaaagcct tgagacgata tgccttcttt tggcttataa gatcaagtac     540
cctgaaaact tcttcctact cagaggcaac catgaatgtg catcggtcaa ccgcatctat     600
ggattttatg acgagtgcaa gcgcagattc agtgtaaaac tctggaagac tttactgac     660
tgttttaact gcttaccagt ggcagcattg atagatgaaa agattctttg tatgcacgga     720
ggtctttctc cagagttgaa taagctggat caaatactca acctcaaccg ccccacggat     780
gtgcctgata ctgggttact ttgtgatctc ctttggtccg atccatccaa tgacgcacaa     840
gggtgggcta tgaatgatcg aggtgtctca tatacattcg ggccagacaa agtgtctgaa     900
tttcttgaga agcatgattt agacctcatc tgtcgagccc atcaggttgt cgaagatggg     960
tacgagttct tgctaaccg ccaacttgta acaatattct cggcccctaa ttactgtgga    1020
gaattttgata atgctggtgc catgatgagt gtagatgata cactgatgtg ctcttttcaa    1080
atactaaaac cagcgaggaa aatgttgggt ggttccacga attccaaatc cggcttcaag    1140
tcactgagag gtggtgacg atgagcaaag ctgtgatctg atctgctggc gcatgtcttc    1200
tacagcggct gcgactaacc ggcatttttcg cctacagctc gggtccataa acagcgaagc    1260
agatagaaat gtgtacaact ttccagccga tggaactgta catcatcgtt catgttggat    1320
taacacttgt tgtaatgtat tattggtttt accatgcgga tctcttatca tatgagagga    1380
tgtgaatgaa aactgttctc ccgtcctccc ccctaaattc agaaaagttc agacagaagg    1440
actccaataa aaatagctag aatcgaatgc ttttgaacca aaaaaaaaaa aaaaaaa       1497
```

<210> SEQ ID NO 28
<211> LENGTH: 316
<212> TYPE: PRT
<213> ORGANISM: Oryza sativa

<400> SEQUENCE: 28

```
Met Asp Pro Val Leu Leu Asp Asp Ile Ile Arg Arg Leu Ile Glu Val
  1               5                  10                  15

Lys Asn Leu Lys Pro Gly Lys Asn Ala Gln Leu Ser Glu Ser Glu Ile
                 20                  25                  30

Lys Gln Leu Cys Ala Thr Ser Lys Glu Ile Phe Leu Asn Gln Pro Asn
             35                  40                  45

Leu Leu Glu Leu Glu Ala Pro Ile Lys Ile Cys Gly Asp Val His Gly
         50                  55                  60

Gln Tyr Ser Asp Leu Leu Arg Leu Phe Asp Tyr Gly Gly Tyr Pro Pro
 65                  70                  75                  80

Gln Ser Asn Tyr Leu Phe Leu Gly Asp Tyr Val Asp Arg Gly Lys Gln
```

```
                 85                  90                  95
Ser Leu Glu Thr Ile Cys Leu Leu Ala Tyr Lys Ile Lys Tyr Pro
            100                 105                 110

Glu Asn Phe Phe Leu Leu Arg Gly Asn His Glu Cys Ala Ser Val Asn
            115                 120                 125

Arg Ile Tyr Gly Phe Tyr Asp Glu Cys Lys Arg Phe Ser Val Lys
            130                 135                 140

Leu Trp Lys Thr Phe Thr Asp Cys Phe Asn Cys Leu Pro Val Ala Ala
145                 150                 155                 160

Leu Ile Asp Glu Lys Ile Leu Cys Met His Gly Gly Leu Ser Pro Glu
                165                 170                 175

Leu Asn Lys Leu Asp Gln Ile Leu Asn Leu Asn Arg Pro Thr Asp Val
            180                 185                 190

Pro Asp Thr Gly Leu Leu Cys Asp Leu Leu Trp Ser Asp Pro Ser Asn
            195                 200                 205

Asp Ala Gln Gly Trp Ala Met Asn Asp Arg Gly Val Ser Tyr Thr Phe
            210                 215                 220

Gly Pro Asp Lys Val Ser Glu Phe Leu Glu Lys His Asp Leu Asp Leu
225                 230                 235                 240

Ile Cys Arg Ala His Gln Val Val Glu Asp Gly Tyr Glu Phe Phe Ala
                245                 250                 255

Asn Arg Gln Leu Val Thr Ile Phe Ser Ala Pro Asn Tyr Cys Gly Glu
            260                 265                 270

Phe Asp Asn Ala Gly Ala Met Met Ser Val Asp Asp Thr Leu Met Cys
            275                 280                 285

Ser Phe Gln Ile Leu Lys Pro Ala Arg Lys Met Leu Gly Gly Ser Thr
290                 295                 300

Asn Ser Lys Ser Gly Phe Lys Ser Leu Arg Gly Trp
305                 310                 315

<210> SEQ ID NO 29
<211> LENGTH: 1354
<212> TYPE: DNA
<213> ORGANISM: Oryza sativa

<400> SEQUENCE: 29
gccgcgccga gatctagggt tgggcgcgcg cgacgccccc ccccgcggc gaggaggatg    60 agcagccccc atggcggcct cgacgaccag atcgagcgcc tcatgcagtg caagcccctc   120
cccgagcccg aggtcagagc actttgcgag aaggcaaaag agatattgat ggaggagagc   180
aacgttcaac ctgtaaagag tcctgttaca atatgtggtg atattcatgg cagtttcat    240 gaccttgcag aactgttccg aatcggtgga agtgcccag atacaaacta cttgtttatg   300
ggagattacg tggatcgtgg ttattattct gttgaaactg tcacgcttt ggtggcttta    360 aaggttcgtt atcctcagcg aattactatt ctcagaggaa accacgaaag tcgacagatc   420
actcaagttt atggattcta tgacgagtgc ttaaggaagt acgggaatgc aaatgtgtgg   480 aaaacttta cagatctctt cgattacttc cccttgacag cattggttga gtcagaaata    540
ttttgcctgc atggtggatt atcgccatcc attgagacac ttgataacat acgtaacttc   600
gatcgtgtcc aagaagttcc ccatgaaggg cccatgtgtg atcttctgtg gtctgatcca   660
gacgatcgat gtggttgggg tatttctcct cgaggtgctg atacaccttc gggcaggat    720 atatcagagc agttcaacca taccaataat ttaagactta ttgctagagc tcaccagttg   780
gtcatggagg gattcaattg ggctcatgag caaaaagttg ttaccatatt tagtgcacct   840
```

-continued

```
aattattgct atcgctgtgg gaacatggca tcaatcttgg aagttgatga ttgcagggag      900
catacattca tccagtttga gccagcccca agaagggag agccagatgt aactcgtaga      960
acacctgact atttcctgtg atgtaaaagt ggtggactgt ctctgcagca aatgtttgat     1020
agctagctgg gaggattcat cgtgttctca cttatctcta attggctgat gcttggcttg     1080
ggggctgcag tggtgactcg aagcatcaag tagcaaattt gtattatgaa aggaaaacta     1140
ttctctttgt attcattttg ttcgccttc ttccccacaa atttcaccta attttctttt      1200
ttcttttttc atgatccttg tagagatgaa caatgtagtt gtatggctcc ctgttgagcc     1260
ggtaggtctt tctgagtaca tcttgatttg ccgtacataa ttgcttgaaa aacaagtatt     1320
agaattcttt gtgaccaaaa aaaaaaaaaa aaaa                                 1354
```

<210> SEQ ID NO 30
<211> LENGTH: 307
<212> TYPE: PRT
<213> ORGANISM: Oryza sativa

<400> SEQUENCE: 30

```
Met Ser Ser Pro His Gly Gly Leu Asp Asp Gln Ile Glu Arg Leu Met
 1               5                  10                  15

Gln Cys Lys Pro Leu Pro Glu Pro Glu Val Arg Ala Leu Cys Glu Lys
            20                  25                  30

Ala Lys Glu Ile Leu Met Glu Glu Ser Asn Val Gln Pro Val Lys Ser
        35                  40                  45

Pro Val Thr Ile Cys Gly Asp Ile His Gly Gln Phe His Asp Leu Ala
    50                  55                  60

Glu Leu Phe Arg Ile Gly Gly Lys Cys Pro Asp Thr Asn Tyr Leu Phe
65                  70                  75                  80

Met Gly Asp Tyr Val Asp Arg Gly Tyr Tyr Ser Val Glu Thr Val Thr
                85                  90                  95

Leu Leu Val Ala Leu Lys Val Arg Tyr Pro Gln Arg Ile Thr Ile Leu
            100                 105                 110

Arg Gly Asn His Glu Ser Arg Gln Ile Thr Gln Val Tyr Gly Phe Tyr
        115                 120                 125

Asp Glu Cys Leu Arg Lys Tyr Gly Asn Ala Asn Val Trp Lys Thr Phe
    130                 135                 140

Thr Asp Leu Phe Asp Tyr Phe Pro Leu Thr Ala Leu Val Glu Ser Glu
145                 150                 155                 160

Ile Phe Cys Leu His Gly Gly Leu Ser Pro Ser Ile Glu Thr Leu Asp
                165                 170                 175

Asn Ile Arg Asn Phe Asp Arg Val Gln Glu Val Pro His Glu Gly Pro
            180                 185                 190

Met Cys Asp Leu Leu Trp Ser Asp Pro Asp Asp Arg Cys Gly Trp Gly
        195                 200                 205

Ile Ser Pro Arg Gly Ala Gly Tyr Thr Phe Gly Gln Asp Ile Ser Glu
    210                 215                 220

Gln Phe Asn His Thr Asn Asn Leu Arg Leu Ile Ala Arg Ala His Gln
225                 230                 235                 240

Leu Val Met Glu Gly Phe Asn Trp Ala His Glu Gln Lys Val Val Thr
                245                 250                 255

Ile Phe Ser Ala Pro Asn Tyr Cys Tyr Arg Cys Gly Asn Met Ala Ser
            260                 265                 270

Ile Leu Glu Val Asp Asp Cys Arg Glu His Thr Phe Ile Gln Phe Glu
```

```
            275                 280                 285
    Pro Ala Pro Arg Arg Gly Glu Pro Asp Val Thr Arg Arg Thr Pro Asp
        290                 295                 300

Tyr Phe Leu
305
```

<210> SEQ ID NO 31
<211> LENGTH: 1330
<212> TYPE: DNA
<213> ORGANISM: Oryza sativa

<400> SEQUENCE: 31

```
gccgtcaccg tcgcgccaac tgccgcaaac cgaataaacc gaatcgatct gagagaagaa      60
gaagaagaag acgcgatctc ggaggtggga gcgaaacgaa acgatgccgt ctcacgcgga     120
tctggaacga cagatcgagc agctgatgga gtgcaagcct ctgtcggagt cggaggtgaa     180
ggcgctgtgt gatcaagcga gggcgattct cgtggaggaa tggaacgtgc aaccggtgaa     240
gtgccccgtc accgtctgcg gcgatattca cggccagttt tacgatctca tcgagctgtt     300
tcggattgga gggaacgcac ccgataccaa ttatctcttc atgggtgatt atgtagatcg     360
tggatactat tcagtggaga ctgttacact tttggtggct ttgaaagtcc gttacagaga     420
tagaatcaca attctcaggg gaaatcatga agtcgtcaa attactcaag tgtatggctt      480
ctatgatgaa tgcttgagaa aatatggaaa tgccaatgtc tggaaatact ttacagactt     540
gtttgattat ttacctctga ctgccctcat tgagagtcag attttctgct tgcatggagg     600
tctctcacct tctttggata cactggataa catcagagca ttggatcgta caagagggt      660
tccacatgaa ggaccaatgt gtgatctctt gtggtctgac cctgatgatc gctgtggatg     720
gggaatatct ccacgtggtg caggatacac atttggacag gatatagctg ctcagtttaa     780
tcataccaat ggtctctccc tgatatcgag agctcatcag cttgttatgg aaggattcaa     840
ttggtgccag gacaaaaatg tggtgactgt atttagtgca ccaaattact gttaccgatg     900
tgggaatatg gctgctatac tagaaatagg agagaatatg gatcagaatt ccttcagtt      960
tgatccagcg cccaggcaaa ttgagcctga caccacacgc aagactccag attattttt     1020
ataaatttcat ttatctgcct gtttgtagtt actgctctct gccattactg tagatgtgtc    1080
tttaaggaaa ggagttttgc tgtttaagtg gagggtggtc atcaacataa ttctttcttt    1140
tggagtttac ctcctgctgc tgccgctgcc gctgccttat ttgtacaaga accaataga    1200
actgacacaa gccaccaatt ggggttgtat attttttggga ggaagcggta ataacatggt   1260
atatcttgtt ctgtaatcct tttctcttaa attgaatctc aagttagaga gcaaaaaaaa   1320
aaaaaaaaaa                                                          1330
```

<210> SEQ ID NO 32
<211> LENGTH: 306
<212> TYPE: PRT
<213> ORGANISM: Oryza sativa

<400> SEQUENCE: 32

```
Met Pro Ser His Ala Asp Leu Glu Arg Gln Ile Glu Gln Leu Met Glu
  1               5                  10                  15

Cys Lys Pro Leu Ser Glu Ser Glu Val Lys Ala Leu Cys Asp Gln Ala
             20                  25                  30

Arg Ala Ile Leu Val Glu Glu Trp Asn Val Gln Pro Val Lys Cys Pro
         35                  40                  45
```

-continued

Val Thr Val Cys Gly Asp Ile His Gly Gln Phe Tyr Asp Leu Ile Glu
    50                  55                  60

Leu Phe Arg Ile Gly Gly Asn Ala Pro Asp Thr Asn Tyr Leu Phe Met
65                  70                  75                  80

Gly Asp Tyr Val Asp Arg Gly Tyr Tyr Ser Val Glu Thr Val Thr Leu
                85                  90                  95

Leu Val Ala Leu Lys Val Arg Tyr Arg Asp Arg Ile Thr Ile Leu Arg
            100                 105                 110

Gly Asn His Glu Ser Arg Gln Ile Thr Gln Val Tyr Gly Phe Tyr Asp
            115                 120                 125

Glu Cys Leu Arg Lys Tyr Gly Asn Ala Asn Val Trp Lys Tyr Phe Thr
    130                 135                 140

Asp Leu Phe Asp Tyr Leu Pro Leu Thr Ala Leu Ile Glu Ser Gln Ile
145                 150                 155                 160

Phe Cys Leu His Gly Gly Leu Ser Pro Ser Leu Asp Thr Leu Asp Asn
                165                 170                 175

Ile Arg Ala Leu Asp Arg Ile Gln Glu Val Pro His Glu Gly Pro Met
            180                 185                 190

Cys Asp Leu Leu Trp Ser Asp Pro Asp Asp Arg Cys Gly Trp Gly Ile
            195                 200                 205

Ser Pro Arg Gly Ala Gly Tyr Thr Phe Gly Gln Asp Ile Ala Ala Gln
    210                 215                 220

Phe Asn His Thr Asn Gly Leu Ser Leu Ile Ser Arg Ala His Gln Leu
225                 230                 235                 240

Val Met Glu Gly Phe Asn Trp Cys Gln Asp Lys Asn Val Val Thr Val
                245                 250                 255

Phe Ser Ala Pro Asn Tyr Cys Tyr Arg Cys Gly Asn Met Ala Ala Ile
            260                 265                 270

Leu Glu Ile Gly Glu Asn Met Asp Gln Asn Phe Leu Gln Phe Asp Pro
            275                 280                 285

Ala Pro Arg Gln Ile Glu Pro Asp Thr Thr Arg Lys Thr Pro Asp Tyr
    290                 295                 300

Phe Leu
305

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
caggaaacag ctatgacc                                                     18

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ctaaagggaa caaaagctg                                                    19

<210> SEQ ID NO 35

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tgtaaaacga cggccagt                                                     18

<210> SEQ ID NO 36
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
atcccgggac gacatgagtg tgcctccgat atc                                    33

<210> SEQ ID NO 37
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ctgagctcaa gtcccactat aagaagtagt ct                                     32

<210> SEQ ID NO 38
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
atcccgggag gaaggggact ggacacaacg tgatg                                  35

<210> SEQ ID NO 39
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gcgttaacgc accatatgat gctttccggt cgtc                                   34

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ccgttatccg aggtcgaggt cagag                                             25

<210> SEQ ID NO 41
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ccaggtcccg aatgtggtcc aagga                                          25

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cgccaagcgc gcaattaacc ctcact                                         26

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gcgtaatacg actcactata gggcga                                         26

<210> SEQ ID NO 44
<211> LENGTH: 299
<212> TYPE: PRT
<213> ORGANISM: Artificial Sequence
<220> FEATURE:
<223> OTHER INFORMATION: Description of Artificial Sequence: Consensus
      protein sequence

<400> SEQUENCE: 44
```

Met Ser His Gly Leu Asp Gln Ile Glu Gln Leu Met Glu Cys Lys Pro
 1               5                  10                  15

Leu Ser Glu Glu Val Lys Ala Leu Cys Glu Lys Ala Lys Glu Ile Leu
            20                  25                  30

Met Glu Glu Asn Val Gln Pro Val Lys Cys Pro Val Thr Ile Cys Gly
        35                  40                  45

Asp Ile His Gly Gln Phe His Asp Leu Ile Glu Leu Phe Arg Ile Gly
    50                  55                  60

Gly Cys Pro Asp Thr Asn Tyr Leu Phe Met Gly Asp Tyr Val Asp Arg
65                  70                  75                  80

Gly Tyr Tyr Ser Val Glu Thr Val Thr Leu Leu Val Ala Leu Lys Val
                85                  90                  95

Arg Tyr Pro Asp Arg Ile Thr Ile Leu Arg Gly Asn His Glu Ser Arg
            100                 105                 110

Gln Ile Thr Gln Val Tyr Gly Phe Tyr Asp Glu Cys Leu Arg Lys Tyr
        115                 120                 125

Gly Asn Ala Asn Val Trp Lys Phe Thr Asp Leu Phe Asp Tyr Leu Pro
    130                 135                 140

Leu Thr Ala Leu Ile Glu Ser Glu Ile Phe Cys Leu His Gly Gly Leu
145                 150                 155                 160

Ser Pro Ser Ile Asp Thr Leu Asp Asn Ile Arg Ala Leu Asp Arg Val
                165                 170                 175

```
Gln Glu Val Pro His Glu Gly Pro Met Cys Asp Leu Leu Trp Ser Asp
                180                 185                 190

Pro Asp Asp Arg Cys Gly Trp Gly Ile Ser Pro Arg Gly Ala Gly Tyr
            195                 200                 205

Thr Phe Gly Gln Asp Ile Ser Glu Gln Phe Asn His Thr Asn Asn Leu
        210                 215                 220

Lys Leu Ile Ala Arg Ala His Gln Leu Val Met Glu Gly Phe Asn Trp
225                 230                 235                 240

Ala His Glu Lys Lys Val Val Thr Ile Phe Ser Ala Pro Asn Tyr Cys
                245                 250                 255

Tyr Arg Cys Gly Asn Met Ala Ala Ile Leu Glu Val Asp Asp Asn Met
            260                 265                 270

Asp His Thr Phe Ile Gln Phe Glu Pro Ala Pro Arg Arg Gly Glu Pro
        275                 280                 285

Asp Val Thr Arg Lys Thr Pro Asp Tyr Phe Leu
290                 295

<210> SEQ ID NO 45
<211> LENGTH: 255
<212> TYPE: PRT
<213> ORGANISM: Artificial Sequence
<220> FEATURE:
<223> OTHER INFORMATION: Description of Artificial Sequence: Consensus
      protein sequence

<400> SEQUENCE: 45

Met Asp Ile Asp Arg Ile Leu Lys Leu Ser Glu Ser Glu Ile Arg Leu
 1               5                  10                  15

Cys Glu Ala Arg Glu Ile Leu Leu Glu Asn Val Gln Pro Val Ala Pro
                20                  25                  30

Val Thr Ile Cys Gly Asp Ile His Gly Gln Phe His Asp Leu Leu Arg
            35                  40                  45

Leu Phe Gly Gly Pro Asp Thr Asn Tyr Leu Phe Met Gly Asp Tyr Val
        50                  55                  60

Asp Arg Gly Tyr Ser Leu Glu Thr Ile Thr Leu Leu Ala Leu Lys
65                  70                  75                  80

Val Arg Tyr Pro Asp Asn Ile Thr Leu Leu Arg Gly Asn His Glu Ser
                85                  90                  95

Arg Gln Ile Thr Gln Val Tyr Gly Phe Tyr Asp Glu Cys Arg Lys Tyr
            100                 105                 110

Gly Asn Ala Asn Leu Trp Lys Phe Thr Asp Leu Phe Asp Tyr Leu Pro
        115                 120                 125

Leu Thr Ala Leu Ile Asp Ile Leu Cys Leu His Gly Gly Leu Ser Pro
130                 135                 140

Asp Leu Thr Leu Asp Asn Ile Arg Leu Asp Arg Glu Val Pro His Glu
145                 150                 155                 160

Gly Pro Leu Cys Asp Leu Leu Trp Ser Asp Pro Asp Val Gly Trp
                165                 170                 175

Gly Ile Ser Pro Arg Gly Ala Gly Tyr Thr Phe Gly Asp Ile Ala Gln
            180                 185                 190

Phe Asn His Asn Leu Asp Leu Ile Cys Arg Ala His Gln Leu Val Asp
        195                 200                 205

Gly Tyr Phe Asp Arg Gln Leu Val Thr Ile Phe Ser Ala Pro Asn Tyr
    210                 215                 220

Cys Tyr Arg Cys Gly Asn Met Ala Ala Ile Leu Ser Val Asp Glu Asn
```

-continued

```
                225                 230                 235                 240
Met Ser Phe Phe Pro Ala Arg Lys Thr Arg Lys Thr Tyr Phe Leu
                    245                 250                 255

<210> SEQ ID NO 46
<211> LENGTH: 283
<212> TYPE: PRT
<213> ORGANISM: Artificial Sequence
<220> FEATURE:
<223> OTHER INFORMATION: Description of Artificial Sequence: Consensus
      protein sequence

<400> SEQUENCE: 46

Gly Leu Asp Asp Gln Ile Gln Leu Met Glu Cys Lys Leu Ser Glu Ser
  1               5                  10                  15

Glu Val Arg Leu Cys Glu Ala Lys Glu Ile Leu Met Glu Glu Asn Val
                 20                  25                  30

Gln Pro Val Lys Ala Pro Val Thr Ile Cys Gly Asp Ile His Gly Gln
             35                  40                  45

Phe His Asp Leu Leu Glu Leu Phe Arg Ile Gly Gly Pro Asp Thr Asn
         50                  55                  60

Tyr Leu Phe Met Gly Asp Tyr Val Asp Arg Gly Tyr Tyr Ser Val Glu
 65                  70                  75                  80

Thr Val Thr Leu Leu Val Ala Leu Lys Val Arg Tyr Pro Asp Arg Ile
                 85                  90                  95

Thr Ile Leu Arg Gly Asn His Glu Ser Arg Gln Ile Thr Gln Val Tyr
            100                 105                 110

Gly Phe Tyr Asp Glu Cys Leu Arg Lys Tyr Gly Asn Ala Asn Val Trp
        115                 120                 125

Lys Phe Thr Asp Leu Phe Asp Tyr Leu Pro Leu Thr Ala Leu Ile Glu
    130                 135                 140

Ser Ile Phe Cys Leu His Gly Gly Leu Ser Pro Ser Leu Asp Thr Leu
145                 150                 155                 160

Asp Asn Ile Arg Leu Asp Arg Ile Gln Glu Val Pro His Glu Gly Pro
                165                 170                 175

Met Cys Asp Leu Leu Trp Ser Asp Pro Asp Asp Arg Cys Gly Trp Gly
            180                 185                 190

Ile Ser Pro Arg Gly Ala Gly Tyr Thr Phe Gly Gln Asp Ile Ala Ala
        195                 200                 205

Gln Phe Asn His Thr Asn Leu Leu Ile Ala Arg Ala His Gln Leu Val
    210                 215                 220

Met Glu Gly Tyr Asn Trp Asp Arg Gln Val Val Thr Ile Phe Ser Ala
225                 230                 235                 240

Pro Asn Tyr Cys Tyr Arg Cys Gly Asn Met Ala Ala Ile Leu Glu Val
                245                 250                 255

Asp Glu Asn Met Ser Phe Ile Gln Phe Asp Pro Ala Pro Arg Arg Glu
            260                 265                 270

Pro Asp Thr Arg Lys Thr Pro Asp Tyr Phe Leu
        275                 280
```